US011779642B2

(12) United States Patent
Pincetic et al.

(10) Patent No.: US 11,779,642 B2
(45) Date of Patent: Oct. 10, 2023

(54) ANTI-SIRP-ALPHA ANTIBODIES AND METHODS OF USE THEREOF

(71) Applicant: Alector LLC, South San Francisco, CA (US)

(72) Inventors: Andrew Pincetic, San Francisco, CA (US); Arnon Rosenthal, Woodside, CA (US); Seung-Joo Lee, South San Francisco, CA (US)

(73) Assignee: Alector LLC, South San Francisco, CA (US)

( * ) Notice: Subject to any disclaimer, the term of this patent is extended or adjusted under 35 U.S.C. 154(b) by 643 days.

(21) Appl. No.: 16/463,062

(22) PCT Filed: Dec. 8, 2017

(86) PCT No.: PCT/US2017/065366
§ 371 (c)(1),
(2) Date: May 22, 2019

(87) PCT Pub. No.: WO2018/107058
PCT Pub. Date: Jun. 14, 2018

(65) Prior Publication Data
US 2019/0275150 A1    Sep. 12, 2019

Related U.S. Application Data

(60) Provisional application No. 62/432,503, filed on Dec. 9, 2016.

(51) Int. Cl.
*A61K 39/395*   (2006.01)
*A61P 31/00*   (2006.01)
*A61P 35/00*   (2006.01)
*C07K 16/28*   (2006.01)

(52) U.S. Cl.
CPC ........ *A61K 39/39558* (2013.01); *A61P 31/00* (2018.01); *A61P 35/00* (2018.01); *C07K 16/2803* (2013.01); *C07K 2317/24* (2013.01); *C07K 2317/732* (2013.01); *C07K 2317/75* (2013.01); *C07K 2317/76* (2013.01); *C07K 2317/77* (2013.01); *C07K 2317/92* (2013.01)

(58) Field of Classification Search
CPC .... A61K 39/39558; A61P 31/00; A61P 35/00; A61P 9/10; A61P 35/02; A61P 25/28; A61P 25/16; A61P 25/14; A61P 25/00; C07K 16/2803; C07K 2317/24; C07K 2317/76; C07K 2317/77; C07K 2317/75; C07K 2317/732; C07K 2317/92
See application file for complete search history.

(56) References Cited

U.S. PATENT DOCUMENTS

| 6,180,370 | B1 | 1/2001 | Queen et al. |
| 8,562,997 | B2 | 10/2013 | Jaiswal et al. |
| 9,399,682 | B2 | 7/2016 | Jaiswal et al. |
| 9,493,575 | B2 | 11/2016 | Jaiswal et al. |
| 9,605,076 | B2 | 3/2017 | Jaiswal et al. |
| 9,611,329 | B2 | 4/2017 | Jaiswal et al. |
| 9,624,305 | B2 | 4/2017 | Jaiswal et al. |
| 9,765,143 | B2 | 9/2017 | Jaiswal et al. |
| 10,081,680 | B2 | 9/2018 | Weiskopf et al. |
| 2002/0114807 | A1 | 8/2002 | Berg |
| 2003/0054415 | A1 | 3/2003 | Buhring et al. |
| 2019/0359707 | A1* | 11/2019 | Pincetic ................. C07K 16/40 |

FOREIGN PATENT DOCUMENTS

| CL | 2019003266 A1 | 3/2020 | |
| CL | 2020002305 A1 | 2/2021 | |
| CL | 2021000738 A1 | 8/2021 | |
| CL | 2021001260 A1 | 12/2021 | |
| CL | 2021001627 A1 | 1/2022 | |
| WO | 2001040307 A1 | 6/2001 | |
| WO | 2002092784 A2 | 11/2002 | |
| WO | 2009046541 A1 | 4/2009 | |
| WO | 2009091547 A1 | 7/2009 | |
| WO | 2009091601 A1 | 7/2009 | |
| WO | 2009131453 A1 | 10/2009 | |
| WO | 2010130053 A1 | 11/2010 | |
| WO | 2013056352 A1 | 4/2013 | |
| WO | 2014123580 A1 | 8/2014 | |
| WO | 2014124028 A1 | 8/2014 | |
| WO | WO-2015138600 A2 * | 9/2015 | ......... C07K 16/2803 |
| WO | 2015138600 A3 | 11/2015 | |
| WO | 2015177360 A1 | 11/2015 | |
| WO | 2016063233 A1 | 4/2016 | |
| WO | 2016205042 A1 | 12/2016 | |
| WO | 2017068164 A1 | 4/2017 | |
| WO | 2017178653 A2 | 10/2017 | |
| WO | 2017180519 A1 | 10/2017 | |

(Continued)

OTHER PUBLICATIONS

De Vries HE, Hendriks JJ, Honing H, De Lavalette CR, van der Pol SM, Hooijberg E, Dijkstra CD, van den Berg TK. Signal-regulatory protein alpha-CD47 interactions are required for the transmigration of monocytes across cerebral endothelium. J. Immunol. Jun. 1, 2002;168(11):5832-9. (Year: 2002).*
Bio-Rad Antibodies (formerly AbD Serotec), Mouse anti Rat CD172a antibody, clone OX-41, 2021 (Year: 2021).*
Padlan (Advances in Protein Chemistry, 1996, 49:57-133) (Year: 1996).*
Janeway CA Jr, Travers P, Walport M, et al. Immunobiology: The Immune System in Health and Disease. 5th edition. New York: Garland Science; 2001. (Year: 2001).*
Edwards et al. 2003. The remarkable flexibility of the human antibody repertoire; isolation of over one thousand different antibodies to a single protein, BlyS. Journal of Molecular Biology 334:103-118 (Year: 2003).*

(Continued)

*Primary Examiner* — Julie Wu
*Assistant Examiner* — Francesca Edgingtongiordan
(74) *Attorney, Agent, or Firm* — McNeill Baur PLLC

(57) ABSTRACT

The invention provides anti-SIRPA antibodies, methods of generating such antibodies, and therapeutic uses and methods employing the antibodies.

20 Claims, 37 Drawing Sheets

Specification includes a Sequence Listing.

(56) References Cited

FOREIGN PATENT DOCUMENTS

| WO | 2017184553 A1 | 10/2017 |
| WO | 2017197495 A1 | 11/2017 |
| WO | 2018026600 A1 | 2/2018 |
| WO | 2018057669 A1 | 3/2018 |
| WO | 2018107058 A1 | 6/2018 |
| WO | 2017178653 A3 | 7/2018 |
| WO | 2018190719 A2 | 10/2018 |
| WO | 2018210795 A1 | 11/2018 |
| WO | 2018210793 A3 | 12/2018 |
| WO | 2019022600 A1 | 1/2019 |
| WO | 2019023347 A1 | 1/2019 |
| WO | 2019175218 A1 | 9/2019 |
| WO | 2020068752 A1 | 4/2020 |
| WO | 2020099653 A1 | 5/2020 |
| WO | 2020127373 A1 | 6/2020 |

OTHER PUBLICATIONS

Berglund (Protein Science, 2008, 17:606-613) (Year: 2008).*
Fournier B, et al. Surfactant protein D (Sp-D) binds to membrane-proximal domain (D3) of signal regulatory protein α (SIRPα), a site distant from binding domain of CD47, while also binding to analogous region on signal regulatory protein β (SIRPβ). J Biol Chem. Jun. 1, 2012;287(23):19386-98. (Year: 2012).*
Mimoto F, Katada H, Kadono S, et al. Engineered antibody Fc variant with selectively enhanced FcγRIIb binding over both FcγRIIa(R131) and FcγRIIa(H131). Protein Eng Des Sel. 2013;26(10):589-598. (Year: 2013).*
Kafeel Ahmad, Insulin sources and types: a review of insulin in terms of its mode on diabetes mellitus, Apr. 15, 2014 Journal of Traditional Chinese Medicine, vol. 34, Issue 2 (Year: 2014).*
Rissiek B, et al. Nanobodies as modulators of inflammation: potential applications for acute brain injury. Front Cell Neurosci. 2014;8:344. Published Oct. 21, 2014. (Year: 2014).*
Huang et al. Trastuzumab-cisplatin conjugates for targeted delivery of cisplatin to HER2-overexpressing cancer cells. Biomed Pharmacother. May 2015;72:17-23. (Year: 2015).*
Muchtar E, Buadi FK, Dispenzieri A, Gertz MA. Immunoglobulin Light-Chain Amyloidosis: From Basics to New Developments in Diagnosis, Prognosis and Therapy. Acta Haematol. 2016;135(3):172-90. (Year: 2016).*
Liu et al. Inhibition of SIRPα in dendritic cells potentiates potent antitumor immunity. Oncoimmunology. Aug. 23, 2016;5(9):e1183850. (Year: 2016).*
Sharma, Gitanjali et al. "The Role of Cell-Penetrating Peptide and Transferrin on Enhanced Delivery of Drug to Brain." International journal of molecular sciences vol. 17,6 806. May 25, 2016, doi:10.3390/ijms17060806 (Year: 2016).*
Chen (Sci Adv. Apr. 1, 2020;6(14):eaaz7825) (Year: 2020).*
Alblas et al., "Signal Regulatory Protein alpha Ligation Induces Macrophage Nitric Oxide Production through JAK/STAT-and Phosphatidylinositol3-Kinase/Racl/NAPDH Oxidase/H2O2-Dependent Pathways," Molecular and Cellular Biology, vol. 25, No. 16, pp. 7181-7192 (Aug. 15, 2005).
Anonymous, "MABS164 | Anti-SHPS-1 Antibody, clone P84," 4 pages (Jan. 1, 2016). Retrieved from the Internet: www.merckmillipore.com/NL/en/product/Anti-SHPS-1-Antibody,-clone-P84,MM N F-MABS164#anchor Packaging%20Information.
De Vries et al., "Signal-regulatory protein alpha-CD47 interactions are required for the transmigration of monocytes across cerebral endothelium," The Journal of Immunology, vol. 168, No. 11, pp. 5832-5839 (Jun. 1, 2002).
International Search Report and Written Opinion issued in PCT/US2017/065366 dated Mar. 26, 2018, 18 pages.
Lee et al., "Novel structural determinants on SIRP alpha that mediate binding to CD47," Journal of Immunology, vol. 179, No. 11, pp. 7741-7750 (Jan. 1, 2007).
Oldenborg, P., "Cd47-Signal Regulatory Protein [alpha] (Sirp[alpha]) Regulates Fc[gamma] and Complement Receptor-Mediated Phagocytosis," The Journal of Experimental Medicine, vol. 193, No. 7, pp. 855-861 (Apr. 2, 2001).
Seiffert et al., "Signal-regulatory protein alpha (SIRPalpha) but not SIRPbeta is involved in T-Cell activation, binds to CD47 with high affinity, and is expressed on immature CD34+CD38- hematopoietic cells," Blood, vol. 97, No. 9, pp. 2741-2749 (May 1, 2001).
Yanagita et al., Anti-SIRP [alpha] antibodies as a potential new tool for cancer immunotherapy, JCI Insight, vol. 2, No. 1, pp. 2379-3708 (Jan. 12, 2017).
Adams et al., "Signal-Regulatory Protein Is Selectively Expressed by Myeloid and Neuronal Cells," J Immunol 1998; 161:1853-1859.
Alblas et al., "Signal Regulatory Protein α Ligation Induces Macrophage Nitric Oxide Production through JAK/STAT-and Phosphatidylinositol3-Kinase/Rac1/NAPDH Oxidase/H2O2-Dependent Pathways," Molecular and Cellular Biology, vol. 25, No. 16, pp. 7181-7192, Aug. 2005.
Barclay et al., "Signal regulatory protein alpha (SIRPα) / CD47 interaction and function," Curr Opin Immunol. Feb. 2009 ; 21(1): pp. 47-52.
Chiavenna et al., "State of the art in anti-cancer mAbs," Journal of Biomedical Science, 2017, 24:15 (12 pages).
Fournier et al., "Surfactant Protein D (Sp-D) Binds to Membrane-proximal Domain (D3) of Signal Regulatory Protein (SIRPα), a SiteDistant from Binding Domain of CD47, while Also Binding to Analogous Region on Signal Regulatory Protein β ((SIRPα)", J Biol Chem, 2012, 287:19386-19398.
Hatherley et al., "Polymorphisms in the Human Inhibitory Signal-regulatory Protein Do Not Affect Binding to Its Ligand CD47," The Journal of Biological Chemistry, vol. 289, No. 14, pp. 10024-10028, Apr. 4, 2014.
Lee et al., "Novel Structural Determinants on SIRPa that Mediate Binding to CD47," J Immunol 2007; 179:7741-7750.
Liu et al., "Functional Elements on SIRPα IgV domain Mediate Cell Surface Binding to CD47," J Mol Biol. Jan. 19, 2007; 365(3): 680-693.
Liu et al., "Signal regulatory protein (SIRPα), a cellular ligand for CD47, regulates neutrophil transmigration," The American Society for Biochemistry and Molecular Biology, J Biol Chem, 2002, 277:10028-10036.
Matozaki et al., "Functions and molecular mechanisms of the CD47-SIRPα signalling pathway," Trends Cell Biol, 2009, 19:72-80.
Murata et al., "The CD47SIRPa signalling system: its physiological roles and therapeutic application," J. Biochem. 2014;155(6):335-344.
Pan et al., "Signal Regulatory Protein a Is Associated With Tumor-Polarized Macrophages Phenotype Switch and Plays a Pivotal Role in Tumor Progression," Hepatology, vol. 58, No. 2, pp. 680-691, 2013.
Seiffert et al., "Human Signal-Regulatory Protein Is Expressed on Normal, But Not on Subsets of Leukemic Myeloid Cells and MediatesCellular Adhesion Involving Its Counterreceptor CD47," Blood, vol. 94, No. 11, pp. 3633-3646, Dec. 1, 1999.
Seiffert et al., "Signal-regulatory protein a (SIRPα) but not SIRPβ is involved in T-cell activation, binds to CD47 with high affinity, and is expressed on immature CD34+CD38- hematopoietic cells," Blood, vol. 97, No. 9, pp. 2741-2749, May 2001.
Van Beek et al., "Signal Regulatory Proteins in the Immune System," J Immunol 2005; 175:7781-7787.
Weiskopf et al.,"Cancer immunotherapy targeting the CD47/SIRPα axis", Trends Cell Biol, 2009, 19:72-80.
Willingham et al., "The CD47-signal regulatory protein alpha (SIRPa) interaction is a therapeutic target for human solid tumors," PNAS, vol. 109, No. 17, pp. 6662-6667, Apr. 24, 2012.
Yanagita et al., "Anti-SIRPα antibodies as a potential new tool for cancer immunotherapy," JCI Insight, 2(1) e89140, 2017 (15 pages).
Zhao et al., "CD47-signal regulatory protein-α (SIRPα) interactions form a barrier for antibody-mediated tumor cell destruction," PNAS, vol. 108, No. 45, pp. 18342-18347, Nov. 8, 2011.
Zhao et al., "Is targeting of CD47-SIRPα enough for treating hematopoietic malignancy?" Blood, vol. 119, No. 18, pp. 4333-4334, 2012.

(56) References Cited

OTHER PUBLICATIONS

Chao et al., "Response: mechanisms of targeting CD47-SIRPα in hematologic malignancies," Blood, vol. 119, No. 18 pp. 4334-4335, 2012.
Cosmetology, vol. 18, pp. 57-61 (2010).
Sim, J., et al., "Discovery of high affinity, pan-allelic, and pan-mammalian reactive antibodies against the myeloid checkpoint receptors SIRP[alpha]", mAbs, vol. 11, No. 6, pp. 1036-1052 (Jul. 1, 2019).
International Search Report and Written Opinion of International Application No. PCT/US2019/0363884, dated Aug. 27, 2019 (16 pages).
Bostrom et al., "Improving antibody binding affinity and specificity for therapeutic development", Methods in Molecular Biology, 2009; vol. 525, pp. 353-376.
Gonzales et al., "Minimizing the Immunogenicity of Antibodies for Clinical Application", Tumour Biol., Jan.-Feb. 2005, vol. 26, No. 1, pp. 31-43.
Kipriyanov et al., "Generation and production of engineered antibodies," Molecular Biotechnology, vol. 26, No. 1, pp. 39-60 (2004).
Kunik et al., "Structural consensus among antibodies defines the antigen binding site", PLoS Comput Biol., Feb. 23, 2012, vol. 8, No. 2, Feb. 23, 2012.
Wark et al., "Latest technologies for the enhancement of antibody affinity", Advanced Drug Delivery Reviews, Elsevier, vol. 58, No. 5-6, Aug. 7, 2006, pp. 657-670.

\* cited by examiner

FIGURE 1A

```
  1 MEPRKQPAPGRLQPLLCLLLAASCAWSGVAGEEELQVIQPDKSVLVAAGETATLRCTATSL   60
  1 MEPRKQPAPGRLQPLLCLLLAASCAWSGVAGEEELQVIQPDKSVLVAAGESAILHCTVTSL   60
    ************************************************ * *** ***

61 IPVGPIQWFRGAGPGRELIYNQKEGHFPRVTTVSDLTKRNNMDFSIRIGNITPADAGTYY  120
 61 IPVGPIQWFRGAGPAREIIYNQKEGHFPRVTTVSESTKREMDFSISISNITPADAGTYY   120
    ************** *  *****************      **** *   *********

121 CVKFRKGSPDDVEFKSGAGTELSVRAKPSAPVVSGPAARATPQHTVSFTCESHGFSPRDI  180
121 CVKFRKGSPD--TEEKSGAGTELSVRAKPSAPVVSGPAARATPQHTVSFTCESHGFSPRDI 179
    **********   * ********************************************

181 TLKWFKNGNELSDFQTNVDPVGESVSYSIHSTAKVVLTREDVHSQVICEVAHVTLQGDPL  240
180 TLKWFKNGNELSDFQTNVDPVGESVSYSIHSTAKVVLTREDVHSQVICEVAHVTLQGDPL  239
    ************************************************************

241 RGTANLSETIRVPPTLEVTQQPVRAEMQVNVTCQVRKFYPQRLQLTWLENGNVSRTETAS  300
240 RGTANLSETIRVPPTLEVTQQPVRAEMQVNVTCQVRKFYPQRLQLTWLENGNVSRTETAS  299
    ************************************************************

301 TVTENKDGTYNWMSWLLVNVSAHRDDVKLTCQVEHDGQPAVSKSHDLKVSAHPKEQGSNT  360
300 TVTENKDGTYNWMSWLLVNVSAHRDDVKLTCQVEHDGQPAVSKSHDLKVSAHPKEQGSNT  359
    ************************************************************

361 AAENTGSNERNIYIVVGVVCTLLVALLMAALYLVRIRQKKAQGSTSSTRLHEPEKNAREI  420
360 AAENTGSNERNIYIVVGVVCTLLVALLMAALYLVRIRQKKAQGSTSSTRLHEPEKNAREI  419
    ************************************************************

421 TQDTNDITYADLNLPGKKPAPQAAEPNNHTEYASIQTSPQPASEDTLTYADLDMVHLNR   480
420 TQDTNDITYADLNLPGKKPAPQAAEPNNHTEYASIQTSPQPASEDTLTYADLDMVHLNR   479
    ************************************************************

481 TPKQPAPKPEPSFSEYASVQVPRK                                      504
480 TPKQPAPKPEPSFSEYASVQVPRK                                      503
    ***********************
```

FIGURE 1B

```
MEPAGPAPGRLGPLLCLLLASCAWSGVAGEELQVIQPDKSVLVAAGETATLRCTATSL    60
MPVPASWPELPSPFL--LMTLLLGRLTGVAGEDELQVIQPERSVSVAAGESATLRCAMTSL 59
*    ;  .  :****       ;**********  * .* ;***  **.*****.*.**  :***

IPVGPIQWFRGAGPGRELIYNQKEGHFPRVTTVSDLTKRNNMDFSIRIGNITPADAGTYY  120
IPVGPIMWFRGAGACRELIYNQKEGHFPRVTTVSELTKRNNLDFSISISNITPADAGTYY 119
******:*****.****************:*****.******;******* *********

CVKFRKGSPDDVEFKSGAGTELSVRAKPSAPVVSGPAARATPQHTVSFTCESHGFSPRDI 180
CVKFRKGSPDDVETKSGACTELSVRAKPSAPVVSCPAVRATPEHTVSFTCESHGFSPRDI 179
*************.****.**************.**;****:**************

RCTANLSEEIRVPPTLEVTQQPVRAENQVAVTCQVRKFYPQRLQLTWLENGNVSRTETAS 240
RCTAWLSETIRVPPTLEVTQQPVRAENQVAVTCQVRKFYPQRLQLTWLENGNVSRTETAS 300
TVTEDKDGTYNWMSWLLVNVSAERDDVKLTCQVEHDGQPAVSKSHDLKVSAHPKEQGSNT 360
TLIENKDGTYNWMSWLLVNTCAHRDDVLCQVEHDGQAVSKSYALEISAHQKEHGSDI 359
*;  .****,.*****;;;***..  ;***** *;:****. .  *;**  ;****;

AARNTCSMERNIYIVVGVYCTLVALLMAALYLVRIBQKKAQCSTSSTRLHEPEKNAREI  420
THRAALAPTAPLIVALLGPKLLIVVCVSAIYICMKQRA---------------------- 398

TQQTNDITYADLMLPGKRKPAPQAAEPWMHTEYASTQTSPQPASEPDTLYADLDMVELNR 480

TPKQPAPKPEPSPSEYASVQVPRK 504
```

FIGURE 2

FIGURE 13B
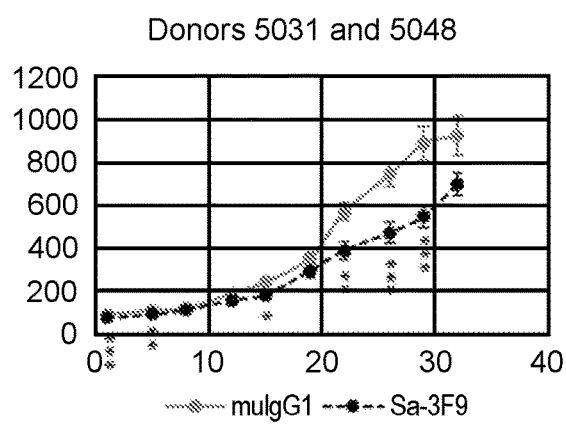
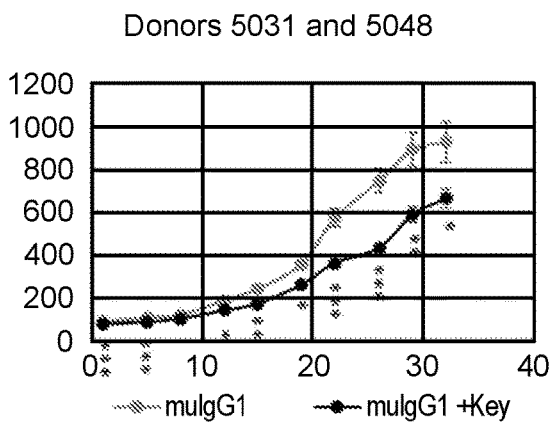
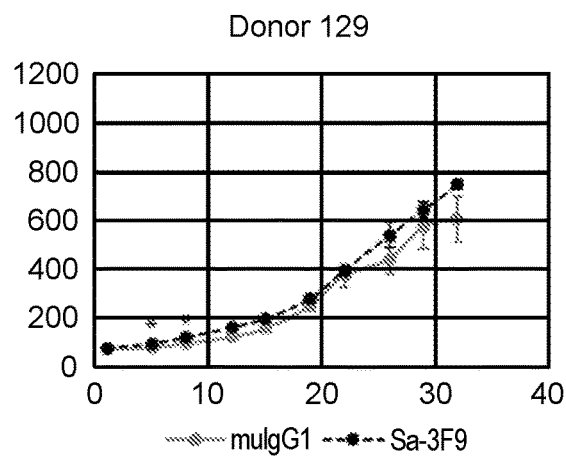
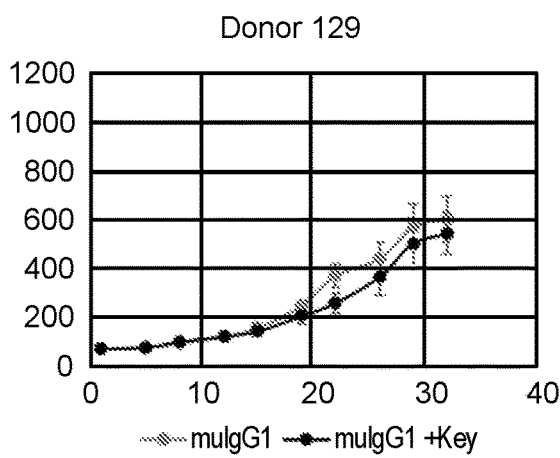

FIGURE 14A

```
Potential humanized sequence based on IGHV3-23*01 acceptor framework (AbM CDR definition)
IGHV3-23*01  EVQLLESGGGLVQPGGSLRLSCAASGFTFSSYAMSWVRQAPGKGLEWVSAISGSGGSTYYADSVKG
             RFTISRDNSKNTLYLQMNSLRAEDTAVYYCAK
Joining region  IMGT J00256|IGHJ4*01|YFDYWGQGTLVTVSS 10         20         30         40         50         60
seq                       10         20         30         40         50         60
AbM                                                                        ab
SB-3F9       b b b   b       p b b b  b b     b  b i i i  ibb b
             EVKLVESGGGLVKPGGSLKLSCAAS GFTFSSYAMS WVRQTPEKRLEWVA TISDYGGSYTY
                     *                      *                         *
IGHV3-23*01  EVQLLESGGGLVQPGGSLRLSCAAS GFTFSSYAMS WVRQAPGKGLEWVS AISG-SGGSTY
hSB-3F9-H1   EVQLLESGGGLVQPGGSLRLSCAAS GFTFSSYAMS WVRQAPGKGLEWVS TISDYGGSYTY
hSB-3F9-H2   EVQLLESGGGLVQPGGSLRLSCAAS GFTFSSYAMS WVRQAPGKGLEWVA TISDYGGSYTY 70         80         90        100        110        120
seq                       70       80 abc         90                100abcd        110
AbM                     i b   b b b x   b b b b     bibibb            i    b b b
SB-3F9       YPDSVKGRFTISRDNAKYTLYLQMSSLRSEDTALYYCAR PPYDDYIGGFAY WGQGTLVTVSA
                                           *                              *
IGHV3-23*01  YADSVKGRFTISRDNSKNTLYLQMNSLRAEDTAVYYCAK
hSB-3F9-H1   YADSVKGRFTISRDNSKNTLYLQMNSLRAEDTAVYYCAR PPYDDYIGGFAY WGQGTLVTVSS
hSB-3F9-H2   YADSVKGRFTISRDNSKNTLYLQMNSLRAEDTAVYYCAR PPYDDYIGGFAY WGQGTLVTVSS
             p                             L
```

FIGURE 14B

Potential humanized sequence based on IGKV3-11*01 acceptor framework (AbM CDR definition)
IGKV3-11*01 EIVLTQSPATLSLSPGERATLSCRASQSVSSYLAWYQQKPGQAPRLLIYDASNRAT
            GIPARFSGSGSGTDFTLTISSLEPEDFAVYYCQQRSNWPP
Joining region IMGT J00242|IGKJ2*01|YTFGQGTKLEIK

```
                          10         20         30         40         50         60
seq                       10         20       30abcd        40         50
AbM          b b b     p p      b b b      b      bi bi i    ii ibbi   i
SB-3F9       DIVLTQSPASLAVSLGQRATISC RASKSVSSSGYSYMH WYQQKPGQPPPKLLIY LASNLES
                *         *          *              *              *       #

3-11*01      EIVLTQSPATLSLSPGERATLSC RASQSVS----SYLA WYQQKPGQAPRLLIY DASNRAT
hSB-3F9-L1   EIVLTQSPATLSLSPGERATLSC RASKSVSSSGYSYMH WYQQKPGQAPRLLIY LASNLES
hSB-3F9-L2   EIVLTQSPATLSLSPGERATISC RASKSVSSSGYSYMH WYQQKPGQAPRLLIY LASNLES
hSB-3F9-L3   EIVLTQSPATLSLSPGERATISC RASKSVSSSGYSYMH WYQQKPGQAPRLLIY LASNLES
                           V                                    P            #

70         80         90        100        110
seq                       70         80         90        100        110
AbM          b    b    b b b b      ib bib    ibi iib  i    b b
SB-3F9       GVPARFSGSGSGSGTDFTLMIHPVEEEDAATYYC QHHRELPCT FGGGTKLEIK
                *                   *    *         *              *

3-11*01      GIPARFSGSGSGTDFTLTISSLEPEDFAVYYC QQRSNWPP
hSB-3F9-L1   GIPARFSGSGSGTDFTLTISSLEPEDFAVYYC QHHRELPCT FGQGTKLEIK
hSB-3F9-L2   GVPARFSGSGSGTDFTLTISSVEPEDFAVYYC QHHRELPCT FGQGTKLEIK
hSB-3F9-L3   GVPARFSGSGSGTDFTLTISSVEPEDFAVYYC QHHRELPST FGQGTKLEIK
                                       A                     #
```

FIGURE 14C

```
Potential humanized sequence based on IGHV1-46*01 acceptor framework (AbM CDR definition)
IGHV1-46*01   QVQLVQSGAEVKKPGASVKVSCKASGYTFTSYYMHWVRQAPGQGLEWMGIINPSGGSTSYAQKFQG
              RVTMTRDTSTSTVYMELSSLRSEDTAVYYCAR
Joining region IMGT J00256|IGHJ4*01|YFDYWGQGTLVTVSS 10         20         30         40         50
                       10         20         30         40         50 a
seq            b b b   b    p    b b b b    b    b  b bi i       i ibb b
AbM            * * *                             *  *            * * *
SB-9C2         EFQLQQSGAELVKPGASVKISCKAS GYSLTGYTMH WVKQSRGKSLEWMG MINPHYGSST IGHV1-46*01    QVQLVQSGAEVKKPGASVKVSCKAS GYTFTSYYMH WVRQAPGQGLEWMG IINPSGGSTS
hSB-9C2-H1     QVQLVQSGAEVKKPGASVKVSCKAS GYSLTGYTMH WVRQAPGQGLEWMG MINPHYGSST
hSB-9C2-H2     QVQLVQSGAEVKKPGASVKISCKAS GYSLTGYTMH WVRQAPGQGLEWMG MINPHYGSST
hSB-9C2-H3     QVQLVQSGAEVKKPGASVKISCKAS GYSLTGYTMH WVRQAPGQGLEWIG MINPHYGSST
hSB-9C2-H4     QVQLVQSGAEVKKPGASVKISCKAS GYSLTGYTMH WVRQAPGQGLEWIG MINPHYGSST
                                                                 # #

70         80  abc       90         100 100a     110
                        70         80  b b b     90            100 a     110
seq          b     b    b b b b x  b b b   b     b b i b b                i b b b
AbM                     *  * * *    *  *        *                         *
SB-9C2       YWQNFKDKATLTVDKSSSAAYMQFWSLTSEDSAVYYCAR EGIDGVFDY WGQGTLTVSS IGHV1-46*01  YAQKFQGRVTMTRDTSTSTVYMELSSLRSEDTAVYYCAR
hSB-9C2-H1   YAQKFQGRVTMTRDTSTSTVYMELSSLRSEDTAVYYCAR EGIDGVFDY WGQGTLVTVSS
hSB-9C2-H2   YAQKFQGRVTMTVDTSTSTVYMELSSLRSEDTAVYYCAR EGIDGVFDY WGQGTLVTVSS
hSB-9C2-H3   YAQKFQGRATLTVDKSTSTAYMEFSSLRSEDTAVYYCAR EGIDGVFDY WGQGTLATVSS
hSB-9C2-H4   YAQKFQGRATLTVDKSTSTAYMEFSSLRSEDTAVYYCAR EGIDGVFDY WGQGTLVTVSS
             M                                      @
```

FIGURE 14D potential humanized sequence based on IGKV3-11*01 acceptor framework (AbM CDR definition)
IGKV3-11*01 EIVLTQSPATLSLSPGERATLSCRASQSVSSYLAWYQQKPGQAPRLLIYDASNRAT
              GIPARFSGSGSGTDFTLTISSLEPEDFAVYYCQQRSNWPP
Joining region IMGT J00243|IGKJ2*01|YTFGQGTKLEIK

```
                       10         20         30         40         50
seq                    10         20         30         40         50
AbM          b b b     p p    b b b   b   b    bi bi i    ii ibbi   i
SB-9C2       QIVLSQSPAILSASPSEKVTMYC RASQSVSSYLA WYQQKPGSSPKPWIY VTSNLAS
             *           *  *         *** ***                  ***
3-11*01      EIVLTQSPATLSLSPGERATLSC RASSSVS-YMH WYQQKPGQAPRLLIY DASNRAT
hSB-9C2-L1   EIVLTQSPATLSLSPGERATLSC RASSSVS-YMH WYQQKPGQAPRLLIY VTSNLAS
hSB-9C2-L2   EIVLTQSPATLSLSPGERATLSC RASSSVS-YMH WYQQKPGQAPRPLIY VTSNLAS
hSB-9C2-L3   EIVLTQSPATLSLSPGERATLSC RASSSVS-YMH WYQQKPGQAPRPWIY VTSNLAS
hSB-9C2-L4   EIVLTQSPATLSLSPGERVTMSC RASSSVS-YMH WYQQKPGQAPRPWIY VTSNLAS
                         A                                 #

60         70         80         90        100
seq                60         70         80         90        100
AbM          b b             b b b b    ib bib   ibi ibi  iib i   b b b
SB-9C2       GVPTRFSGSGSGTSYSLTISRVEAEDAATYYC QQWSSNPRT FGQGTKLEIK
             * *                 ***  * * *                  *
3-11*01      GIPARFSGSGSGTDFTLTISSLEPEDFAVYYC QQRSNWPP
hSB-9C2-L1   GIPARFSGSGSGTDFTLTISSLEPEDFAVYYC QQWSSNPRT FGQGTKLEIK
hSB-9C2-L2   GIPARFSGSGSGTDFTLTISSLEPEDFAVYYC QQWSSNPRT FGQGTKLEIK
hSB-9C2-L3   GIPARFSGSGSGTDFTLTISSLEPEDFAVYYC QQWSSNPRT FGQGTKLEIK
hSB-9C2-L4   GVPARFSGSGSGTDFTLTISSVEPEDFAVYYC QQWSSNPRT FGQGTKLEIK
                   A                                     #
```

Figure 15A
Figure 15B
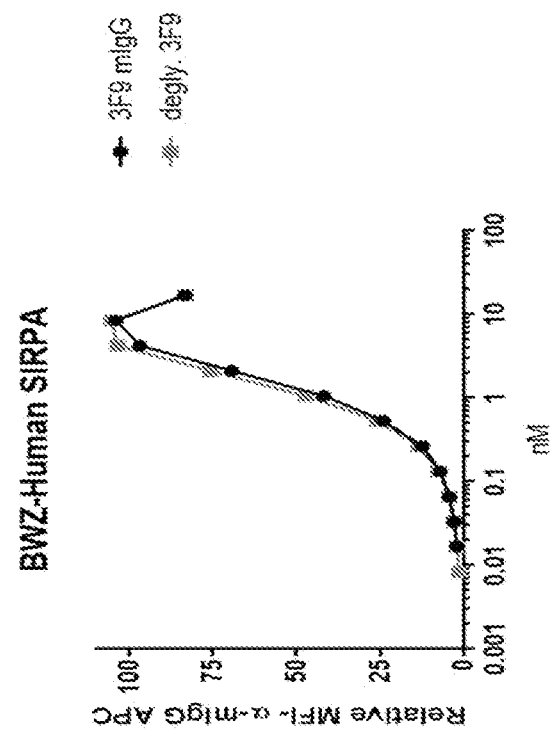
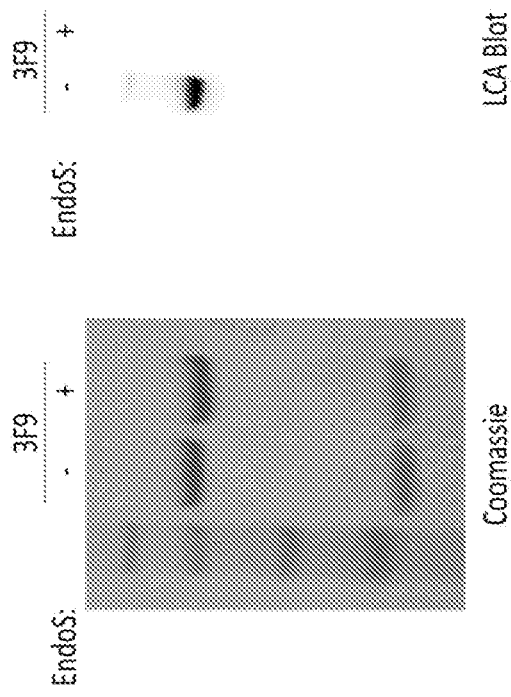

ANTI-SIRP-ALPHA ANTIBODIES AND METHODS OF USE THEREOF

CROSS REFERENCE TO RELATED APPLICATIONS

This application is a national phase entry pursuant to 35 U.S.C. § 371 of International Application No. PCT/US2017/065366, filed Dec. 8, 2017, which claims the benefit of priority of U.S. Provisional Application No. 62/432,503, filed Dec. 9, 2016, each of which is hereby incorporated by reference herein in its entirety.

SUBMISSION OF SEQUENCE LISTING ON ASCII TEXT FILE

The content of the following submission of ASCII text file is incorporated herein by reference in its entirety: a computer readable form (CRF) of the Sequence Listing, file name 099061-1069197_SL.TXT, 70,619 bytes, created Dec. 7, 2017.

FIELD OF THE INVENTION

This invention relates to anti-SIRPA antibodies and therapeutic uses of such antibodies.

BACKGROUND OF THE INVENTION

Phagocytic cells, such as macrophages (MΦ) and dendritic cells (DCs), distinguish healthy from abnormal cells through an intricate array of cell surface receptors that modulate cellular activation status, proliferation, and/or effector functions. Many of these receptors recognize diverse ligands that either mark unwanted cells for removal (so-called "eat-me" signals) or protect normal cells from destruction (so called "don't-eat-me" signals). In recent years, the SIRPα-CD47 axis has emerged as a critical determinant in programmed cell removal by macrophages in various clinical settings ranging from cancer cell survival to successful engraftment of hematopoietic cell transplantation. Therapeutic agents that impact this pathway may meet a relevant medical need to ameliorate disease with particular relevance in many types of human cancers.

SIRPα (signal regulatory protein-α, SIRPA) belongs to the SIRP family of transmembrane receptors, which are primarily expressed within the myeloid cell lineage (including MΦ, DCs, granulocytes, etc.) and characterized by an extracellular region containing 2 membrane-proximal IgC domains and a distal IgV domain. Unique among this family, SIRPA contains an intracellular, cytoplasmic immunoreceptor tyrosine-based inhibitory motif (ITIM). Upon receptor cross-linking, tyrosine-phosphorylated ITIM sites recruit and activate SHP phosphatases to negatively regulate cellular functions, such as phagocytosis or inflammatory cytokine release. CD47 serves as the principal ligand for SIRPA, and its broad expression in most cell types, including endothelial/epithelial cells, leukocytes, and erythrocytes, suggests that it mediates a "don't-eat-me" signal to protect healthy cells from phagocyte-dependent clearance. In support of this view, several studies show that adoptive transfer of red blood cells or leukocytes from CD47-knockout mice into wild-type recipients results in rapid clearance of CD47-deficient cells. Conversely, positional genetic analysis of multiple strains of immune-compromised mice receiving human hematopoietic cells identified the Sirpα allele in NOD mice as the causal factor for successful engraftment in xenotransplantation models. Subsequent studies demonstrated that the allelic variant of SIRPA expressed only in NOD mice retained the ability to bind human CD47 expressed on human hematopoietic stem cells, and thus, suppress macrophage-dependent graft rejection.

Regulated expression of SIRPA and CD47 establishes a homeostatic control mechanism to modulate phagocytic cell activity. For example, apoptotic cells downregulate expression of CD47 to facilitate engulfment by resident macrophages while live cells remain unharmed. Likewise, inflammatory stimuli, such as LPS, decrease SIRPA expression in MΦ and DCs to potentiate their activation during inflammation. However, dysregulation of SIRPA and CD47 expression contributes to immune-associated diseases, as seen in cancer. Several tumors significantly augment expression of CD47 relative to non-cancerous cells in order to evade immune surveillance mechanisms that normally eliminate malignant cells. Preclinical studies reveal that genetic knockdown of CD47 in syngeneic tumor models, such as B16F10 melanoma, is sufficient to inhibit tumor growth in immune-competent mice. Similar results have been observed with CD47-knocked down human cancer cell lines transplanted into immune-compromised mice. Alternatively, biologic agents that disrupt SIRPA-CD47 interaction, such as anti-CD47 antibodies, also enhance tumor clearance in mouse models. When combined with commercial anti-tumor antigen antibodies, such as trastuzumab or rituximab, anti-CD47 antibodies facilitate a synergistic increase in the anti-tumor response compared to standard monotherapy. Yet, given the ubiquitous expression of CD47, anti-CD47 antibodies risk severe toxicity burdens due to off-target effects limiting their therapeutic efficacy. Nevertheless, these studies establish a crucial role for the SIRPA-CD47 pathway in regulating myeloid cells with potential applications in cancer immunotherapy.

BRIEF SUMMARY OF ASPECTS OF THE DISCLOSURE

In certain aspects, the present disclosure provides agents that down-regulate SIRPA, e.g., anti-SIRPA antibodies. Such agents can be used for treating, preventing, or reducing risk of a disease or pathology associated with SIRPA expression, activity, or signaling. In some aspects, the disclosure relates to the identification of anti-SIRPA antibodies that are capable of downregulating, i.e., decreasing levels of, SIRPA on human macrophages and dendrocytes, as well as cell lines that express SIRPA. In some aspects, the disclosure relates to anti-SIRPA antibodies that antagonize the immune suppressive SIRPA-CD47 interaction and facilitate phagocytosis of CD47-expressing tumor cells. In a further aspect, the present disclosure provides unique SIRPA-specific antibodies that disrupt CD47 binding through non-competitive inhibition.

Thus, in one aspect, the disclosure relates to a SIRPA antibody that selectively binds SIRPA and down-regulates SIRPA expressed on the cell surface. In some embodiments, the anti-SIRPA antibody decreases cell surface levels of SIRPA, decreases intracellular levels of SIRPA, decreases total levels of SIRPA, or any combination thereof. In some embodiments, which may be combined with any of the preceding embodiments, the anti-SIRPA antibody induces SIRPA degradation, SIRPA cleavage, SIRPA internalization, SIRPA shedding, downregulation of SIRPA expression, or any combination thereof. In some embodiments, which may be combined with any of the preceding embodiments, the antibody decreases cellular levels of SIRPA in vivo. In some embodiments that may be combined with any of the preceding embodiments, the anti-SIRPA antibody inhibits cell surface clustering of SIRPA. In further embodiments that may be combined with any of the preceding embodiments, the anti-SIRPA antibody inhibits one or more SIRPA activities; or counteracts, one or more SIRPA activities, which may be selected from the group consisting of: (a) SIRPA binding to one or more SIRPA ligands, optionally wherein the one or more SIRPA ligands are selected from the group consisting of CD47, surfactant protein A and D and any combination thereof; (b) decreasing proliferation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (c) inhibiting migration of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (d) inhibiting one or more functions of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (e) inhibition of one or more types of clearance selected from the group consisting of apoptotic neuron clearance, nerve tissue debris clearance, dysfunctional synapse clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; (f) inhibition of tumor cell killing by one or more of microglia, macrophages, neutrophils, NK cells, dendritic cells, bone marrow-derived dendritic cells, neutrophils, T cells, T helper cells, or cytotoxic T cells; (g) inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; (h) modulated expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; (i) promoting or rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; (j) increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, non-tumorigenic CD45+CD14+ myeloid cells, and regulatory T cells into tumors; (k) increasing the number of tumor-promoting myeloid/granulocytic immune-suppressive cells and/or non-tumorigenic CD45+CD14+ myeloid cells in a tumor, in peripheral blood, or other lymphoid organ; (l) enhancing tumor-promoting activity of myeloid-derived suppressor cells and/or non-tumorigenic CD45+CD14+ myeloid cells; (m) enhancing survival of non-tumorigenic myeloid-derived suppressor cells and/or non-tumorigenic CD45+CD14+ myeloid cells; (n) decreasing activation of tumor-specific T lymphocytes with tumor killing potential; (o) decreasing infiltration of tumor-specific NK cells with tumor killing potential; (p) increasing tumor volume; (q) increasing tumor growth rate; and (r) decreasing efficacy of one or more immune-therapies that modulate anti-tumor T cell responses, optionally wherein the one or more immune-therapies are immune-therapies that target one or more target proteins selected from the group consisting of PD1/PDL1, CD40, OX40, ICOS, CD28, CD137/4-1BB, CD27, GITR, PD-L1, CTLA4, PD-L2, PD-1, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, TREM1, TREM2, CD39, CD73, CSF-1 receptor, and any combination thereof, or of one or more cancer vaccines. In some embodiments that may be combined with any of the preceding embodiments, the anti-SIRPA antibody induces one or more of the activities that are selected from the group consisting of: (a) increasing the number of tumor infiltrating CD3+ T cells; (b) decreasing cellular levels of SIRPA in non-tumorigenic CD14+myeloid cells, optionally wherein the non-tumorigenic CD14+ myeloid cells are tumor infiltrating cells or optionally wherein the non-tumorigenic CD14+ myeloid cells are present in blood; (c) reducing the number of non-tumorigenic CD14+ myeloid cells, optionally wherein the non-tumorigenic CD14+ myeloid cells are tumor infiltrating cells or optionally wherein the non-tumorigenic CD14+ myeloid cells are present in blood; (d) reducing PD-L1 levels in one or more cells, optionally wherein the one or more cells are non-tumorigenic myeloid-derived suppressor cells (MDSC); (e) reducing PD-L2 levels in one or more cells, optionally wherein the one or more cells are non-tumorigenic myeloid-derived suppressor cells (MDSC); (f) reducing B7-H2 levels in one or more cells, optionally wherein the one or more cells are non-tumorigenic myeloid-derived suppressor cells (MDSC); (g) reducing B7-H3 levels in one or more cells, optionally wherein the one or more cells are non-tumorigenic myeloid-derived suppressor cells (MDSC); (h) reducing CD200R levels in one or more cells, optionally wherein the one or more cells are non-tumorigenic myeloid-derived suppressor cells (MDSC); (i) reducing CD163 levels in one or more cells, optionally wherein the one or more cells are non-tumorigenic myeloid-derived suppressor cells (MDSC); (j) reducing CD206 levels in one or more cells, optionally wherein the one or more cells are non-tumorigenic myeloid-derived suppressor cells (MDSC); (k) decreasing tumor growth rate of solid tumors; (l) reducing tumor volume; (m) increasing efficacy of one or more PD-1 inhibitors; (n) increasing efficacy of one or more checkpoint inhibitor therapies and/or immune-modulating therapies, optionally wherein the one or more checkpoint inhibitor therapies and/or immune-modulating therapies target one or more of CTLA4, the adenosine pathway, PD-L1, PD-L2, OX40, TIM3, LAG3, or any combination thereof; (o) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (p) increasing proliferation of T cells in the presence of non-tumorigenic myeloid-derived suppressor cells (MDSC); (l) inhibiting differentiation, survival, and/or one or more functions of non-tumorigenic myeloid-derived suppressor cells (MDSC); and (r) killing CD33-expressing immunosuppressor non-tumorigenic myeloid cells and/or non-tumorigenic CD14-expressing cells in solid tumors and associated blood vessels when conjugated to a chemical or radioactive toxin.

In some embodiments, which may be combined with any of the preceding embodiments, the anti-SIRPA antibody inhibits interaction between SIRPA and one or more SIRPA ligands. In some embodiments, which may be combined with any of the preceding embodiments, the anti-SIRPA antibody decreases cellular levels of SIRPA and inhibits interaction between SIRPA and one or more SIRPA ligands. In some embodiments, which may be combined with any of the preceding embodiments, the anti-SIRPA antibody blocks binding of CD47 to human SIRPA.

In some embodiments, which may be combined with any of the preceding embodiments, the antibody selectively binds human SIRPA and does not substantially block binding of CD47 binding to human SIRPA expressed on cells and further, wherein binding to human SIRPA decreases the level of SIRPA on the cell surface. In some embodiments, the antibody binds to the D1 domain of SIRPA, e.g., human SIRPA. In some embodiments, the antibody binds to the D2 domain of SIRPA e.g., human SIRPA. In some embodiments, the antibody binds to the D3 domain of SIRPA, e.g., human SIRPA. In some embodiments, such an anti-SIRPA antibody competes with an antibody comprising a $V_H$ sequence comprising the amino acid sequence of SEQ ID NO:2 and a $V_L$ sequence comprising the amino acid sequence of SEQ ID NO:3. In some embodiments, such an anti-SIRPA antibody comprises a $V_H$ region comprising: a CDR3 comprising the amino acid sequence of SEQ ID NO:11, a CDR1 comprising the amino acid sequence of SEQ ID NO:9, or a CDR2 comprising the amino acid sequence of SEQ ID NO:10. In some embodiments, the anti-SIRPA antibody comprises a $V_H$ region comprising: a) a CDR1 that comprises the amino acid sequence of SEQ ID NO:9, a CDR1 that comprises the amino acid sequence of SEQ ID NO:9 with no more than two amino acid substitutions, or a CDR1 having at least about 90% identity to the amino acid sequence of SEQ ID NO:9; (b) a CDR2 that comprises the amino acid sequence of SEQ ID NO:10 or a CDR2 that comprises the amino acid sequence of SEQ ID NO:10 with no more than two amino acid substitutions; or a CDR2 having at least about 90% identity to the amino acid sequence of SEQ ID NO:10; and (c) a CDR3 that comprises the amino acid sequence of SEQ ID NO:11, a CDR3 that comprises the amino acid sequence of SEQ ID NO:11 with no more than two amino acid substitutions; or a CDR3 having at least about 90% identity to the amino acid sequence of SEQ ID NO:11. In some embodiments, the anti-SIRPA comprises a $V_H$ region comprising: a CDR1 comprising the amino acid sequence of SEQ ID NO:9 or a CDR1 comprising the amino acid sequence of SEQ ID NO:9 with no more than one amino acid substitution; a CDR2 comprising the amino acid sequence of SEQ ID NO:10 or a CDR2 comprising the amino acid sequence of SEQ ID NO:10 with no more than one amino acid substitution; and a CDR3 comprising the amino acid sequence of SEQ ID NO:11 or a CDR3 comprising the amino acid sequence of SEQ ID NO:11 with no more than one amino acid substitution. In some embodiments, the anti-SIRPA antibody comprises a $V_H$ region that comprises a CDR1 comprising the amino acid sequence of SEQ ID NO:9, a CDR2 comprising the amino acid sequence of SEQ ID NO:10, and a CDR3 comprising the amino acid sequence of SEQ ID NO:11. In some embodiments that may be combined with any of the preceding embodiments, the antibody comprises a $V_H$ region comprising the amino acid sequence of a $V_H$ region shown in FIG. 14A or comprises a $V_H$ region having at least 90%, at least 91%, at least 92%, at least 93%, at least 94%, at least 95%, at least 96%, at least 97%, at least 98%, or at least 99% sequence identity to the amino acid sequence of a $V_H$ region of FIG. 14A. In some embodiments, which may be combined with any of the preceding embodiments, the anti-SIRPA antibody comprises a $V_L$ region that comprises a CDR3 comprising the amino acid sequence of SEQ ID NO:8, a CDR1 comprising the amino acid sequence of SEQ ID NO:6, or a CDR2 comprising the amino acid sequence of SEQ ID NO:7. In some embodiments, the $V_L$ region comprises: (a) a CDR1 comprising the amino acid sequence of SEQ ID NO:6, a CDR1 comprising the amino acid sequence of SEQ ID NO:6 with no more than two amino acid substitutions, or a CDR1 having at least about 90% identity to the amino acid sequence of SEQ ID NO:6; (b) a CDR2 comprising the amino acid sequence of SEQ ID NO:7, a CDR2 comprising the amino acid sequence of SEQ ID NO:7 with no more than two amino acid substitutions, or a CDR2 having at least about 90% identity to the amino acid sequence of SEQ ID NO:7; and (c) a CDR3 comprising the amino acid sequence of SEQ ID NO:8, a CDR3 comprising the amino acid sequence of SEQ ID NO:8 with no more than two amino acid substitutions, or a CDR3 having at least about 90% identity to the amino acid sequence of SEQ ID NO:8. In some embodiments, the $V_L$ region comprises a CDR1 comprising the amino acid sequence of SEQ ID NO:6 or a CDR1 comprising the amino acid sequence of SEQ ID NO:6 with no more than one amino acid substitution; a CDR2 comprising the amino acid sequence of SEQ ID NO:7 or a CDR2 comprising the amino acid sequence of SEQ ID NO:7 with no more than one amino acid substitution; and a CDR3 comprising the amino acid sequence of SEQ ID NO:8 or a CDR3 comprising the amino acid sequence of SEQ ID NO:8 with no more than one amino acid substitution. In some embodiments, the $V_L$ region comprises a CDR1 comprising the amino acid sequence of SEQ ID NO:6, a CDR2 comprising the amino acid sequence of SEQ ID NO:7, and a CDR3 comprising the amino acid sequence of SEQ ID NO:8. In some embodiments, which may be combined with any of the preceding embodiments, the $V_L$ region comprises the amino acid sequence of a $V_L$ region shown in FIG. 14B; or comprises a $V_L$ region having at least 90%, at least 91%, at least 92%, at least 93%, at least 94%, at least 95%, at least 96%, at least 97%, at least 98%, or at least 99% sequence identity to the amino acid sequence of a $V_L$ region of FIG. 14B. In some embodiments, the antibody comprises an Fc region that decreases the levels of FcγR expressed on the surface of cells. In some embodiments, the antibody comprises an Fc region that decreases the levels of FcγRBII on the surface of cells.

In some embodiments, which may be combined with any of the preceding embodiments, the antibody selectively binds human SIRPA, but not murine SIRPA, and does not substantially block binding of CD47 binding to human SIRPA expressed on cells and further, wherein binding to human SIRPA decreases the level of SIRPA on the cell surface. In some embodiments, such an anti-SIRPA antibody competes with an antibody comprising a $V_H$ sequence comprising the amino acid sequence of SEQ ID NO:2 and a $V_L$ sequence comprising the amino acid sequence of SEQ ID NO:3. In some embodiments, the antibody binds to the D1 domain of SIRPA, e.g., human SIRPA. In some embodiments, the antibody binds to the D2 domain of SIRPA e.g., human SIRPA. In some embodiments, the antibody binds to the D3 domain of SIRPA, e.g., human SIRPA. In some embodiments, the anti-SIRPA antibody comprises a $V_H$ region that comprises a CDR3 comprising the amino acid sequence of SEQ ID NO:17, a CDR1 comprising the amino acid sequence of SEQ ID NO:15, or a CDR2 comprising the amino acid sequence of SEQ ID NO:16. In some embodiments, the $V_H$ region comprises: a) a CDR1 comprising the amino acid sequence of SEQ ID NO:15, a CDR1 comprising the amino acid sequence of SEQ ID NO:15 with no more than two amino acid substitutions, or a CDR1 having at least about 90% identity to the amino acid sequence of SEQ ID NO:15; (b) a CDR2 comprising the amino acid sequence of SEQ ID NO:16, a CDR2 comprising the amino acid sequence of SEQ ID NO:16 with no more than two amino acid substitutions, or a CDR2 having at least about 90% identity to the amino acid sequence of SEQ ID NO:16; and (c) a CDR3 comprising the amino acid sequence of SEQ ID NO:17, a CDR3 comprising the amino acid sequence of SEQ ID NO:17 with no more than two amino acid substitutions, or a CDR3 having at least about 90% identity to the amino acid sequence of SEQ ID NO:17. In some embodiments, the $V_H$ region comprises a CDR1 comprising the amino acid sequence of SEQ ID NO:15 or a CDR1 comprising the amino acid sequence of SEQ ID NO:15 with no more than one amino acid substitution; a CDR2 comprising the amino acid sequence of SEQ ID NO:16 or a CDR2 comprising the amino acid sequence of SEQ ID NO:16 with no more than one amino acid substitution; and a CDR3 comprising the amino acid sequence of SEQ ID NO:16 or a CDR3 comprising the amino acid sequence of SEQ ID NO:16 with no more than one amino acid substitution. In some embodiments, the $V_H$ region comprises a CDR1 comprising the amino acid sequence of SEQ ID NO:15, a CDR2 comprising the amino acid sequence of SEQ ID NO:16, and a CDR3 comprising the amino acid sequence of SEQ ID NO:17. In some embodiments, which may be combined with any of the preceding embodiments, the antibody comprises a $V_H$ region that comprises the amino acid sequence of a $V_H$ region of FIG. 14C; or comprises a $V_H$ region having at least 90%, at least 91%, at least 92%, at least 93%, at least 94%, at least 95%, at least 96%, at least 97%, at least 98%, or at least 99% sequence identity to the amino acid sequence of a $V_H$ region of FIG. 14C. In some embodiments, which may be combined with any of the preceding embodiments, the $V_L$ region comprises a CDR3 comprising the amino acid sequence of SEQ ID NO:14, a CDR1 comprising the amino acid sequence of SEQ ID NO:12, or a CDR2 comprising the amino acid sequence of SEQ ID NO:13. In some embodiments, the $V_L$ region comprises: a) a CDR1 comprising the amino acid sequence of SEQ ID NO:12, a CDR1 comprising the amino acid sequence of SEQ ID NO:12 with no more than two amino acid substitutions, or a CDR1 having at least about 90% identity to the amino acid sequence of SEQ ID NO:12; (b) a CDR2 comprising the amino acid sequence of SEQ ID NO:13, a CDR2 comprising the amino acid sequence of SEQ ID NO:13 with no more than two amino acid substitutions, or a CDR2 having at least about 90% identity to the amino acid sequence of SEQ ID NO:13; and (c) a CDR3 comprising the amino acid sequence of SEQ ID NO:14, a CDR3 comprising the amino acid sequence of SEQ ID NO:14 with no more than two amino acid substitutions, or a CDR3 having at least about 90% identity to the amino acid sequence of SEQ ID NO:14. In some embodiments, the $V_L$ region comprises a CDR1 comprising the amino acid sequence of SEQ ID NO:12 or a CDR1 comprising the amino acid sequence of SEQ ID NO:12 with no more than one amino acid substitution; a CDR2 comprising the amino acid sequence of SEQ ID NO:13 or a CDR2 comprising the amino acid sequence of SEQ ID NO:13 with no more than one amino acid substitution; and a CDR3 comprising the amino acid sequence of SEQ ID NO:4 or a CDR3 comprising the amino acid sequence of SEQ ID NO:14 with no more than one amino acid substitution. In some embodiments, the $V_L$ region comprises a CDR1 comprising the amino acid sequence of SEQ ID NO:6, a CDR2 comprising the amino acid sequence of SEQ ID NO:7, and a CDR3 comprising the amino acid sequence of SEQ ID NO:8. In some embodiments, which may be combined with any of the preceding embodiments, the $V_L$ region comprises the amino acid sequence of a $V_L$ region of FIG. 14D; or comprises a $V_L$ region having at least 90%, at least 91%, at least 92%, at least 93%, at least 94%, at least 95%, at least 96%, at least 97%, at least 98%, or at least 99% sequence identity to the amino acid sequence of a $V_L$ region of FIG. 14D. In some embodiments, the antibody comprises an Fc region that decreases levels of FcγR on the surface of cells. In some embodiments, the antibody comprises an Fc region that decreases levels of FcγRBII on the surface of cells.

In a further aspect, which may be combined with any of the preceding embodiments, an isolated anti-SIRPA of the present disclosure competes with one or more antibodies selected from the group consisting of 3F9, 9C2, 8A9, 8F4, 1E2, 7H9, and 4D8 for binding to SIRPA. In some embodiments, the antibody binds to the D1 domain of SIRPA, e.g., human SIRPA. In some embodiments, the antibody binds to the D2 domain of SIRPA e.g., human SIRPA. In some embodiments, the antibody binds to the D3 domain of SIRPA, e.g., human SIRPA. In some embodiments, the isolated anti-SIRPA antibody binds to essentially the same epitope as one or more antibodies selected from the group consisting of 3F9, 9C2, 8A9, 8F4, 1E2, 7H9, and 4D8. In some embodiments, the isolated anti-SIRPA antibody comprises a V$_H$ region and a V$_L$ region, wherein the V$_H$ region, the V$_L$ region, or both, comprise at least one, two, three, four, five, or six CDRs of a monoclonal antibody selected from the group consisting of 3F9, 9C2, 8A9, 8F4, 1E2, 7H9, and 4D8.

In some embodiments, which may be combined with any of the preceding embodiments, the anti-SIRPA antibody is a monoclonal antibody. In some embodiments, which may be combined with any of the preceding embodiments, the anti-SIRPA antibody is a humanized antibody. In some embodiments, which may be combined with any of the preceding embodiments, the anti-SIRPA antibody is an Fab, Fab', Fab'-SH, F(ab')$_2$, Fv or scFv fragment; or a multivalent antibody, an antibody is of the IgG class, the IgM class, or the IgA class.

In some embodiments that may be combined with any of the preceding embodiments, the anti-SIRPA antibody is of the IgG class the IgM class, or the IgA class. In some embodiments that may be combined with any of the preceding embodiments, the anti-SIRPA antibody has an IgG1, IgG2, IgG3, or IgG4 isotype. In some embodiments that may be combined with any of the preceding embodiments, the antibody binds an inhibitory Fc receptor. In some embodiments that may be combined with any of the preceding embodiments, the inhibitory Fc receptor is inhibitory Fc-gamma receptor IIB (FcγRIIB). In some embodiments, the antibody decreases the level of FcγRIIB on the cell surface. In some embodiments that may be combined with any of the preceding embodiments: (a) the anti-SIRPA antibody has a human or mouse IgG1 isotype and comprises one or more amino acid substitutions in the Fc region at a residue position selected from the group consisting of: N297A, D265A, D270A, L234A, L235A, G237A, P238D, L328E, E233D, G237D, H268D, P271G, A330R, C226S, C229S, E233P, L234V, L234F, L235E, P331S, S267E, L328F, A330L, M252Y, S254T, T256E, N297Q, P238S, P238A, A327Q, A327G, P329A, K322A, T394D, and any combination thereof, wherein the numbering of the residues is according to EU or Kabat numbering, or comprises an amino acid deletion in the Fc region at a position corresponding to glycine 236; (b) the anti-SIRPA antibody has an IgG1 isotype and comprises an IgG2 isotype heavy chain constant domain 1(CH1) and hinge region, optionally wherein the IgG2 isotype CH1 and hinge region comprises the amino acid sequence of ASTKGPSVFP LAPCSRSTSE STAAL-GCLVK DYFPEPVTVS WNSGALTSGVHTFPAVLQSS GLYSLSSVVT VPSSNFGTQT YTCNVDHKPS NTKVDKTVERKCCVECPPCP (SEQ ID NO:34), and optionally wherein the antibody Fc region comprises a S267E amino acid substitution, a L328F amino acid substitution, or both, and/or a N297A or N297Q amino acid substitution, wherein the numbering of the residues is according to EU numbering; (c) the anti-SIRPA antibody has an IgG2 isotype and comprises one or more amino acid substitutions in the Fc region at a residue position selected from the group consisting of: P238S, V234A, G237A, H268A, H268Q, V309L, A330S, P331S, C214S, C232S, C233S, S267E, L328F, M252Y, S254T, T256E, H268E, N297A, N297Q, A330L, and any combination thereof, wherein the numbering of the residues is according to EU or Kabat numbering; (d) the anti-SIRPA antibody has a human or mouse IgG4 isotype and comprises one or more amino acid substitutions in the Fc region at a residue position selected from the group consisting of: L235A, G237A, S228P, L236E, S267E, E318A, L328F, M252Y, S254T, T256E, E233P, F234V, L234A/F234A, S228P, S241P, L248E, T394D, N297A, N297Q, L235E, and any combina-tion thereof, wherein the numbering of the residues is according to EU or Kabat numbering; or (e) the anti-SIRPA antibody has a hybrid IgG2/4 isotype, and optionally wherein the antibody comprises an amino acid sequence comprising amino acids 118 to 260 of human IgG2 and amino acids 261 to 447 of human IgG4, wherein the numbering of the residues is according to EU or, Kabat numbering. In some embodiments that may be combined with any of the preceding embodiments: (a) the anti-SIRPA antibody has a human or mouse IgG1 isotype and comprises one or more amino acid substitutions in the Fc region at a residue position selected from the group consisting of: N297A, N297Q, D270A, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof, wherein the numbering of the residues is according to EU or Kabat numbering; (b) the anti-SIRPA antibody has an IgG2 isotype and comprises one or more amino acid substitutions in the Fc region at a residue position selected from the group consisting of: P238S, V234A, G237A, H268A, H268Q, H268E, V309L, N297A, N297Q, A330S, P331S, C232S, C233S, M252Y, S254T, T256E, and any combination thereof, wherein the numbering of the residues is according to EU or Kabat numbering; or (c) the anti-SIRPA antibody has an IgG4 isotype and comprises one or more amino acid substitutions in the Fc region at a residue position selected from the group consisting of: E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU or Kabat numbering. In some embodiments that may be combined with any of the preceding embodiments: (a) the Fc region further comprises one or more additional amino acid substitutions at a position selected from the group consisting of A330L, L234F; L235E, P331S, and any combination thereof, wherein the numbering of the residues is according to EU or Kabat numbering; (b) the Fc region further comprises one or more additional amino acid substitutions at a position selected from the group consisting of M252Y, S254T, T256E, and any combination thereof, wherein the numbering of the residues is according to EU or Kabat numbering; or (c) the Fc region further comprises a S228P amino acid substitution according to EU or Kabat numbering. In some embodiments that may be combined with any of the preceding embodiments, the antibody has an IgG4 isotype. In some embodiments that may be combined with any of the preceding embodiments, the anti-SIRPA antibody comprises an S228P amino acid substitution at residue position 228, an F234A amino acid substitution at residue position 234, and an L235A amino acid substitution at residue position 235, wherein the numbering of the residue position is according to EU or Kabat numbering.

In some embodiments, which may be combined with any of the preceding embodiments, the anti-SIRPA antibody is a bispecific antibody. In some embodiments, the anti-SIRPA antibody recognizes a first and a second antigen, wherein the first antigen is SIRPA and the second antigen is: (a) an antigen facilitating transport across the blood-brain-barrier; (b) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing agent selected from the group consisting of disease-causing peptides or proteins or, disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; and (d) ligands and/or proteins expressed on immune cells, wherein the ligands and/or proteins selected from the group consisting of PD1/PDL1, CD40, OX40, ICOS, CD28, CD137/4-1BB, CD27, GITR, PD-L1, CTLA4, PD-L2, PD-1, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, CD73, and phosphatidylserine; and a protein, lipid, polysaccharide, or glycolipid expressed on one or more tumor cells.

In some embodiments, which may be combined with any of the preceding embodiments, the anti-SIRPA antibody is a conjugated antibody. For example, the anti-SIRPA antibody may be conjugated to a detectable marker, a toxin, or a therapeutic agent. In some embodiments, the anti-SIRPA antibody is conjugated to a toxin selected from the group consisting of ricin, ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin.

In further embodiments, which may be combined with any of the preceding embodiments, the anti-SIRPA antibody is used in combination with one or more antibodies that specifically bind a disease-causing protein selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: PD1/PDL1, CD40, OX40, ICOS, CD28, CD137/4-1BB, CD27, GITR, PD-L1, CTLA4, PD-L2, PD-1, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, CD73, TREM1, TREM2, CD33, Siglec-5, Siglec-7, Siglec-9, Siglec-11, phosphatidylserine, disease-causing nucleic acids, antisense GGCCCC (G2C4) repeat-expansion RNA, and any combination thereof.

In a further aspect, the disclosure provides a method of decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof, comprising administering to the individual a therapeutically effective amount of an agent that binds or interacts with SIRPA, e.g., an antibody of any of the embodiments described above.

In an additional aspect, the disclosure provides a method of inducing or promoting the survival, maturation, functionality, migration, or proliferation of one or more immune cells in an individual in need thereof, comprising administering to the individual a therapeutically effective amount of an agent, e.g., an antibody of any of the embodiments described above, that decreases cellular levels of SIRPA, inhibits interaction between SIRPA and one or more SIRPA ligands, or both. In some embodiments, the one or more immune cells are selected from the group consisting of dendritic cells, macrophages, neutrophils, NK cells, microglia, T cells, T helper cells, cytotoxic T cells, and any combination thereof.

In another aspect, the disclosure provides a method of treating cancer, the method comprising administering a therapeutically effective amount of an anti-SIRPA antibody of any of the embodiments described above to a patient that has a tumor the expresses CD47.

In an additional aspect, the invention provides a method of treating cancer, the method comprising administering a therapeutically effective amount of an agent, e.g., an anti-SIRPA antibody of any of the embodiments described above, that decreases the cellular levels of SIRPA. In some embodiments, the method further comprises administering a therapeutic agent that inhibits PD1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, or CD73. In some embodiments, the therapeutic agent is an antibody that inhibits PD1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, or CD73.

In an additional aspect, the invention provides a method of treating cancer, the method comprising administering a therapeutically effective amount of an agent, e.g., an anti-SIRPA antibody of any of the embodiments described above, that decreases the cellular levels of SIRPA. In some embodiments, the method further comprises administering to the individual at least one antibody that specifically binds to an inhibitory checkpoint molecule, and/or one or more standard or investigational anti-cancer therapies. In some embodiments, the at least one antibody that specifically binds to an inhibitory checkpoint molecule is administered in combination with the anti-SIRPA antibody. In some embodiments, the at least one antibody that specifically binds to an inhibitory checkpoint molecule is selected from the group consisting of an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM-1 antibody, an anti-TIM3 antibody, an anti-TIM-4 antibody, an anti-A2AR antibody, an anti-CD39 antibody, an anti-CD73 antibody, an anti-LAG-3 antibody, an anti-phosphatidylserine antibody, an anti-CD27 antibody, an anti-CD30 antibody, an anti-TNFa antibody, an anti-CD33 antibody, an anti-Siglec-5 antibody, an anti-Siglec-7 antibody, an anti-Siglec-9 antibody, an anti-Siglec-11 antibody, an antagonistic anti-TREM1 antibody, an antagonistic anti-TREM2 antibody, an anti-TIGIT antibody, an anti-VISTA antibody, an anti-CD2 antibody, an anti-CD5 antibody, and any combination thereof. In some embodiments, which may be combined with any of the preceding embodiments, the one or more standard or investigational anti-cancer therapies are selected from the group consisting of radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy.

In some embodiments, which may be combined with any of the preceding method embodiments, the method further comprises administering to the individual at least one antibody that specifically binds to an inhibitory cytokine. In some embodiments, the at least one antibody that specifically binds to an inhibitory cytokine is administered in combination with an anti-SIRPA antibody of any one of the preceding embodiments. In some embodiments, the at least one antibody that specifically binds to an inhibitory cytokine is selected from the group consisting of an anti-CCL2 antibody, an anti-CSF-1 antibody, an anti-IL-2 antibody, and any combination thereof. In some embodiments that may be combined with any of the preceding embodiments, the method further comprises administering to the individual at least one agonistic antibody that specifically binds to a stimulatory checkpoint protein. In some embodiments, the at least one agonistic antibody that specifically binds to a stimulatory checkpoint protein is administered in combination with an anti-SIRPA antibody of any of the preceding embodiments. In some embodiments, the at least one agonistic antibody that specifically binds to a stimulatory checkpoint protein is selected from the group consisting of an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, an agonist anti-CD30 antibody, an agonist anti-BTLA antibody, an agonist anti-HVEM antibody, an agonist anti-CD2 antibody, an agonist anti-CD5 antibody, and any combination thereof. In some embodiments, which may be combined with any of the preceding embodiments, the method further comprises administering to the individual at least one stimulatory cytokine. In some embodiments, the stimulatory cytokine is selected from the group consisting of IFN-α4, IFN-β, IL-1β, TNF-α, IL-6, IL-8, CRP, IL-20 family members, LIF, IFN-γ, OSM, CNTF, GM-CSF, IL-11, IL-12, IL-15, IL-17, IL-18, IL-23, CXCL10, IL-33, MCP-1, MIP-1-beta, and any combination thereof.

In a further aspect, the disclosure provides a method of treating cancer, the method comprising administering a therapeutically effective amount of an anti-SIRPA antibody of any one of the preceding embodiments to a subject that has cancer cells of a myeloid lineage that expresses SIRPA.

In another aspect, the disclosure provides a method of treating cancer, the method comprising administering a therapeutically effective amount of an anti-SIRPA antibody of any one of the preceding embodiments to a subject that has a cancer, wherein the cancer is selected from the group consisting of sarcoma, bladder cancer, brain cancer, breast cancer, colon cancer, rectal cancer, endometrial cancer, kidney cancer, renal pelvis cancer, leukemia, lung cancer, melanoma, lymphoma, pancreatic cancer, prostate cancer, ovarian cancer, and fibrosarcoma; or wherein the cancer is selected from the group consisting of glioblastoma multiforme; renal clear cell carcinoma; adrenocortical carcinoma; bladder urothelial carcinoma; diffuse large B-cell lymphoma; lung adenocarcinoma; pancreatic adenocarcinoma, renal cell cancer, non-Hodgkin's lymphoma, acute lymphoblastic leukemia (ALL), acute myeloid leukemia (AML), chronic lymphocytic leukemia (CLL), chronic myeloid leukemia (CML), multiple myeloma, breast invasive carcinoma, cervical squamous cell carcinoma, endocervical adenocarcinoma, cholangiocarcinoma, colon adenocarcinoma, diffuse large B-cell lymphoma, esophageal carcinoma, head and neck squamous cell carcinoma, kidney chromophobe, renal papillary cell carcinoma, lower grade glioma, hepatocellular carcinoma, lung squamous cell carcinoa, mesothelioma, ovarian serous cystadenomcarcinoma, pancreatic adenocarcinoma, pheochromocytoma and paraganglioma, prostate adenocarconimo, rectal adenocarcinoma, cutaneous melanoma, stomach adenocarcinoma, testicular germ cell tumors, thyroid carcinoma, thyumoma, uterine corpus endometrial carcinoma, uternine carcinosarcoma, and uveal melanoma. In some embodiments, the anti-SIRPa antibody is conjugated to a cytotoxic agent and/or induces ADCC.

In some embodiments, the disclosure provides a pharmaceutical composition comprising an anti-SIRPA antibody of any one of the preceding embodiments and a physiologically acceptable carrier. In some embodiments, the disclosure provides an anti-SIRPA antibody of any one of the preceding embodiments for use in the treatment of cancer; and/or for use in a method of preparing a medicament for the treatment of cancer.

In a further aspect, the disclosure provides a method of preventing, reducing risk, or treating a disease, disorder, or injury selected from the group consisting of dementia, frontotemporal dementia, Alzheimer's disease, vascular dementia, mixed dementia, taupathy disease, Parkinon's disease, multiple sclerosis, amyotrophic lateral sclerosis, traumatic brain injury, stroke, frontotemporal dementia, spinal cord injury, Huntington's disease, infections, and cancer comprising administering to an individual in need thereof a therapeutically effective amount of an agent that decreases cellular levels of SIRPA, inhibits interaction between SIRPA and one or more SIRPA ligands, or both. In some embodiments, the disease, disorder, or injury is cancer and wherein the agents inhibits one or more SIRPA activities selected from the group consisting of: (a) promoting proliferation, maturation, migration, differentiation, and/or functionality of one or more of immunosuppressor dendritic cells, immunosuppressor macrophages, immunosuppressor neutrophils, immunosuppressor NK cells, myeloid derived suppressor cells, tumor-associated macrophages, tumor-associated suppressor neutrophils, tumor-associated suppressor NK cells, non-tumorigenic CD14+ myeloid cells, and regulatory T cells; (b) enhancing infiltration of one or more of immunosuppressor dendritic cells, immunosuppressor macrophages, immunosuppressor neutrophils, immunosuppressor NK cells, myeloid derived suppressor cells, tumor-associated macrophages, tumor-associated suppressor neutrophils, tumor-associated suppressor NK cells, and regulatory T cells into tumors; (c) increasing number of tumor-promoting myeloid/granulocytic immune-suppressive cells and/or non-tumorigenic CD14+ myeloid cells in a tumor, in peripheral blood, or other lymphoid organ; (d) enhancing tumor-promoting activity of myeloid-derived suppressor cells (MDSC) and/or non-tumorigenic CD14+ myeloid cells; (e) increasing expression of tumor-promoting cytokines in a tumor or in peripheral blood, optionally wherein the tumor-promoting cytokines are TGF-beta or IL-10; (f) increasing tumor infiltration of tumor-promoting FoxP3+ regulatory T lymphocytes; (g) decreasing activation of tumor-specific T lymphocytes with tumor killing potential; (h) decreasing infiltration of tumor-specific T lymphocytes with tumor killing potential; (i) decreasing infiltration of tumor-specific NK cells with tumor killing potential; (j) decreasing the tumor killing potential of NK cells; (k) decreasing infiltration of tumor-specific B lymphocytes with potential to enhance immune response; (l) increasing tumor volume; (m) increasing tumor growth rate; (n) increasing metastasis; (o) increasing rate of tumor recurrence; (p) decreasing efficacy of one or more immune-therapies that modulate anti-tumor T cell responses, optionally wherein the one or more immune-therapies are immune-therapies that target one or more target proteins selected from the group consisting of PD1/PDL1, CD40, OX40, ICOS, CD28, CD137/4-1BB, CD27, GITR, PD-L1, CTLA4, PD-L2, PD-1, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, CD73, and any combination thereof, or one or more cancer vaccines; (q) inhibition of PLCγ/PKC/calcium mobilization; and (r) inhibition of PI3K/Akt, Ras/MAPK signaling. In some embodiments, which may be combined with any of the preceding embodiments, the disease, disorder, or injury is cancer, and wherein the agent exhibits one or more SIRPA activities selected from the group consisting of: (a) increasing the number of tumor infiltrating CD3+ T cells; (b) decreasing cellular levels of CD33 in non-tumorigenic CD14+ myeloid cells, optionally wherein the non-tumorigenic CD14+ myeloid cells are tumor infiltrating cells or optionally wherein the non-tumorigenic CD14+ myeloid cells are present in blood; (c) reducing the number of non-tumorigenic CD14+ myeloid cells, optionally wherein the non-tumorigenic CD14+ myeloid cells are tumor infiltrating cells or optionally wherein the non-tumorigenic CD14+ myeloid cells are present in blood; (d) reducing PD-L1 levels in one or more cells, optionally wherein the one or more cells are non-tumorigenic myeloid-derived suppressor cells (MDSC); (e) reducing PD-L2 levels in one or more cells, optionally wherein the one or more cells are non-tumorigenic myeloid-derived suppressor cells (MDSC); (f) reducing B7-H2 levels in one or more cells, optionally wherein the one or more cells are non-tumorigenic myeloid-derived suppressor cells (MDSC); (g) reducing B7-H3 levels in one or more cells, optionally wherein the one or more cells are non-tumorigenic myeloid-derived suppressor cells (MDSC); (h) reducing CD200R levels in one or more cells, optionally wherein the one or more cells are non-tumorigenic myeloid-derived suppressor cells (MDSC); (i) reducing CD163 levels in one or more cells, optionally wherein the one or more cells are non-tumorigenic myeloid-derived suppressor cells (MDSC); (j) reducing CD206 levels in one or more cells, optionally wherein the one or more cells are non-tumorigenic myeloid-derived suppressor cells (MDSC); (k) decreasing tumor growth rate of solid tumors; (l) reducing tumor volume; (m) increasing efficacy of one or more PD-1 inhibitors; (n) increasing efficacy of one or more checkpoint inhibitor therapies and/or immune-modulating therapies, optionally wherein the one or more checkpoint inhibitor therapies and/or immune-modulating therapies target one or more of CTLA4, the adenosine pathway, PD-L1, PD-L2, OX40, TIM3, LAG3, or any combination thereof; (o) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (p) increasing proliferation of T cells in the presence of non-tumorigenic myeloid-derived suppressor cells (MDSC); (q) inhibiting differentiation, survival, and/or one or more functions of non-tumorigenic myeloid-derived suppressor cells (MDSC); and (r) killing CD33-expressing immunosuppressor myeloid cells and/or CD14-expressing cells in solid tumors and associated blood vessels when conjugated to a chemical or radioactive toxin. In some embodiments, the cancer expresses SIRPA or one or more SIRPA ligands.

In a further aspect, the disclosure provides a method of treating, preventing or decreasing risk of a disease, disorder, or injury, comprising an agent that down-regulates SIRPA, wherein the disease, disorder, or injury is selected from the group consisting of dementia, frontotemporal dementia, Alzheimer's disease, vascular dementia, mixed dementia, taupathy disease, Parkinon's disease, multiple sclerosis, amyotrophic lateral sclerosis, traumatic brain injury, stroke, frontotemporal dementia, spinal cord injury, and Huntington's disease. In some embodiments, the agent is an anti-SIRPA antibody, e.g., of any one of the preceding embodiments, that downregulates SIRPA.

In a further aspect, the disclosure provides: a polynucleotide comprising a nucleic acid sequence encoding a $V_H$ region of an anti-SIRPA antibody of any one of the embodiments described herein; and/or a polynucleotide comprising a nucleic acid sequence encoding a $V_L$ region of an anti-SIRPA antibody of any one of the embodiments described herein. In a further embodiment, the disclosure provides an expression vector comprising the polynucleotide comprising the nucleic acid sequence encoding the $V_H$ region or an expression vector comprising the polynucleotide comprising the nucleic acid sequence encoding the $V_L$ region. In some embodiments, the disclosure provides an expression vector that comprises the polynucleotide encoding the $V_H$ region and the polynucleotide encoding the $V_L$ region. In an additional aspect, the disclosure provides a host cell comprising the polynucleotide comprising the nucleic acid sequence encoding the $V_H$ region or host cell comprising the polynucleotide comprising the nucleic acid sequence encoding the $V_L$ region. In some embodiments, the disclosure provides a host cell that comprises the polynucleotide encoding the $V_H$ region and the polynucleotide encoding the $V_L$ region. In some embodiments, the disclosure provides a host cell comprising an expression vector of any one of the preceding embodiments. In a further aspect, the disclosure provides a method of producing an anti-SIRPA antibody, the method comprising culturing a host cell of any of the preceding embodiments under conditions in which the antibody is expressed. In some embodiments, the host cell is a mammalian host cell.

BRIEF DESCRIPTION OF THE DRAWINGS

FIG. 1A shows an amino acid sequence alignment between the two most common alleles of human SIRPA protein (v1 (SEQ ID NO:1 and v2 (SEQ ID NO:45)) depicting the divergent residues within the ligand-binding domain. Accession numbers are NP542970 and CAA71403, respectively.

FIG. 1B shows an amino acid sequence alignment between the human SIRPA v1 protein (SEQ ID NO:1) and the human SIRPB1 protein (SEQ ID NO:46), depicting the homology between the two proteins. Accession numbers are NP542970 and O00241, respectively.

FIG. 2 shows an amino acid sequence alignment between the human SIRPA protein (SEQ ID NO:1) and the mouse SIRPA protein (SEQ ID NO:47), depicting the homology between the two proteins. Accession numbers are NP542970 and Q6P6I8, respectively.

FIG. 13B plots mean tumor volume in humanized NSG mice by huCD34+ stem cell donor. The top panels of FIG. 13B show mean tumor volume from treatment and control mice engrafted with stem cells from donors 5031 and 5048. The bottom panels of FIG. 13B show mean tumor volume from treatment and control mice engrafted with stem cells from donor 129. Solid gray line represents mean tumor volume of isotype control-treated mice, solid black line represents mean tumor volume of Keytruda-treated mice, and dashed black line represents mean tumor volume of 3F9-treated mice.

FIG. 14A lists potential humanized sequences of the heavy chain variable domain of 3F9. Humanized sequence is based on IGHV3-23*01 acceptor framework and IGHJ4*01 joining region. FIG. 14A discloses SEQ ID NOS 48-53, respectively, in order of appearance.

FIG. 14B lists potential humanized sequences of the light chain variable domain of 3F9. Humanized sequence is based on IGKV3-11*01 acceptor framework and IGKJ2*01 joining region. FIG. 14B discloses SEQ ID NOS 54-60, respectively, in order of appearance. FIG. 14C lists potential humanized sequences of the heavy chain variable domain of 9C2. Humanized sequence is based on IGHV1-46*01 acceptor framework and IGHJ4*01 joining region. FIG. 14C discloses SEQ ID NOS:61, 49 and 62-67, respectively, in order of appearance. FIG. 14D lists potential humanized sequences of the light chain variable domain of 9C2. Humanized sequence is based on IGKV3-11*01 acceptor framework and IGKJ2*01 joining region. FIG. 14D discloses SEQ ID NOS:68, 55 and 69-74, respectively, in order of appearance. CDR sequences noted in bold. CDR definitions are AbM from website www.bioinf.org.uk/abs/. "b" notes buried sidechain; "p" notes partially buried; "i" notes sidechain at interface between VH and VL domains. Sequence differences between human and murine germlines noted by asterisk (*). Potential additional mutations in frameworks are noted below sequence. Potential changes in CDR sequences noted below each CDR sequence. These may prevent asparagine (N) deamidation.

FIGS. 15A and 15B show deglycosylation of 3F9 by treatment with EndoS (16A) and that deglycosylation did not have an impact on antigen recognition (16B)

DETAILED DESCRIPTION OF THE INVENTION

Terminology

Figure 3A:
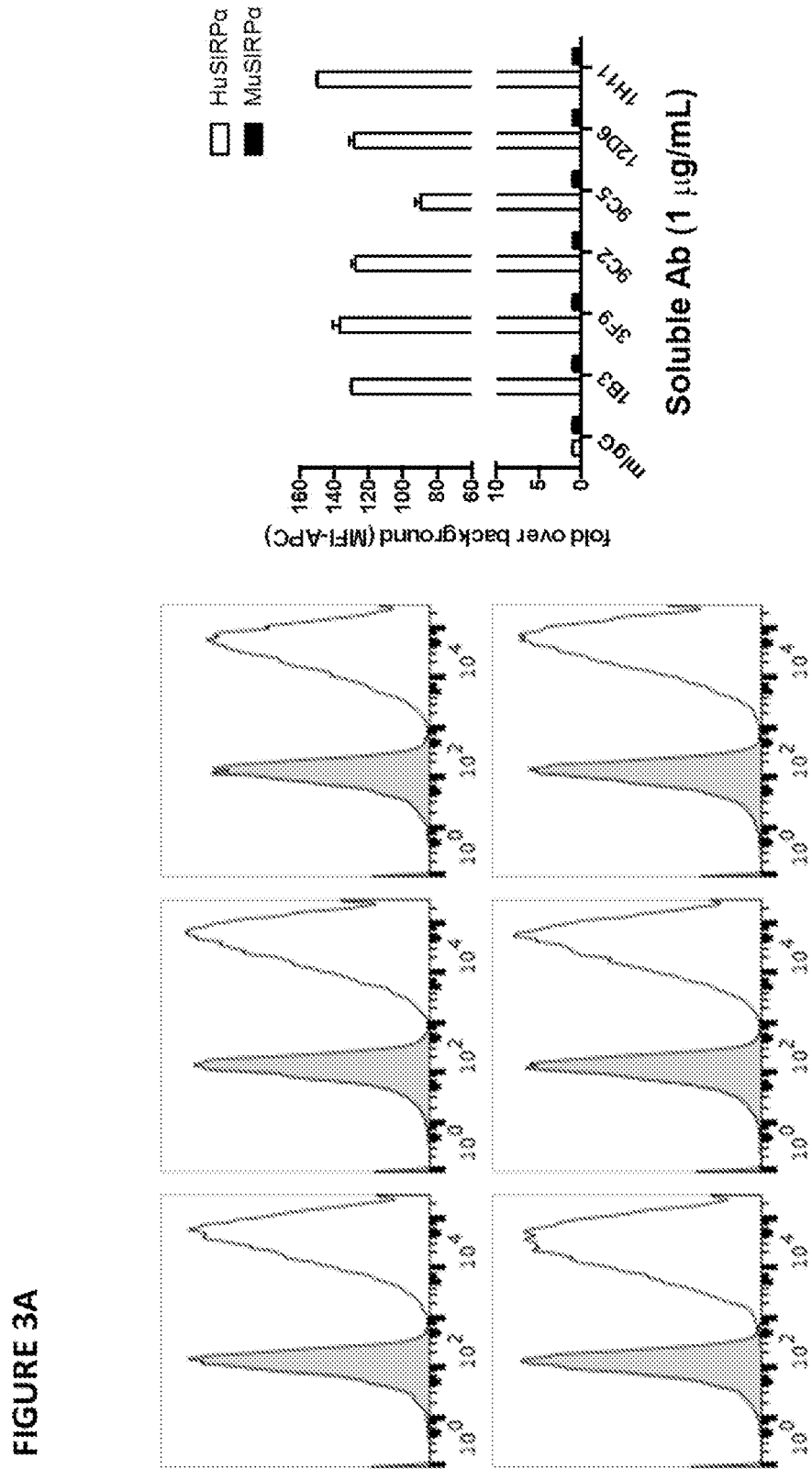
FIG. 3A shows FACS histograms on the left panel of selected SIRPA antibodies binding to the rodent Chinese hamster ovary cell line (CHO) expressing either human SIRPA (HuSIRPA) or mouse SIRPA (MuSIRPA). Shaded histograms represent the CHO-MuSIRPA cells. Black outlined histograms represent the CHO-HuSIRPA cells. The right panel presents the relative MFI values of SIRPA antibodies binding HuSIRPA compared to MuSIRPA. Results are expressed as fold over background. The background level is set to 1 on y-axis. Antibody mIgG is the isotype negative control.

As used in herein, the singular forms", "an" and "the" include plural referents unless the content clearly dictates otherwise. Thus, for example, reference to "an antibody" optionally includes a combination of two or more such molecules, and the like.

The term "about" as used herein refers to the usual error range for the respective value readily known to the skilled person in this technical field.

The term "antibody" is used herein in the broadest sense and encompasses various antibody structures, including but not limited to monoclonal antibodies, polyclonal antibodies, multispecific antibodies, such as bispecific antibodies, and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules, such as scFv molecules; and multispecific antibodies formed from antibody fragments.

An "antibody that binds to the same epitope" or that "has the same binding specificity" as a reference antibody refers to an antibody that blocks binding of the reference antibody to its antigen in a competition assay by 50% or more, and conversely, the reference antibody blocks binding of the antibody to its antigen in a competition assay by 50% or more. An antibody that binds to the same epitope may bind to the same epitope as a reference antibody, or may bind to a portion of the epitope. An exemplary competition assay is provided herein.

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions (HVRs) in each chain that interrupt the four "framework" regions established by the light and heavy chain variable regions. The CDRs are the primary contributors to binding to an epitope of an antigen. The CDRs of each chain are referred to as CDR1, CDR2, and CDR3, numbered sequentially starting from the N-terminus, and are also identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. The term "CDR" may be used interchangeably with "HVR".

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996). Reference to CDRs as determined by Kabat numbering are based, for example, on Kabat et al., Sequences of Proteins of Immunological Interest, 5th Ed. Public Health Service, National Institute of Health, Bethesda, Md. (1991)). Chothia CDRs are determined as defined by Chothia (see, e.g., Chothia and Lesk J. Mol. Biol. 196:901-917 (1987)).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

An "Fc region" refers to a C-terminal region of an immunoglobulin heavy chain, excluding the first constant region of a native immunoglobulin. The term includes refers to native Fc regions and variant Fc regions. An "Fc region" in the context of native immunoglobulins thus typically refers to the last two constant region immunoglobulin domains of IgA, IgD, and IgG, and the last three constant region immunoglobulin domains of IgE and IgM, and the flexible hinge N-terminal to these domains. For IgA and IgM, the Fc may include the J chain. For IgG, a native Fc comprises immunoglobulin domains Cγ2 and Cγ3 and the hinge between Cγ1 and Cγ. It is understood in the art that the boundaries of the Fc region may vary, however, the human IgG heavy chain Fc region is usually defined to comprise residues C226 or P230 to its carboxyl-terminus, using the numbering according to the EU index as in Kabat et al. (1991, NIH Publication 91-3242, National Technical Information Service, Springfield, Va.). The C-terminal lysine (residue 447 according to the EU or, Kabat numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4. The term "Fc region" includes naturally occurring allelic variants of the Fc region as well as modifications that modulate effector function. Fc regions also include variants that don't result in alterations to biological function. For example, one or more amino acids can be deleted from the N-terminus or C-terminus of the Fc region of an immunoglobulin without substantial loss of biological function.

The term "Fc receptor" or "FcR" describes a receptor that binds to the Fc region of an antibody. An FcR suitable for use in the present invention is typically a native human FcR or variant.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% identity with a native sequence Fc region and/or with an Fc region of a parent polypeptide, and most preferably at least about 90% identity therewith, more preferably at least about 95% identity therewith.

An "antagonist" antibody, or an "inhibitory" antibody is an antibody, such as an anti-SIRPA antibody of the present disclosure, that inhibits or reduces (e.g., decreases) one or more activities or functions of the antigen after the antibody binds the antigen. In some embodiments, an antagonist antibody may block binding of one or more ligands to the antigen. In some embodiments antagonist antibodies or inhibitory antibodies substantially or completely inhibit one or more activities or functions of the antigen; and/or binding of a ligand to the antigen.

The term "equilibrium dissociation constant" abbreviated ($K_D$), refers to the dissociation rate constant ($k_d$, time$^{-1}$) divided by the association rate constant ($k_a$, time$^{-1}$ M$^{-1}$). Equilibrium dissociation constants can be measured using any method. Thus, in some embodiments antibodies of the present disclosure have a $K_D$ of less than about 50 nM, typically less than about 25 nM, or less than 10 nM, e.g., less than about 5 nM or than about 1 nM and often less than about 100 pM as determined by surface plasmon resonance analysis using a biosensor system such as a Biacore® system performed at 37° C. In some embodiments, an antibody of the present disclosure has a $K_D$ of less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, less than $5\times10^{-10}$ M, less than $10^{-10}$ M, less than $5\times10^{-11}$ M, less than $10^{-11}$M, less than $5\times10^{-12}$M, less than $10^{-12}$M, less than $5\times10^{-13}$ M, less than $10^{-13}$ M, less than $5\times10^{-14}$M, less than $10^{-14}$M, less than $5\times10^{-15}$ M, or less than $10^{-15}$ M or lower as measured as a bivalent antibody. In the context of the present invention, an "improved" $K_D$ refers to a lower $K_D$.

The term "bivalent molecule" as used herein refers to a molecule that has two antigen-binding sites. In some embodiments, a bivalent molecule of the present invention is a bivalent antibody or a bivalent fragment thereof. In some embodiments, a bivalent molecule of the present invention is a bivalent antibody. In some embodiments, a bivalent molecule of the present invention is an IgG. In general monoclonal antibodies have a bivalent basic structure. IgG and IgE have only one bivalent unit, while IgA and IgM consist of multiple bivalent units (2 and 5, respectively) and thus have higher valencies. This bivalency increases the avidity of antibodies for antigens.

The terms "bivalent binding" or "bivalently binds to" as used herein refer to the binding of both antigen-binding sites of a bivalent molecule to its antigen. Preferably both antigen-binding sites of a bivalent molecule share the same antigen specificity.

The term "valency" as used herein refers to the number of different binding sites of an antibody for an antigen. A monovalent antibody comprises one binding site for an antigen. A bivalent antibody comprises two binding sites for the same antigen.

The phrase "specifically (or selectively) binds" to an antigen or target or "specifically (or selectively) immunoreactive with," when referring to a protein or peptide, refers to a binding reaction whereby the antibody binds to the antigen or target of interest. In the context of this invention, the antibody typically binds to SIRPA with a $K_D$ that is at least 100-fold greater than its affinity for other antigens. In some embodiments, the antibody binds to human SIRPA with a $K_D$ that is at least 100-fold greater than its affinity for other antigens. In some embodiments, the antibody binds to mouse and human SIRPA. As used herein "specific binding" or "selective binding" thus does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

An anti-SIRPA antibody of the present invention "down-regulates" the level of SIRPA present on the cell surface of cells that express SIRPA. Thus, as used in the present disclosure "down-regulation" refers to the ability of the antibody to decrease the level of SIRPA present on the cell surface of cells that express SIRPA, e.g., human macrophages. An anti-SIRPA antibody of the present invention is considered to down-regulate SIRPA when the level of SIRPA detected on the cell surface is decreased by at least 75% at least 80%, at least 85%, or at least 90% compared to an isotype-matched control antibody.

An "isolated" antibody, such as an anti-SIRPα antibody of the present disclosure, is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T cells since at least one component of the antibody's natural environment will not be present. Ordinarily, however, an isolated polypeptide or antibody will be prepared by at least one purification step.

The terms "identical" or percent "identity," in the context of two or more polypeptide sequences, refer to two or more sequences or subsequences that are the same or have a specified percentage of amino acid residues that are the same (e.g., at least 70%, at least 75%, at least 80%, 85%, 90%, 91%, 92%, 93%, 94%, 95%, 96%, 97%, 98%, 99%, or higher) identity over a specified region, when compared and aligned for maximum correspondence over a comparison window or designated region. Alignment for purposes of determining percent amino acid sequence identity can be performed in various methods, including those using publicly available computer software such as BLAST, BLAST-2, ALIGN or Megalign (DNASTAR) software. Examples of algorithms that are suitable for determining percent sequence identity and sequence similarity the BLAST 2.0 algorithms, which are described in Altschul et al., Nuc. Acids Res. 25:3389-3402 (1977) and Altschul et al., J. Mol. Biol. 215:403-410 (1990). Thus, for purposes of this invention, BLAST 2.0 can be used with the default parameters described to determine percent sequence for nucleic acid sequences or polypeptide sequences.

Overview of Certain Aspects of the Invention.

The present disclosure relates to agents (e.g., anti-SIRPA antibodies) that SIRPA and/or inhibit interaction between SIRPA and one or more SIRPA ligands; methods of making and using such agents (e.g., anti-SIRPA antibodies); pharmaceutical compositions containing such agents (e.g., anti-SIRPA antibodies); nucleic acids encoding such agents (e.g., anti-SIRPA antibodies); and host cells containing nucleic acids encoding such agents (e.g., anti-SIRPA antibodies).

An agent of the present disclosure that decreases cellular levels of SIRPA and/or inhibits interaction between SIRPA and one or more SIRPA ligands is a molecule having one or more of the following characteristics: (1) inhibits or reduces one or more SIRPA activities; (2) the ability to inhibit or reduce binding of SIRPA to one or more of its ligands; (3) the ability to reduce SIRPA expression (such as at the mRNA level and/or at protein level) in SIRPA-expressing cells; (4) the ability to interact, bind, or recognize a SIRPA protein; (5) the ability to specifically interact with or bind to a SIRPA protein; and (6) the ability to treat, ameliorate, or prevent any aspect of a disease or disorder described or contemplated herein.

Illustrative agents that inhibit the production of SIRPA include, without limitation, compounds that specifically inhibit SIRPA synthesis and/or release, antisense molecules directed to SIRPA, or a short interfering RNA (siRNA) molecule directed to a nucleic acid encoding a SIRPA. Additional exemplary agents that inhibit one or more SIRPA activities include, without limitation, anti-SIRPA antibodies that specifically bind to a SIRPA protein, compounds that specifically inhibit one or more SIRPA activities such as small molecule inhibitors and/or peptide inhibitors, compounds that specifically inhibit SIRPA binding to one or more ligands, a SIRPA structural analog, or an RNA or DNA aptamer that binds SIRPA. In some embodiments, an agent that decreases cellular levels of SIRPA and/or inhibits interaction between SIRPA and one or more SIRPA ligands is an allosteric inhibitor. In some embodiments, an agent that decreases cellular levels of SIRPA and/or inhibits interaction between SIRPA and one or more SIRPA ligands is an orthosteric inhibitor.

In certain embodiments, an agent that decreases cellular levels of SIRPA and/or inhibits interaction between SIRPA and one or more SIRPA ligands is a small molecule inhibitor, including, without limitation, small peptides or peptide-like molecules, soluble peptides, and synthetic non-peptidyl organic or inorganic compounds. A small molecule inhibitor may have a molecular weight of any of about 100 to about 20,000 daltons (Da), about 500 to about 15,000 Da, about 1000 to about 10,000 Da. Methods for making and testing the inhibitory effect a small molecule has on one or more SIRPA activities are well known in the art and such methods can be used to assess the effect of the small molecule inhibitor on SIRPA activity. For example, any of the methods and assays disclosed herein may be used to screen for small molecule inhibitors that decrease cellular levels of SIRPA and/or inhibit interaction between SIRPA and one or more SIRPA ligands.

In certain embodiments, an agent that decreases cellular levels of SIRPA and/or inhibits interaction between SIRPA and one or more SIRPA ligands comprises at least one antisense molecule capable of blocking or decreasing the expression of a functional SIRPA by targeting nucleic acids encoding a SIRPA. Nucleic acid sequences of SIRPA are known in the art. For example, a human SIRPA can have a nucleic acid sequence as shown in NCBI Accession number NM_080792 or Y10375.1 a mouse SIRPA can have a nucleic acid sequence as shown in NCBI Accession No. BC062197. Methods are known for the preparation of antisense oligonucleotide molecules and such methods can be used to prepare antisense oligonucleotides that will specifically bind one or more of a SIRPA mRNA without cross-reacting with other polynucleotides. Exemplary sites of targeting include, but are not limited to, the initiation codon, the 5' regulatory regions, the coding sequence, including any conserved consensus regions, and the 3' untranslated region. In certain embodiments, the antisense oligonucleotides are about 10 to about 100 nucleotides in length, about 15 to about 50 nucleotides in length, about 18 to about 25 nucleotides in length, or more. In certain embodiments, the oligonucleotides further comprise chemical modifications to increase nuclease resistance and the like, such as, for example, phosphorothioate linkages and 2'-O-sugar modifications known to those of ordinary skill in the art.

In certain embodiments, an agent that decreases cellular levels of SIRPA and/or inhibits interaction between SIRPA and one or more SIRPA ligands comprises at least one siRNA molecule capable of blocking or decreasing the expression of a functional SIRPA by targeting nucleic acids encoding a SIRPA. Methods for preparation of siRNA molecules are well known in the art and such methods can be used to prepare siRNA molecules that will specifically target a SIRPA mRNA without cross-reacting with other polynucleotides. siRNA molecules may be generated by methods such as by typical solid phase oligonucleotide synthesis, and often will incorporate chemical modifications to increase half-life and/or efficacy of the siRNA agent, and/or to allow for a more robust delivery formulation. Alternatively, siRNA molecules are delivered using a vector encoding an expression cassette for intracellular transcription of siRNA.

In certain embodiments, an agent that decreases cellular levels of SIRPA and/or inhibits interaction between SIRPA and one or more SIRPA ligands is an RNA or DNA aptamer that binds or physically interacts with a SIRPA, and blocks interactions between a SIRPA and one or more of its ligands. In certain embodiments, the aptamer comprises at least one RNA or DNA aptamer that binds to a mature form of SIRPA.

In certain embodiments, an agent that decreases cellular levels of SIRPA and/or inhibits interaction between SIRPA and one or more SIRPA ligands comprises at least one Siglec-9 structural analog. The term "SIRPA structural analog" refers to compounds that have a similar three dimensional structure as part of that of a SIRPA and which bind to one or more CD3 ligands under physiological conditions in vitro or in vivo, wherein the binding at least partially inhibits a SIRPA biological activity. Suitable SIRPA structural analogs can be designed and synthesized through molecular modeling of SIRPA binding to a ligand, such as a SIRPA ligand of the present disclosure. The SIRPA structural analogs can be monomers, dimers, or higher order multimers in any desired combination of the same or different structures to obtain improved affinities and biological effects. In some embodiments, the agent binds to or interacts with an amino acid sequence of a SIRPA.

In certain embodiments, an agent that decreases cellular levels of SIRPA and/or inhibits interaction between SIRPA and one or more SIRPA ligands comprises a soluble SIRPA receptor protein, a soluble SIRPA-Fc fusion protein. In certain embodiments, such agents bind one or more SIRPA ligands and thereby prevent the interaction between the SIRPA ligand and SIRPA receptor.

Assays

Agents that decrease cellular levels of SIRPA and/or inhibit interaction between SIRPA and one or more SIRPA ligands may be identified and/or characterized using methods well known in the art, such as, for example, radiolabeled inhibitor assays, optical assays, protein binding assays, biochemical screening assays, immunoassays, mass shift measurement assays, fluorescence assays, and/or fluorogenic peptide cleavage assays.

Binding Assays and Other Assays

In certain embodiments, agents that decrease cellular levels of SIRPA and/or inhibit interaction between SIRPA and one or more SIRPA ligands can be identified by techniques well known in the art for detecting the presence of a SIRPA agent candidate's interaction and/or binding affinity to a SIRPA.

In certain embodiments, agents that interact with SIRPA can be identified using a radiolabeled inhibitor assay. For example, a known amount of a radiolabeled agent candidate may be incubated with a known amount of immobilized SIRPA and a buffer. Subsequently, the immobilized SIRPA may be washed with a buffer and the immobilized SIRPA may be measured for the remaining presence of the radiolabeled SIRPA agent candidate using techniques known in the art, such as, for example, a gamma counter. A measurement indicating the presence of a radiolabeled substance may indicate the radiolabeled agent candidate is capable of interacting with and/or binding to SIRPA.

In certain embodiments, an agent that interacts with a SIRPA may be identified using an optical technique. An exemplary optical technique to detect a SIRPA-interacting agent may include, e.g., attaching SIRPA to a colorimetric resonant grafting surface, thereby shifting the wavelength of reflected light due to changes in the optical path the light must take, and subsequently measuring additional changes in the wavelength of reflected light when a candidate agent is allowed to interact with SIRPA. For example, no change in the measured wavelength of reflected light when an agent is incubated with SIRPA may indicate that the agent candidate is unable to interact with SIRPA. Changes in the measured wavelength of reflected light when an agent candidate is incubated with SIRPA may indicate that the agent candidate is capable of binding and/or interacting with SIRPA.

In certain embodiments, an agent that interacts with SIRPA may be identified using a protein-binding assay. An exemplary protein-binding assay to detect a SIRPA-binding agent may include, e.g., co-immunoprecipitation of SIRPA in the presence of the agent candidate. For example, SIRPA may be incubated with the agent candidate in buffer, and subsequently an immobilized molecule specific to capture SIRPA, such as, for example, an anti-SIRPA antibody, may be used to capture SIRPA in the presence of the agent candidate and bind the SIRPA, potentially with an interacting agent candidate, during wash procedures known in the art. Subsequently, SIRPA, potentially with an interacting agent candidate, can be released and the presence of an agent candidate may be detected, based on the agent candidate characteristics, by techniques, such as, for example, mass spectrometry and/or Western blot.

In certain embodiments, an agent that interacts with a SIRPA may be identified using a biochemical and/or an immunoassay assay well known in the art. An exemplary technique may include, e.g., an assay to quantitatively measure changes in SIRPA concentration and/or protein half-life using techniques, such as, for example, Western blot, immunostaining, and co-immunoprecipitation. For example, an agent candidate may be incubated with a sample containing a SIRPA, such as a cell expressing SIRPA, and subsequently SIRPA protein quantity and/or cellular levels may be measured at points during a time course study. Changes in protein quantity, cellular levels, and/or protein half-life in comparison to a control treatment may indicate that the SIRPA agent candidate may be capable of altering SIRPA half-life and/or activity.

In certain embodiments, a mass shift measurement assay may be used to identify an agent that interacts with a SIRPA. An exemplary mass shift measurement assay may include, e.g., detecting the presence of a strongly and/or covalently bound SIRPA agent by measuring a change in SIRPA mass when the agent candidate is interacting with SIRPA by using instruments, such as, but not limited to, a mass spectrometer. For example, a mass shift assay may be performed on a whole protein and/or a peptide-based analysis, depending on the nature of the agent candidate interaction. Detection of a mass shift correlating with the addition of said agent candidate to SIRPA may indicate that the agent candidate may be capable of interacting with or otherwise inhibiting a SIRPA. Additionally, an exemplary mass shift measurement assay may include, e.g., detecting the addition of mass to SIRPA correlating with the respective agent candidate mass when the agent candidate is interacting with SIRPA using techniques, such as, for example, surface plasmon resonance. For example, the change in the refractive index of light may be measured and correlated with a change in mass of SIRPA attached to a sensor surface.

In certain embodiments, a chemical cross-linking assay may be used to identify a SIRPA agent that interacts with a SIRPA. For example, an agent candidate may be incubated with a SIRPA, in vivo or in vitro, with a molecule cross-linker capable of covalently linking an agent candidate interacting with SIRPA to said SIRPA molecule. Subsequently, techniques, such as, but not limited to, mass spectrometry and/or Western blot, may be used to identify an agent candidate that may be capable of interacting with or otherwise inhibiting SIRPA. For example, detection of SIRPA covalently cross-linked with the agent candidate may indicate that the agent candidate may be capable of interacting with or otherwise inhibiting SIRPA.

In certain embodiments, agents that interact with a SIRPA may be identified using a fluorescence assay. For example, a known amount of a fluorescent agent candidate may be incubated with a known amount of immobilized SIRPA and a buffer. Subsequently, the immobilized SIRPA may be washed with a buffer and the immobilized SIRPA may be measured for the remaining presence of a fluorescent SIRPA agent candidate using techniques known in the art, such as, but not limited to, fluorescence detection. A measurement indicating the presence of a fluorescent substance may indicate the fluorescent agent candidate is capable of interacting with and/or binding to SIRPA.

Assays known in the art and described herein (e.g., Examples 2-11) can be used for identifying and testing biological activities of SIRPA agents of the present disclosure. In some embodiments, assays for testing the ability of SIRPA agents for modulating one or more Siglec-9 activities are provided.

Anti-SIRP-alpha (SIRPA) Antibodies
Brief Overview of Aspects of Certain Anti-SIRPA Antibodies of the Present Disclosure In some embodiments, anti-SIRPA antibodies of the present disclosure have one or more antagonistic activities that are due, at least in part, to the ability of the antibodies to down regulate cellular SIRPA. In some embodiments, an isolated SIRPA antibody of the present disclosure selectively binds SIRPA and down-regulates SIRPA. In some embodiments, the antibody does not block binding of a SIRPA ligand, e.g., CD47, to SIRPA expressed on cells. In alternative embodiments, the antibody blocks binding of a SIRPA ligand, e.g., CD47, to SIRPA. In some embodiments, the antibody is a human antibody, a humanized antibody, a bispecific antibody, a multivalent antibody, or a chimeric antibody. Exemplary descriptions of such antibodies are found throughout the present disclosure. In some embodiments, the antibody is a bispecific antibody recognizing a first antigen and a second antigen.

In some embodiments, anti-SIRPA antibodies of the present disclosure selectively bind to human SIRPA, including human allelic variants, also revered to herein as "polymorphic" variants, but not mouse SIRPA, and do not bind to SIRPB. FIG. 1A shows an amino acid sequence alignment between the two most common alleles of human SIRPA protein (v1 and v2, accession numbers are NP542970 and CAA71403, respectively) depicting the divergent residues within the ligand-binding domain. Thus, in some embodiments, an anti-SIRPA antibody of the present disclosure binds to a linear or conformational epitope that is present in alleleic variants of human SIRPA, but not in SIRPB or mouse SIRPA. FIG. 1B shows an amino acid sequence alignment between the human SIRPA v1 protein and the human SIRPB1 protein, accession numbers are NP542970 and O00241, respectively, depicting the homology between the two proteins. FIG. 2 shows an amino acid sequence alignment between the human SIRPA protein and the mouse SIRPA protein, accession numbers are NP542970 and Q6P6I8, respectively depicting the homology between the two proteins. In some embodiments, the antibodies of the present disclosure selectively bind to human and mouse SIRPA and do not bind to SIRPB.

SIRPA is a single-pass type I membrane protein. Within the amino acid sequence of human SIRPA (SEQ ID NO:1), an extracellular domain is located at amino acid residues 31-373; a transmembrane domain is located at amino acid residues 374-394; and an intracellular domain is located at amino acid residues 395-504.

Human SIRPA comprises a single V-set and two C1-sets of Ig super family (IgSF) domains, referred to as the D1 domain, the D2 domain, and the D3 domain, respectively. The D1 domain comprises amino acid residues 32-137 of human SIRPA; the D2 domain comprises amino acid residues 148-247 of human SIRPA; and the D3 domain comprises amino acid residues 254-348 of human SIRPA.

In some embodiments, an anti-SIRPA antibody of the present disclosure binds to the D1 domain of SIRPA. In some embodiments, an anti-SIRPA antibody of the present disclosure binds to the D1 domain of human SIRPA comprising amino acid residues 32-137 of human SIRPA amino acid sequence of SEQ ID NO:1. In some embodiments, an anti-SIRPA antibody of the present disclosure binds to an epitope within the D1 domain of human SIRPA. In some embodiments, an anti-SIRPA antibody of the present disclosure binds to an epitope within the D1 domain of human SIRPA, wherein the epitope comprises an amino acid sequence selected from the group consisting of amino acid residues 32-137, amino acid residues 32-52, amino acid residues 55-121, amino acid residues 58-73, amino acid residues 68-83, amino acid residues 78-93, amino acid residues 88-103, amino acid residues 98-113, amino acid residues 108-123, and amino acid residues 118-133 of the human SIRPA amino acid sequence of SEQ ID NO:1.

In some embodiments, an anti-SIRPA antibody of the present disclosure binds to the D2 domain of SIRPA. In some embodiments, an anti-SIRPA antibody of the present disclosure binds to the D2 domain of human SIRPA comprising amino acid residues 148-247 of the human SIRPA amino acid sequence of SEQ ID NO:1. In some embodiments, an anti-SIRPA antibody of the present disclosure binds to an epitope within the D2 domain of human SIRPA. In some embodiments, an anti-SIRPA antibody of the present disclosure binds to an epitope within the D2 domain of human SIRPA, wherein the epitope comprises an amino acid sequence selected from the group consisting of amino acid residues 148-247, amino acid residues 148-168, amino acid residues 158-173, amino acid residues 168-183, amino acid residues 170-228, amino acid residues 178-193, amino acid residues 188-203, amino acid residues 198-213, amino acid residues 208-223, amino acid residues 218-233, and amino acid residues 228-243 of the human SIRPA amino acid sequence of SEQ ID NO:1.

In some embodiments, an anti-SIRPA antibody of the present disclosure binds to the D3 domain of SIRPA. In some embodiments, an anti-SIRPA antibody of the present disclosure binds to the D3 domain of human SIRPA comprising amino acid residues 254-348 of the human SIRPA amino acid sequence of SEQ ID NO:1. In some embodiments, an anti-SIRPA antibody of the present disclosure binds to an epitope within the D3 domain of human SIRPA. In some embodiments, an anti-SIRPA antibody of the present disclosure binds to an epitope within the D3 domain of human SIRPA, wherein the epitope comprises an amino acid sequence selected from the group consisting of amino acid residues 254-348, amino acid residues 254-274, amino acid residues 264-279, amino acid residues 274-289, amino acid residues 273-331, amino acid residues 281-315, amino acid residues 281-337, amino acid residues 284-299, amino acid residues 294-309, amino acid residues 304-319, amino acid residues 314-329, amino acid residues 324-339, and amino acid residues 334-348 of the human SIRPA amino acid sequence of SEQ ID NO:1.

In some embodiments, the antibody binds to the D1 domain of SIRPA, e.g., human SIRPA. In some embodiments, the antibody binds to the D2 domain of SIRPA e.g., human SIRPA. In some embodiments, the antibody binds to the D3 domain of SIRPA, e.g., human SIRPA. In some embodiments, an anti-SIRPA antibody of the present disclosure binds to the same SIRPA epitope or part of the SIRPA epitope bound by an antibody having the CDRs of the antibody designated as 3F9 in Table 2. In some embodiments, an anti-SIRPA antibody of the present disclosure binds to the same SIRPA epitope or part of the SIRPA epitope bound by an antibody having the CDRs of the antibody designated as 9C2 in Table 2, which competes with 3F9 for binding to SIRPA and binds to all of part of the same epitope as 3F9. Accordingly, in some embodiments, an antibody of the present disclosure binds to the same SIRPA epitope or part of the SIRPA epitope bound by an antibody having the CDRs of the antibody designated as 3F9 in Table 2 and binds to the same epitope or part of the SIRPA epitope bound by an antibody having the CDRs of the antibody designated as 9C2 in Table 2.

In some embodiments, an anti-SIRPA antibody of the present disclosure competes with 3F9 and 9C2 for binding to human SIRPA.

In preferred embodiments, an antibody of each of the preceding three paragraphs does not block CD47 binding to SIRPA.

SIRPA Down-Regulation

Certain aspects of the present disclosure relate to anti-SIRPA antibodies that down-regulate, i.e., decrease cellular levels of SIRPA. In some embodiments, the anti-SIRPA antibody decreases cellular levels of SIRPA without inhibiting the interaction (e.g., binding) between SIRPA and one or more SIRPA ligands, e.g., CD47. In some embodiments, the anti-SIRPA antibody decreases cellular levels of SIRPA and inhibits the interaction (e.g., binding) between SIRPA and one or more SIRPA ligands, e.g., CD47.

Cellular levels of SIRPA may refer to, without limitation, cell surface levels of SIRPA, intracellular levels of SIRPA, and total levels of SIRPA. In some embodiments, a decrease in cellular levels of SIRPA comprises decrease in cell surface levels of SIRPA. As used herein, an anti-SIRPA antibody decreases cell surface levels of SIRPA if it induces a decrease of 25% or more in cell surface levels of SIRPA as measured by any in vitro cell-based assays or suitable in vivo model described herein or known in the art, for example utilizing flow cytometry, such as fluorescence-activated cell sorting (FACS), to measure cell surface levels of SIRPA. In some embodiments, a decrease in cellular levels of SIRPA comprises a decrease in intracellular levels of SIRPA. As used herein, an anti-SIRPA antibody decreases intracellular levels of Siglec-9 if it induces a decrease of 25% or more in intracellular levels of SIRPA as measured by any in vitro cell-based assays or suitable in vivo model described herein or known in the art, for example immunostaining, Western blot analysis, co-immunoprecipitation, and cell cytometry. In some embodiments, a decrease in cellular levels of SIRPA comprises a decrease in total levels of SIRPA. As used herein, an anti-SIRPA antibody decreases total levels of SIRPA if it induces a decrease of 25% or more in total levels of SIRPA as measured by any in vitro cell-based assays or suitable in vivo model described herein or known in the art, for example immunostaining, Western blot analysis, co-immunoprecipitation, and cell cytometry. In some embodiments, the anti-SIRPA antibodies induce SIRPA degradation, SIRPA cleavage, SIRPA internalization, SIRPA shedding, downregulation of SIRPA expression, or any combination thereof. In some embodiments, cellular levels of SIRPA are measured on primary cells (e.g., dendritic cells, bone marrow-derived dendritic cells, monocytes, microglia, and macrophages) or on cell lines utilizing an SIRPA cell assay.

In some embodiments, a downregulating anti-SIRPA antibody has an $IC_{50}$ of 200 nM of less, typically 100 nM or less (50% of SIRPA expressed on the cell surface is downregulated), after 4 hours of exposure of human macrophages to the antibody at 37° C. In some embodiments, SIRPA remains down-regulated for at least 24 hours of exposure to an antibody of the present invention. Cells may be analyzed for SIRPA surface expression using any technology, e.g., flow cytometry.

In some embodiments, anti-SIRPA antibodies of the present disclosure decrease cellular levels of SIRPA by at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more as compared to cellular levels of SIRPA in the absence of the anti-SIRPA antibody.

In some embodiments, which may be combined with any of the down-regulation activities summarized in the preceding paragraphs, an anti-SIRPA antibody of the present disclosure inhibits cell surface clustering of SIRPA.

In some embodiments, an anti-SIRPA antibody of the present disclosure down-regulates SIRPA, but does not block binding of a SIRPA ligand, e.g., CD47 to SIRPA. In the context of the present invention, an antibody that does not block binding of CD47 to SIRPA refers to an antibody that does not result in a significant decrease in CD47 binding to SIRPA when the antibody is incubated with CD47 and cells expressing SIRPA. A "significant decrease" in the context of CD47 binding to SIRPA refers to a decrease in binding of 30% or less, typically at least 25%, at least 20%, at least 15%, or at least 10% or less compared to CD47 binding to SIRPA in the presence of an isotype-matched control antibody that does not bind SIRPA. An illustrative assay for assessing blocking activity is set forth in the examples. For example, cells that express human SIRPA, e.g., human macrophages are cells such as CHO cells that are modified to express human SIRPA, are plated at $10^5$ cells/well in a 96-well plate, washed, and incubated in 100 µl buffer for fluorescent activate cell sorting containing 1.0 µg/ml of monoclonal antibody or isotype control. Cells are then washed and incubated in with soluble human CD47 for 30 minutes on ice. Cells are then analyzed for surface-bound CD47.

Alternatively, in some embodiments, an anti-SIRPA antibody of the present disclosure down-regulates SIRPA, but blocks binding of CD47 to SIRPA. An antibody that blocks CD47 binding typically blocks CD47 binding by 50% or greater, typically 75%, or 90% or greater.

Inhibition of SIRPA Activities

In some embodiments, anti-SIRPA antibodies of the present disclosure inhibit one or more activities of SIRPA, including, without limitation: SIRPA binding to one or more SIRPA ligands, optionally wherein the one or more SIRPA ligands are selected from the group consisting of CD47, surfactant protein A and D and any combination thereof; decreasing proliferation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting migration of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting one or more functions of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibition of one or more types of clearance selected from the group consisting of apoptotic neuron clearance, nerve tissue debris clearance, dysfunctional synapse clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; inhibition of tumor cell killing by one or more of microglia, macrophages, neutrophils, NK cells, dendritic cells, bone marrow-derived dendritic cells, neutrophils, T cells, T helper cells, or cytotoxic T cells; inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; modulated expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; promoting or rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, non-tumorigenic CD45+ CD14+ myeloid cells, and regulatory T cells into tumors; increasing the number of tumor-promoting myeloid/granulocytic immune-suppressive cells and/or non-tumorigenic CD45+CD14+ myeloid cells in a tumor, in peripheral blood, or other lymphoid organ; enhancing tumor-promoting activity of myeloid-derived suppressor cells and/or non-tumorigenic CD45+CD14+ myeloid cells; enhancing survival of non-tumorigenic myeloid-derived suppressor cells and/or non-tumorigenic CD45+CD14+ myeloid cells; decreasing activation of tumor-specific T lymphocytes with tumor killing potential; decreasing infiltration of tumor-specific NK cells with tumor killing potential; increasing tumor volume; increasing tumor growth rate; and decreasing efficacy of one or more immune-therapies that modulate anti-tumor T cell responses, optionally wherein the one or more immune-therapies are immune-therapies that target one or more target proteins selected from the group consisting of PD1/PDL1, CD40, OX40, ICOS, CD28, CD137/4-1BB, CD27, GITR, PD-L1, CTLA4, PD-L2, PD-1, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, TREM1, TREM2, CD39, CD73, CSF-1 receptor, and any combination thereof, or of one or more cancer vaccines.

In some embodiments, which may be combined with any of the other embodiments above, an anti-SIRPA antibody of the present disclosure induces one or more of the activities that are selected from the group consisting of increasing the number of tumor infiltrating CD3+ T cells; decreasing cellular levels of SIRPA in non-tumorigenic CD14+ myeloid cells, optionally wherein the non-tumorigenic CD14+ myeloid cells are tumor infiltrating cells or optionally wherein the non-tumorigenic CD14+ myeloid cells are present in blood; reducing the number of non-tumorigenic CD14+ myeloid cells, optionally wherein the non-tumorigenic CD14+ myeloid cells are tumor infiltrating cells or optionally wherein the non-tumorigenic CD14+ myeloid cells are present in blood; reducing PD-L1 levels in one or more cells, optionally wherein the one or more cells are non-tumorigenic myeloid-derived suppressor cells (MDSC); reducing PD-L2 levels in one or more cells, optionally wherein the one or more cells are non-tumorigenic myeloid-derived suppressor cells (MDSC); reducing B7-H2 levels in one or more cells, optionally wherein the one or more cells are non-tumorigenic myeloid-derived suppressor cells (MDSC); reducing B7-H3 levels in one or more cells, optionally wherein the one or more cells are non-tumorigenic myeloid-derived suppressor cells (MDSC); reducing CD200R levels in one or more cells, optionally wherein the one or more cells are non-tumorigenic myeloid-derived suppressor cells (MDSC); reducing CD163 levels in one or more cells, optionally wherein the one or more cells are non-tumorigenic myeloid-derived suppressor cells (MDSC); reducing CD206 levels in one or more cells, optionally wherein the one or more cells are non-tumorigenic myeloid-derived suppressor cells (MDSC); decreasing tumor growth rate of solid tumors; reducing tumor volume; increasing efficacy of one or more PD-1 inhibitors; increasing efficacy of one or more checkpoint inhibitor therapies and/or immune-modulating therapies, optionally wherein the one or more checkpoint inhibitor therapies and/or immune-modulating therapies target one or more of CTLA4, the adenosine pathway, PD-L1, PD-L2, OX40, TIM3, LAG3, or any combination thereof; increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; increasing proliferation of T cells in the presence of non-tumorigenic myeloid-derived suppressor cells (MDSC); inhibiting differentiation, survival, and/or one or more functions of non-tumorigenic myeloid-derived suppressor cells (MDSC); and killing CD33-expressing immunosuppressor non-tumorigenic myeloid cells and/or non-tumorigenic CD14-expressing cells in solid tumors and associated blood vessels when conjugated to a chemical or radioactive toxin.

In some embodiments, an anti-SIRPA antibody of the present disclosure decreases the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML).

In some embodiments, an anti-SIRPA antibody of the present disclosure induces or promotes the survival, maturation, functionality, migration, or proliferation of one or more immune cells, e.g., one or more immune cells are selected from the group consisting of dendritic cells, macrophages, neutrophils, NK cells, microglia, T cells, T helper cells, cytotoxic T cells, and any combination thereof in an individual.

As used herein, levels of SIRPA may refer to expression levels of the gene encoding SIRPA; to expression levels of one or more transcripts encoding SIRPA; to expression levels of SIRPA protein; and/or to the amount of SIRPA protein present within cells and/or on the cell surface. Any methods known in the art for measuring levels of gene expression, transcription, translation, and/or protein abundance or localization may be used to determine the levels of SIRPA.

In some embodiments, an isolated anti-SIRPA antibody of the present disclosure is a murine antibody. In some embodiments, an isolated anti-SIRPA antibody of the present disclosure is a human antibody, a humanized antibody, a bispecific antibody, a monoclonal antibody, a multivalent antibody, or a chimeric antibody. Exemplary descriptions of such antibodies are found throughout the present disclosure.

In some embodiments, anti-SIRPA antibodies of the present disclosure bind to a human SIRPA including human allelic variants (FIG. 1A, accession numbers NP542970 and CAA71403). In some embodiments, anti-SIRPA antibodies specifically bind to primate SIRPA, including human SIRPA. In some embodiments, anti-SIRPA antibodies of the present disclosure specifically bind to both human SIRPA and primate SIRPA. In some embodiments, anti-SIRPA antibodies of the present disclosure specifically bind to human SIRPA and cross-react with murine SIRPA.

HVR Sequences of Antibodies that Down-Regulate SIRPA that do not Block CD47 Binding In some embodiments, an anti-SIRPA antibody of the present disclosure down-regulates SIRPA and does not block CD47 binding to SIRPA. In some embodiments, such an antibody comprises a heavy chain variable region that comprises an HVR3 of antibody 3F9 as set forth in SEQ ID NO:11. In some embodiments, the HVR3 comprises the sequence set forth in SEQ ID NO:11 in which 1, 2, 3, 4, or 5 amino acids are substituted, e.g., conservatively substituted. In some embodiments, the HVR3 comprises the sequence set forth in SEQ ID NO:11 in which 1, 2, 3, or 4 amino acids are substituted, e.g., conservatively substituted. In some embodiments, the HVR3 comprises the sequence set forth in SEQ ID NO:11 in which 1, 2, or 3 amino acids are substituted, e.g., conservatively substituted. In some embodiments the HVR3 has 1 or 2 amino acids substituted compared to the sequence set forth in SEQ ID NO:11. In some embodiments, 1 or 2 amino acids are deleted, relative to SEQ ID NO:11. In some embodiments, the HVR3 has at least 65% identity or at least 75% identity to the amino acid sequence of SEQ ID NO:11.

In some embodiments, a heavy chain variable region of an anti-SIRPA antibody of the invention comprises an HVR3 as set forth in the preceding paragraph and an HVR1 and/or an HVR2 of antibody 3F9 as set forth in Table 3. In some embodiments, the HVR1 comprises the sequence of SEQ ID NO:9 in which 1, 2, 3, or 4 amino acid are substituted, e.g., conservatively substituted. In some embodiments, the HVR1 comprises the sequence of SEQ ID NO:9 in which 1, 2, or 3 amino acids; or 1 or 2 amino acids are substituted, e.g., conservatively substituted. In some embodiments, the HVR1 has at least 70%, at least 80%, or at least 90% identity to the amino acid sequence of SEq ID NO:9. In some embodiments, the HVR2 comprises the sequence of SEQ ID NO:10 in which 1, 2, 3, or 4 amino acid are substituted, e.g., conservatively substituted. In some embodiments, the HVR2 comprises the sequence of SEQ ID NO:10 in which 1, 2, or 3 amino acids; or 1 or 2 amino acids are substituted, e.g., conservatively substituted. In some embodiments, the HVR2 has at least 70%, at least 80%, or at least 90% identity to the amino acid sequence of SEQ ID NO:10.

In some embodiments, an anti-SIRPA antibody comprises a heavy chain variable region comprising an HVR3 of SEQ ID NO:11, an HVR1 of SEQ ID NO:9, and an HVR2 of SEQ ID NO:10.

In some embodiments, an anti-SIRPA antibody comprises a light chain variable region that comprises an HVR3 of antibody 3F9 as set forth in Table 2. In some embodiments, the HVR3 comprises the sequence the sequence set forth in SEQ ID NO:8 in which 1, 2, 3, or 4 amino acids are substituted, e.g., conservatively substituted. In some embodiments, the HVR3 comprises the sequence set forth in SEQ ID NO:8 in which 1, 2, or 3 amino acids are substituted, e.g., conservatively substituted. In some embodiments the HVR3 has 1 or 2 amino acid substituted compared to the sequence set forth in SEQ ID NO:8. In some embodiments, 1 or 2 amino acids are deleted, relative to SEQ ID NO:8. In some embodiments, the HVR3 has at least 65% identity to the amino acid sequence of SEQ ID NO:8. In some embodiments, the HVR3 has at least 85% identity to the amino acid sequence of SEQ ID NO:8.

In some embodiments, a light chain variable region of an anti-SIRPA antibody of the invention comprises an HVR3 as set forth in the preceding paragraph and an HVR1 and/or an HVR2 of antibody 3F9 as set forth in Table 2. In some embodiments, the HVR1 comprises the sequence of SEQ ID NO:6 in which 1, 2, 3, 4, 5, or 6; or 1, 2, 3, 4, or 5; amino acids are substituted, e.g., conservatively substituted. In some embodiments, the HVR1 comprises the sequence of SEQ ID NO:6 in which 1, 2, 3, or 4 amino acids are substituted, e.g., conservatively substituted. In some embodiments, the HVR1 comprises the sequence of SEQ ID NO:6 in which 1, 2, or 3 amino acids; or 1 or 2 amino acids, are substituted, e.g., conservatively substituted. In some embodiments, the HVR1 has at least 70%, at least 80%, or at least 90% identity to the amino acid sequence of SEQ ID NO:6. In some embodiments, the HVR2 comprises the sequence of SEQ ID NO:7 in which 1, 2, or 3 amino acids; or 1 or 2 amino acids are substituted, e.g., conservatively substituted. In some embodiments, the HVR2 has at least 70%, at least 85%, identity to the amino acid sequence of SEQ ID NO:7.

In some embodiments, an anti-SIRPA antibody comprises a light chain variable region having an HVR3 of SEQ ID NO:8, an HVR1 of SEQ ID NO:6, and an HVR2 of SEQ ID NO:7.

In some embodiments, an anti-SIRPA antibody of the present disclosure comprises a heavy chain variable region comprising an HVR3, HVR2, and HVR1 of antibody 3F9 as set forth in Table 3 and a light chain variable region comprising an HVR3, HVR2, and HVR1 of antibody 3F9 as set forth in Table 2. In some embodiments, an anti-SIRPA antibody comprises the six CDRs of 3F9 where at least one HVR differs from the HVR of 3F9 by one, two, or three amino acids; or one or two amino acids, compared to the corresponding HVR of 3F9. In some embodiments, such an antibody comprises two HVRs that differ from the corresponding HVR of 3F9 by one, two, or three amino acids; or one or two amino acids, compared to the corresponding HVR in of 3F9. In some embodiments, the antibody comprises three HVRs that differ from the corresponding HVR of 3F9 by one, two, or three amino acids; or one or two amino acids, compared to the corresponding HVR in of 3F9. In some embodiments, the antibody comprises four HVRs that differ from the corresponding HVR of 3F9 by one, two, or three amino acids; or one or two amino acids, compared to the corresponding HVR in of 3F9. In some embodiments, the antibody comprises five HVRs that differ from the corresponding HVR of 3F9 by one, two, or three amino acids; or one or two amino acids, compared to the corresponding HVR in of 3F9. In some embodiments, the antibody comprises one, two, or 3 amino acid changes; or one or two amino acid changes, in each HVR compared to the corresponding HVR of 3F9.

In some embodiments, an anti-SIRPA antibody comprises a heavy chain variable region that comprises an HVR3 of antibody 9C2 as set forth in SEQ ID NO:17. In some embodiments, the HVR3 comprises the sequence set forth in SEQ ID NO:17 in which 1, 2, 3, or 4 amino acids are substituted, e.g., conservatively substituted. In some embodiments, the HVR3 comprises the sequence set forth in SEQ ID NO:7 in which 1, 2, or 3 amino acids are substituted, e.g., conservatively substituted. In some embodiments the HVR3 has 1 or 2 amino acid substituted compared to the sequence set forth in SEQ ID NO:17. In some embodiments, 1 or 2 amino acids are deleted, relative to SEQ ID NO:17. In some embodiments, the HVR3 has at least 65% identity to the amino acid sequence of SEQ ID NO:17. In some embodiments, the HVR3 has at least 85% identity to the amino acid sequence of SEQ ID NO:17.

In some embodiments, a heavy chain variable region of an anti-SIRPA antibody of the invention comprises an HVR3 as set forth in the preceding paragraph and an HVR1 and/or an HVR2 of antibody 9C2 as set forth in Table 3. In some embodiments, the HVR1 comprises the sequence of SEQ ID NO:15 in which 1, 2, 3, or 4 amino acid are substituted, e.g., conservatively substituted. In some embodiments, the HVR1 comprises the sequence of SEQ ID NO:15 in which 1, 2, or 3 amino acids; or 1 or 2 amino acids are substituted, e.g., conservatively substituted. In some embodiments, the HVR1 has at least 70%, at least 80%, or at least 90% identity to the amino acid sequence of SEQ ID NO:15. In some embodiments, the HVR2 comprises the sequence of SEQ ID NO:16 in which 1, 2, 3, or 4 amino acid are substituted, e.g., conservatively substituted. In some embodiments, the HVR2 comprises the sequence of SEQ ID NO:16 in which 1, 2, or 3 amino acids; or 1 or 2 amino acids are substituted, e.g., conservatively substituted. In some embodiments, the HVR has at least 70%, at least 80%, or at least 90% identity to the amino acid sequence of SEQ ID NO:16.

In some embodiments, an anti-SIRPA antibody comprises a heavy chain variable region comprising an HVR3 of SEQ ID NO:17, an HVR1 of SEQ ID NO:15, and an HVR2 of SEQ ID NO:16.

In some embodiments, an anti-SIRPA antibody comprises a light chain variable region that comprises an HVR3 of antibody 9C2 as set forth in Table 2. In some embodiments, the HVR3 comprises the sequence the sequence set forth in SEQ ID NO:14 in which 1, 2, 3, or 4 amino acids are substituted, e.g., conservatively substituted. In some embodiments, the HVR3 comprises the sequence set forth in SEQ ID NO:4 in which 1, 2, or 3 amino acids are substituted, e.g., conservatively substituted. In some embodiments the HVR3 has 1 or 2 amino acid substituted compared to the sequence set forth in SEQ ID NO:14. In some embodiments, 1 or 2 amino acids are deleted, relative to SEQ ID NO:14. In some embodiments, the HVR3 has at least 65% identity to the amino acid sequence of SEQ ID NO:14. In some embodiments, the HVR3 has at least 85% identity to the amino acid sequence of SEQ ID NO:14.

In some embodiments, a light chain variable region of an anti-SIRPA antibody of the invention comprises an HVR3 as set forth in the preceding paragraph and an HVR1 and/or an HVR2 of antibody 9C2 as set forth in Table 2. In some embodiments, the HVR1 comprises the sequence of SEQ ID NO:12 in which 1, 2, 3, or 4 amino acid are substituted, e.g., conservatively substituted. In some embodiments, the HVR1 comprises the sequence of SEQ ID NO:12 in which 1, 2, or 3 amino acids; or 1 or 2 amino acids, are substituted, e.g., conservatively substituted. In some embodiments, the HVR1 has at least 70% identity, at least 80% identity, or at least 90% identity to the amino acid sequence of SEQ ID NO:12. In some embodiments, the HVR2 comprises the sequence of SEQ ID NO:13 in which 1, 2, or 3 amino acids; or 1 or 2 amino acids are substituted, e.g., conservatively substituted. In some embodiments, the HVR2 has at least 70%, at least 85%, identity to the amino acid sequence of SEQ ID NO:13.

In some embodiments, an anti-SIRPA antibody comprises a light chain variable region having an HVR3 of SEQ ID NO:14, an HVR1 of SEQ ID NO:12, and an HVR2 of SEQ ID NO:13.

In some embodiments, an anti-SIRPA antibody of the present disclosure comprises a heavy chain variable region comprising an HVR3, HVR2, and HVR1 of antibody 9C2 as set forth in Table 3 and a light chain variable region comprising an HVR3, HVR2, and HVR1 of antibody 9C2 as set forth in Table 2. In some embodiments, an anti-SIRPA antibody comprises at least one HVR that differs from the HVR of 9C2 by one, two or three amino acids; or one or two amino acids, compared to the corresponding HVR of 9C2. In some embodiments, such an antibody comprises two HVRs that differ from the corresponding HVR of 9C2 by one, two, or three amino acids; or one or two amino acids, compared to the corresponding HVR in of 9C2. In some embodiments, the antibody comprises three HVRs that differ from the corresponding HVR of 9C2 by one, two, or three amino acids; or one or two amino acids, compared to the corresponding HVR in of 9C2. In some embodiments, the antibody comprises four HVRs that differ from the corresponding HVR of 9C2 by one, two, or three amino acids; or one or two amino acids, compared to the corresponding HVR in of 3F9. In some embodiments, the antibody comprises five HVRs that differ from the corresponding HVR of 9C2 by one, two, or three amino acids; or one or two amino acids, compared to the corresponding HVR in of 9C2. In some embodiments, the antibody comprises one, two, or 3 amino acid changes; or one or two amino acid changes, in each HVR compared to the corresponding HVR of 9C2.

In some embodiments, an N residue present in a light chain CDR2 (SEQ ID NO:7) from 3F9 may be substituted with Q, S, A, or D. In some embodiments, the N residue in a light chain CDR3 (SEQ ID NO:8) from 3F9 in Table 2 may be substituted with Q, S, A, or D. In some instances, the N residues in both the light chain CDR2 and CDR3 are substituted with Q, S, A, or D. In some embodiments, the C in a light chain CDR3 (SEQ ID NO:8) from 3F9 may be substituted with an A, S, or L.

In some embodiments, an N residue present in a heavy chain CDR1 (SEQ ID NO:15) from 9C2 may be substituted with Q, S, or A. In some embodiments, one or both N residues present in a heavy chain CDR2 (SEQ ID NO:16) from 9C2 may be substituted with Q, S, or A. In some embodiments, the D of a heavy chain CDR3 residues Asp-Gly (DG) of SEQ ID NO:17 may be substituted with an A, S, or E. In some embodiments, an N residue in a light chain CDR2 (SEQ ID NO:13) from 9C2 may be substituted with Q, S, D, or A. In some embodiments, an N residue in a light chain CDR3 (SEQ ID NO:14) from 9C2 may be substituted with Q, S, D, or A. A light chain CDR3 of SEQ ID NO:14 may also contain a H, Y, or F residue substituted for the Trp residue in the 9C2 light chain CDR3.

Antibody Frameworks

Any of the antibodies described herein further include a framework, preferably a human immunoglobulin framework. For example, in some embodiments, an antibody comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

In some embodiments, an antibody of the present disclosure has the binding specificity of 3F9 and comprises heavy chain HVR1, HVR2, and HVR3 sequences as described above, and further, comprises at least one heavy chain framework as shown in FIG. 14A, e.g., hSB-3F9-H1 or hSB-3F9-H2 sequence of FIG. 14A. A "framework" in this context refers to the FR1, FR2, FR3, and FR4 sequences and excludes the CDR sequence. In some embodiments, an anti-SIRPA antibody has a framework that has at least 90%, at least 91%, at least 92%, at least 93%, at least 94%, at least 95%, at least 96%, at least 97%, at least 98%, or at least 99% amino acid sequence identity to a framework shown in FIG. 14A, where the percent identity is determined based on the FR1, FR2, FR3, and FR4 sequences excluding the CDRs.

In some embodiments, an antibody of the present disclosure has the binding specificity of 3F9 and comprises light chain HVR1, HVR2, and HVR3 sequences as described above, and further, comprises at least one light chain framework as shown in FIG. 14B, e.g., an hSB-3F9-L1, hSB-3F9-L2, or hsB-3F9-L3 sequence of FIG. 14B. A "framework" in this context refers to the FR1, FR2, FR3, and FR4 sequences and excludes the CDR sequence. In some embodiments, an anti-SIRPA antibody has a framework that has at least 90%, at least 91%, at least 92%, at least 93%, at least 94%, at least 95%, at least 96%, at least 97%, at least 98%, or at least 99% amino acid sequence identity to a framework shown in FIG. 14B, where the percent identity is determined based on the FR1, FR2, FR3, and FR4 sequences excluding the CDRs.

In some embodiments, an anti-SIRPA antibody of the present disclosure comprises a $V_H$ region and $V_L$ region as set forth in the two preceding paragraphs.

In some embodiments, an antibody of the present disclosure has the binding specificity of 9C2 and comprises heavy chain HVR1, HVR2, and HVR3 sequences as described above, and further, comprises at least one heavy chain framework as shown in FIG. 14C, e.g., the hSB-9C2-H1, hSB-9C2-H2, hSB-9C2-H3, or hSB-9C2-H4 sequence of FIG. 14C. A "framework" in this context refers to the FR1, FR2, FR3, and FR4 sequences and excludes the CDR sequence. In some embodiments, an anti-SIRPA antibody has a framework that has at least 90%, at least 91%, at least 92%, at least 93%, at least 94%, at least 95%, at least 96%, at least 97%, at least 98%, or at least 99% amino acid sequence identity to a framework shown in FIG. 14C, where the percent identity is determined based on the FR1, FR2, FR3, and FR4 sequences excluding the CDRs.

In some embodiments, an antibody of the present disclosure has the binding specificity of 3F9 and comprises light chain HVR1, HVR2, and HVR3 sequences as described above, and further, comprises at least one light chain framework as shown in FIG. 14D, e.g., an hSB-9C2-L1, hSB-9C2-L2, hSB-9C2-L3, or hSB-9C2-L sequence of FIG. 14D. A "framework" in this context refers to the FR1, FR2, FR3, and FR4 sequences and excludes the CDR sequence. In some embodiments, an anti-SIRPA antibody has a framework that has at least 90%, at least 91%, at least 92%, at least 93%, at least 94%, at least 95%, at least 96%, at least 97%, at least 98%, or at least 99% amino acid sequence identity to a framework shown in FIG. 14D, where the percent identity is determined based on the FR1, FR2, FR3, and FR4 sequences excluding the CDRs.

In some embodiments, an anti-SIRPA antibody of the present disclosure comprises a $V_H$ region and $V_L$ region as set forth in the two preceding paragraphs.

In some embodiments an anti-SIRPA antibody of the present invention comprises one or more e substitutions relative to the CDR and framework region sequences shown in FIGS. 10A-10D. In some embodiments, substitutions are conservative substitutions. Illustrative substitutions are provided below:

Amino Acid Substitutions

| Original Residue | Illustrative Substitutions | Frequent Substitution |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

In some embodiments, substitutions may be non-conservative substitutions. Naturally occurring residues are divided into groups based on common side-chain properties:
  (1) hydrophobic: norleucine, met, ala, val, leu, ile;
  (2) neutral hydrophilic: cys, ser, thr;
  (3) acidic: asp, glu;
  (4) basic: asn, gln, his, lys, arg;
  (5) residues that influence chain orientation: gly, pro; and
  (6) aromatic: trp, tyr, phe.
In some embodiments, non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment). In some embodiments, an anti-SIRPA antibody comprises a substitution at one or more C residues of a sequence shown in FIG. 14A-14D.

In some embodiments, an anti-SIRPA antibody may also comprise substitutions at N residues, which are potential deamidation sites. In some embodiments, an anti-SIRPA antibody of the invention comprises a substitution at one or more N residues of a sequence shown in FIG. 14A-14D.

In some embodiments, an anti-SIRPA antibody comprises a substitution at a W residue, as W residues may be susceptible to oxidation. In some embodiments, the substitution is at one or more W residues of a sequence shown in FIG. 14A-14D.

In some embodiments, an anti-SIRPA antibody that contains an Asp-Gly (DG) sequence, which may be susceptible to isoaspartate formation, may have an A or S substituted for a Gly or an E substituted for Asp.

Anti-SIRPA1 Antibody Binding Affinity

An anti-SIRPA of the present disclosure may have nanomolar or even picomolar affinities for SIRPA. In certain embodiments, the dissociation constant ($K_D$) of the antibody is about 0.05 to about 100 nM. For example, $K_D$ of the antibody is any of about 100 nM, about 50 nM, about 10 nM, about 1 nM, about 900 pM, about 800 pM, about 790 pM, about 780 pM, about 770 pM, about 760 pM, about 750 pM, about 740 pM, about 730 pM, about 720 pM, about 710 pM, about 700 pM, about 650 pM, about 600 pM, about 590 pM, about 580 pM, about 570 pM, about 560 pM, about 550 pM, about 540 pM, about 530 pM, about 520 pM, about 510 pM, about 500 pM, about 450 pM, about 400 pM, about 350 pM about 300 pM, about 290 pM, about 280 pM, about 270 pM, about 260 pM, about 250 pM, about 240 pM, about 230 pM, about 220 pM, about 210 pM, about 200 pM, about 150 pM, about 100 pM, or about 50 pM to any of about 2 pM, about 5 pM, about 10 pM, about 15 pM, about 20 pM, or about 40 pM.

In some embodiments, the $K_D$ of an anti-SIRPA for binding to human SIRPA may be about 200 nM or less, about 100 nM or less, about 50 nM or less, about 20 nM or less, about 10 nM or less, about 1 nM or less. In some embodiments, the Kd of an anti-SIRPA antibody for human SIRPA is about 100 pM or less or about 50 pM or less, less than about 10 pM, or less than about 1 pM. In some embodiments, the binding affinity is in the range of about 1 pM to about 200 nM. In some embodiments, the $K_D$ is in the range of about 1 pM to about 100 nM.

In some embodiments, the $K_D$ of an anti-SIRPA antibody for human SIRPA is less than 15 nM, less than 14.5 nM, less than 14 nM, less than 13.5 nM, less than 13 nM, less than 12.9 nM, less than 12.8 nM, less than 12.7 nM, less than 12.6 nM, less than 12.5 nM, less than 12.4 nM, less than 12.3 nM, less than 12.2 nM, less than 12.1 nM, less than 12 nM, less than 11.5 nM, less than 11 nM, less than 10.9 nM, less than 10.8 nM, less than 10.7 nM, less than 10.6 nM, less than 10.5 nM, less than 10.4 nM, less than 10.3 nM, less than 10.2 nM, less than 10.1 nM, less than 10 nM, less than 9.5 nM, less than 9 nM, less than 8.5 nM, less than 8 nM, less than 7.5 nM, less than 7 nM, less than 6.9 nM, less than 6.8 nM, less than 6.7 nM, less than 6.6 nM, less than 6.5 nM, less than 6.4 nM, less than 6.3 nM, less than 6.2 nM, less than 6.1 nM, less than 6 nM, less than 5.5 nM, less than 5 nM, less than 4.5 nM, less than 4 nM, less than 3.5 nM, less than 3.4 nM, less than 3.3 nM, less than 3.2 nM, less than 3.1 nM, less than 3 nM, less than 2.9 nM, less than 2.8 nM, less than 2.7 nM, less than 2.6 nM, less than 2.5 nM, less than 2.4 nM, less than 2.3 nM, less than 2.2 nM, less than 2.1 nM, less than 2 nM, less than 1.9 nM, less than 1.8 nM, less than 1.7 nM, less than 1.6 nM, less than 1.5 nM, less than 1.4 nM, less than 1.3 nM, less than 1.2 nM, less than 1.1 nM, less than 1 nM, less than 0.95 nM, or less than 0.9 nM. In some embodiments, dissociation constants range from about 50 nM to about 100 pM.

Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses.

Antibody Fragments

Certain aspects of the present disclosure relate to a fragment of a SIRPA antibody as described herein where the fragment retains SIRPA binding activity. In some embodiments, the antibody fragment is an Fab, Fab', Fab'-SH, F(ab')$_2$, Fv or scFv fragment. In some embodiments, an antibody fragment is provided in a multivalent format.

Multivalent Antibodies.

In some embodiments, an anti-SIRPA antibody of the present invention may be in a multivalent format that is internalized faster than a bivalent antibody by a cell expressing an antigen to which the antibodies bind. The anti-SIRPA antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In typical embodiments, the dimerization domain comprises an Fc region or a hinge region. In this scenario, the antibody will comprise an Fc region and three or more antigen binding sites amino-terminal to the Fc region. In some embodiments, a multivalent antibody contains three to eight, e.g., four, antigen binding sites. The multivalent antibody contains at least one polypeptide chain (and preferably two polypeptide chains), wherein the polypeptide chain or chains comprise two or more variable domains.

Bispecific and Multi-Specific Antibodies

Certain aspects of the present disclosure relate to bispecific antibodies, or multi-specific antibodies that comprise an anti-SIRPA antibody as described herein and an antibody that binds to a second antigen or a second SIRPA epitope. Bispecific and multi-specific antibodies may be generated using any method.

In some embodiment, the antibody is a bispecific antibody comprising a variable region of an anti-SIRPA antibody as described in the present disclosure and an antibody that binds to a second antigen. In some embodiments the second antigen is a protein selected from the group consisting of PD1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, or CD73. In some embodiments, the second antigen is an antigen facilitating transport across the blood-brain-barrier; an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; a disease-causing agent selected from the group consisting of disease-causing peptides or proteins or, disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; or ligands and/or proteins expressed on immune cells, wherein the ligands and/or proteins selected from the group consisting of PD1/PDL1, CD40, OX40, ICOS, CD28, CD137/4-

1BB, CD27, GITR, PD-L1, CTLA4, PD-L2, PD-1, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, CD73, and phosphatidylserine; and a protein, lipid, polysaccharide, or glycolipid expressed on one or more tumor cells.

Fc Regions

In some embodiments, an antibody of the present disclosure comprises an Fc region. For example, the antibody may be of the IgG class, the IgM class, or the IgA class. In some embodiments, the has an IgG1, IgG2, IgG3, or IgG4 isotype. Typically, the Fc region is a native human Fc region or variant thereof.

In some embodiments, anti-SIRPA antibodies of the present disclosure retain the ability to bind Fc gamma receptors. In some embodiments, such antibodies may have features that result in clustering and transient stimulation of SIRPA. Such antibodies may subsequently act as longer-term inhibitors of SIRPA expression and/or one or more activities of SIRPA by inducing SIRPA degradation, SIRPA desensitization, SIRPA cleavage, SIRPA internalization, SIRPA shedding, lysosomal degradation of SIRPA or otherwise down-regulating SIRPA. In some embodiments, anti-SIRPA antibodies decrease the level of Fc gamma receptors on the surface of cells.

In some embodiments, the Fc region is an Fc region that binds receptors such as FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (see, e.g., M. Daeron, Annu. Rev. Immunol. 15:203-234 (1997)). FcRs are reviewed in Ravetch and Kinet, Annu. Rev. Immunol. 9:457-92 (1991); Capel et al., Immunomethods 4:25-34 (1994); and de Haas et al., J. Lab. Clin. Med. 126: 330-41 (1995). FcRs can also increase the serum half-life of antibodies.

An Fc region can include one or more mutations that influence activity of the Fc region, e.g., in binding an Fc receptor.

In some embodiments, an antibody of the present disclosure binds an inhibitory Fc receptor. In certain embodiments, the inhibitory Fc receptor is inhibitory Fc-gamma receptor IIB (FcγIIB). In some embodiments, an antibody of the present disclosure decreases the level of expression of inhibitory Fc-gamma receptor JIB on the surface of cells. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A (Alegre et al., (1994) Transplantation 57:1537-1543. 31; Xu et al., (2000) Cell Immunol, 200:16-26), G237A (Cole et al. (1999) Transplantation, 68:563-571), H268Q, V309L, A330S, P331S (US 2007/0148167; Armour et al. (1999) Eur J Immunol 29: 2613-2624; Armour et al. (2000) The Haematology Journal 1(Suppl.1):27; Armour et al. (2000) The Haematology Journal 1(Suppl.1):27), C232S, and/or C233S (White et al. (2015) Cancer Cell 27, 138-148), S267E, L328F (Chu et al., (2008) Mol Immunol, 45:3926-3933), M252Y, S254T, and/ or T256E, where the amino acid position is according to the EU or Kabat numbering convention.

In some embodiments, an antibody of the invention has an IgG2 isotype with a heavy chain constant domain that in some embodiments, contains a C127S or C2214S amino acid substitution, where the amino acid position is according to the EU or Kabat numbering convention (White et al., (2015) Cancer Cell 27, 138-148; Lightle et al., (2010) PROTEIN SCIENCE 19:753-762; and WO2008079246).

In certain embodiments, an antibody of the present disclosure has an IgG1 isotype. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, an antibody of the present disclosure decreases the level of inhibitory Fc-gamma receptor IIB expressed on the surface of cells. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A (Bolt S et al. (1993) Eur J Immunol 23:403-411), D265A (Shields et al. (2001) R. J. Biol. Chem. 276, 6591-6604), D270A, L234A, L235A (Hutchins et al. (1995) Proc Natl Acad Sci USA, 92:11980-11984; Alegre et al., (1994) Transplantation 57:1537-1543. 31; Xu et al., (2000) Cell Immunol, 200:16-26), G237A (Alegre et al. (1994) Transplantation 57:1537-1543. 31; Xu et al. (2000) Cell Immunol, 200:16-26), P238D, L328E, E233D, G237D, H268D, P271G, A330R, C226S, C229S, E233P, L234V, L234F, L235E (McEarchern et al., (2007) Blood, 109:1185-1192), P331S (Sazinsky et al., (2008) Proc Natl Acad Sci USA 2008, 105:20167-20172), S267E, L328F, A330L, M252Y, S254T, T256E, N297Q, P238S, P238A, A327Q, A327G, P329A, K322A, and/or T394D, where the amino acid position is according to the EU or Kabat numbering convention.

In some embodiments, an antibody of the present disclosure has an IgG1 isotype and includes an IgG2 isotype heavy chain constant domain 1 (CH1) and hinge region (White et al., (2015) Cancer Cell 27, 138-148). In certain embodiments, the IgG2 isotype CH1 and hinge region contain the amino acid sequence of ASTKGPSVFPLAPCSRSTSES-TAALGCLVKDYFPEPVTVSWNSGALTSGVHTFPAV LQ SSGLYSLSSVVTVPSSNFGTQTYTCNVDHKPS NTKVDKTVERKCCVECPPCP (SEQ ID NO:34). In some embodiments, the antibody Fc region contains a S267E amino acid substitution, a L328F amino acid substitution, or both, and/or a N297A or N297Q amino acid substitution, where the amino acid position is according to the EU or Kabat numbering convention.

In some embodiments, an anti-SIRPA antibody has an IgG2 isotype and comprises one or more amino acid substitutions in the Fc region at a residue position selected from the group consisting of: P238S, V234A, G237A, H268A, H268Q, V309L, A330S, P331S, C214S, C232S, C233S, S267E, L328F, M252Y, S254T, T256E, H268E, N297A, N297Q, A330L, and any combination thereof, wherein the numbering of the residues is according to EU numbering;

In certain embodiments, an antibody of the present disclosure has an IgG4 isotype. In some embodiments, the contains a human IgG4 constant region and comprises an Fc region that contains one or more amino acid substitutions (e.g., relative to a wild-type Fc region of the same isotype). In some embodiments, the one or more amino acid substitutions are selected from L235A, G237A, S228P, L236E (Reddy et al., (2000) J Immunol, 164:1925-1933), S267E, E318A, L328F, M252Y, S254T, T256E, E233P, F234V, L234A/F234A, S228P, S241P, L248E, T394D, N297A, N297Q, L235E, and any combination thereof, wherein the numbering of the residues is according to EU numbering In some embodiments, an anti-SIRPA antibody of the present disclosure has a hybrid IgG2/4 isotype. In certain embodiments the antibody comprises an amino acid sequence comprising amino acids 118 to 260 of human IgG2 and amino acids 261 to 447 of human IgG4, wherein the numbering of the residues is according to EU numbering.

In some embodiments, an anti-SIRPA antibody of the present disclosure has a human or mouse IgG1 isotype and comprises one or more amino acid substitutions in the Fc region at a residue position selected from the group consisting of: N297A, N297Q, D270A, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof, wherein the numbering of the residues is according to EU numbering.

In some embodiments, an anti-SIRPA antibody of the present disclosure has an IgG2 isotype and comprises one or more amino acid substitutions in the Fc region at a residue position selected from the group consisting of: P238S, V234A, G237A, H268A, H268Q, H268E, V309L, N297A, N297Q, A330S, P331S, C232S, C233S, M252Y, S254T, T256E, and any combination thereof, wherein the numbering of the residues is according to EU numbering.

In some embodiments, an anti-SIRPA antibody of the present disclosure has an IgG4 isotype and comprises one or more amino acid substitutions in the Fc region at a residue position selected from the group consisting of: E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU numbering.

In some embodiments, an anti-SIRPA antibody of the present disclosure comprises an Fc region that further comprises one or more additional amino acid substitutions at a position selected from the group consisting of A330L, L234F; L235E, P331S, and any combination thereof, wherein the numbering of the residues is according to EU numbering.

In some embodiments, an anti-SIRPA antibody of the present disclosure comprises an Fc region that further comprises one or more additional amino acid substitutions at a position selected from the group consisting of M252Y, S254T, T256E, and any combination thereof, wherein the numbering of the residues is according to EU numbering.

In some embodiments, an anti-SIRPA antibody of the present disclosure comprises an Fc region that further comprises a S228P amino acid substitution according to EU numbering.

In some embodiments, an anti-SIRPA antibody of the present disclosure has an IgG4 isotype and comprises an S228P amino acid substitution at residue position 228, an F234A amino acid substitution at residue position 234, and an L235A amino acid substitution at residue position 235, wherein the numbering of the residue position is according to EU numbering In some embodiments, an anti-SIRPA antibody of the present disclosure may be modified to modulate effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII to reduce antibody-dependent cell-mediated cytotoxicity. In some embodiments, the effector function is inhibited by removing N-glycosylation of the Fc region (e.g., in the CH 2 domain of IgG) of the antibody. In some embodiments, the effector function is inhibited by modifying regions such as 233-236, 297, and/or 327-331 of human IgG as described in PCT WO 99/58572 and Armour et al., Molecular Immunology 40: 585-593 (2003); Reddy et al., J. Immunology 164:1925-1933 (2000). In other embodiments, it may also be desirable to modify an anti-SIRPA antibody of the present disclosure to modify effector function to increase binding selectivity toward the ITIM-containing FcγRIIb (CD32b) to increase clustering of SIRPA antibodies on adjacent cells without activating effector functions such as ADCC.

In some embodiments, to increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Other Amino Acid Sequence Modifications

Amino acid sequence modifications of anti-SIRPA antibodies of the present disclosure, or antibody fragments thereof, are also contemplated. For example, it may be desirable to improve the binding affinity and/or other biological properties of the antibodies or antibody fragments.

In some embodiments, additional amino acid sequences can be fused to the amino terminal or carboxy terminal of an anti-SIRPA antibody. Examples include, but are not limited to, an antibody with an N-terminal methionyl residue, fusion to a cytotoxic polypeptide, or fusion to an enzyme or a polypeptide that increases the serum half-life of the antibody.

In some embodiments, an antibody of the present invention may be mutated to alter the original glycosylation patter of the antibody, e.g., by deleting one mutating or more sites to prevent glycosylation by certain carbohydrate moieties and/or adding one or more glycosylation sites to introduce desired carbohydrate moieties.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Other Antibody Modifications

Anti-SIRPA antibodies of the present disclosure, or antibody fragments thereof, can be further modified to contain additional moieties, e.g., moieties for derivatization of the antibody, drug moieties to be conjugated to the antibody and the like. Examples of moieties suitable for derivatization of an antibody are water-soluble polymers such as polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in Remington: The Science and Practice of Pharmacy, 20th Ed., Alfonso Gennaro, Ed., Philadelphia College of Pharmacy and Science (2000).

In some embodiments, a cyotoxic agent or drug may be conjugated to an anti-SIRPA antibody of the present invention, e.g., for the treatment of cancers, such as multiple myeloma or other cancers, that express SIRPA on the cell surface. Techniques to conjugate antibodies are disclosed are known in the art (see, e.g., Jane de Lartigue, OncLive Jul. 5, 2012; ADC Review on antibody-drug conjugates; and Ducry et al., (2010). Bioconjugate Chemistry 21 (1): 5-13). In some embodiments, the anti-SIRPA antibody is conjugated to a toxin selected from the group consisting of ricin, ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin.

Nucleic Acids, Vectors, and Host Cells

Anti-SIRPA antibodies of the present disclosure are commonly produced using recombinant methods. Accordingly, in some aspects, the invention provides, isolated nucleic acids comprising a nucleic acid sequence e encoding any of the anti-SIRPA antibodies as described herein; vectors comprising such nucleic acids and host cells into which the nucleic acids are introduced that are used to replicate the antibody-encoding nucleic acids and/or to express the antibodies. Such nucleic acids may encode an amino acid sequence containing the $V_L$ and/or an amino acid sequence containing the $V_H$ of the anti-SIRPA antibody (e.g., the light and/or heavy chains of the antibody). In some embodiments, the host cell contains (1) a vector containing a polynucleotide that encodes the $V_L$ amino acid sequence and a polynucleotide that encodes the $V_H$ amino acid sequence, or (2) a first vector containing a polynucleotide that encodes the $V_L$ amino acid sequence and a second vector containing a polynucleotide that encodes the $V_H$ amino acid sequence. In some embodiments, the host cell is eukaryotic, e.g., a Chinese Hamster Ovary (CHO) cell; or a human cell. In some embodiments, the host cell is a lymphoid cell (e.g., Y0, NS0, Sp20 cell). Host cells of the present disclosure also include, without limitation, isolated cells, in vitro cultured cells, and ex vivo cultured cells.

In a further aspect, the invention provides a method of making an anti-SIRPA antibody as described herein. In some embodiments, the method includes culturing a host cell as described in the preceding paragraph under conditions suitable for expression of the antibody. In some embodiments, the antibody is subsequently recovered from the host cell (or host cell culture medium).

Suitable vectors containing polynucleotides encoding antibodies of the present disclosure, or fragments thereof include cloning vectors and expression vectors. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, and any other vector.

Suitable host cells for expressing an anti-SIRPA antibody as described herein include both prokaryotic or eukaryotic cells. For example, anti-SIRPA antibodies may be produced in bacteria, in particular when glycosylation and Fc effector function are not needed. After expression, the antibody may be isolated from the bacterial cell paste in a soluble fraction and can be further purified. Alternatively, the host cell may be a eukaryotic host cell, including eukaryotic microorganisms, such as filamentous fungi or yeast, including fungi and yeast strains whose glycosylation pathways have been "humanized," resulting in the production of an antibody with a partially or fully human glycosylation pattern, vertebrate, invertebrate, and plant cells. Examples of invertebrate cells include insect cells. Numerous baculoviral strains have been identified which may be used in conjunction with insect cells. Plant cell cultures can also be utilized as host cells.

In some embodiments, vertebrate host cells are used for producing anti-SIRPA antibodies of the present disclosure. For example, mammalian cell lines such as a monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells may be used to express anti- SIRPA antibodies. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Pharmaceutical Composition and Treatment Using an Anti-SIRPA Antibody

Pharmaceutical Compositions

Anti-SIRPA antibodies can be incorporated into a variety of formulations for therapeutic administration by combining the antibodies with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's Pharmaceutical Sciences, Mace Publishing Company, Philadelphia, Pa., 22nd ed. (2012).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-SIRPA antibody of the present disclosure, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may have the active agent distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical compositions of the present disclosure containing an anti-SIRPA antibody of the present disclosure may be administered to an individual in need of treatment with the anti-SIRPA antibody, preferably a human, in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the anti-SIRPA antibodies of the present disclosure, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease, disorder, or condition to be treated, the treatment is sustained until a desired suppression of symptoms is achieved.

An exemplary dosing regimen may include administering an initial dose of an anti-SIRPA antibody, of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-SIRPA antibody administered, can vary over time independently of the dose used.

Dosages for a particular anti-SIRPA antibody may be determined empirically in individuals who have been given one or more administrations of the anti-SIRPA antibody. Individuals are given incremental doses of an anti-SIRPA antibody. To assess efficacy of an anti-SIRPA antibody, a clinical symptom of the diseases, disorders, or conditions of the present disclosure (e.g., cancer) can be monitored.

Administration of an anti-SIRPA antibody of the present disclosure can be continuous or intermittent, depending, for example, on the recipient's physiological condition, whether the purpose of the administration is therapeutic or prophylactic, and other factors known to skilled practitioners. The administration of an anti-SIRPA antibody may be essentially continuous over a preselected period of time or may be in a series of spaced doses.

It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

In one aspect of the invention, an agent that down-regulates SIRPA, e.g., an anti-SIRPA antibody, is used as a therapeutic agent. Such agents are administered to treat, alleviate, and/or prevent a disease or pathology associated with SIRPA expression, activity and/or signaling in a subject. A therapeutic regimen is carried out by identifying a subject, e.g., a human patient suffering from (or at risk of developing) a disease or disorder associated with SIRPA expression, activity and/or signaling, e.g., a cancer or other neoplastic disorder, using standard methods. In some embodiments, cells having the pathology associated with SIRPA expression, activity, and/or signaling, express a SIRPA ligand, e.g., CD47. In some embodiments, cells having the pathology associated with SIRPA expression, activity, and/or signaling, express SIRPA.

As further detailed below an agent that down-regulates SIRPA, e.g., an anti-SIRPA antibody can be used in combination with an additional therapeutic agent that is used to treat the disease or pathology associated with SIRPA expression, activity, or signaling. The terms "in combination" and "in conjunction" are used interchangeably in the present disclosure. The additional therapeutic agent may be administered before, after, or concurrently with the agent that down-regulates SIRPA, e.g., an anti-SIRPA antibody.

In one aspect of the present disclosure, an anti-SIRPA antibody preparation, e.g., comprising an anti-SIRPA antibody that decreases expression of SIRPA on the cell surface, but does not substantially block binding of ligand, e.g., CD47, to SIRPA, is administered to a human subject. Administration of the antibody may abrogate or inhibit or interfere with the expression, activity and/or signaling function of SIRPA that is mediated by ligand binding, e.g., CD47 binding. In one embodiment the disease or disorder associated with SIRPA expression is cancer. In some embodiments, an anti-SIRPA antibody is administered to a patient that has a cancer, such as a hematological proliferative disorder of myeloid cells, that express SIRPA. In typical embodiments, an anti-SIRPA antibody is administered to a patient that has a cancer that expresses CD47.

In certain embodiments, the cancer is squamous cell carcinoma, small-cell lung cancer, non-small cell lung cancer, squamous non-small cell lung cancer (NSCLC), non-squamous NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyosarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. Anti-SIRPA antibodies of the present invention may also be used to treat metastatic cancer.

In some embodiments, the cancer is selected from the group consisting of sarcoma, bladder cancer, brain cancer, breast cancer, colon cancer, rectal cancer, endometrial cancer, kidney cancer, renal pelvis cancer, leukemia, lung cancer, melanoma, lymphoma, pancreatic cancer, prostate cancer, ovarian cancer, and fibrosarcoma.

In some embodiments, the cancer is selected from the group consisting of glioblastoma multiforme; renal clear cell carcinoma; adrenocortical carcinoma; bladder urothelial carcinoma; diffuse large B-cell lymphoma; lung adenocarcinoma; pancreatic adenocarcinoma, renal cell cancer, non-Hodgkin's lymphoma, acute lymphoblastic leukemia (ALL), acute myeloid leukemia (AML), chronic lymphocytic leukemia (CLL), chronic myeloid leukemia (CML), multiple myeloma, breast invasive carcinoma, cervical squamous cell carcinoma, endocervical adenocarcinoma, cholangiocarcinoma, colon adenocarcinoma, diffuse large B-cell lymphoma, esophageal carcinoma, head and neck squamous cell carcinoma, kidney chromophobe, renal papillary cell carcinoma, lower grade glioma, hepatocellular carcinoma, lung squamous cell carcinoa, mesothelioma, ovarian serous cystadenomcarcinoma, pancreatic adenocarcinoma, pheochromocytoma and paraganglioma, prostate adenocarconimo, rectal adenocarcinoma, cutaneous melanoma, stomach adenocarcinoma, testicular germ cell tumors, thyroid carcinoma, thyumoma, uterine corpus endometrial carcinoma, uternine carcinosarcoma, and uveal melanoma.

In some embodiments, an anti-SIRPA antibody of the present disclosure may be administered in conjunction with a therapeutic agent that acts as a checkpoint inhibitor. In some embodiments, the checkpoint inhibitor targets PD1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, and CD73. In typical embodiments, the therapeutic agent is an antibody to a checkpoint inhibitor selected from D1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, or CD73. In some embodiments, a combination of antibodies to checkpoint inhibitors is administered in conjunction in an anti-SIRPA antibody of the present invention.

In some embodiments, an anti-SIRPA antibody of the present disclosure may be administered in conjunction with at least one agonistic antibody that specifically binds to a stimulatory checkpoint protein, e.g., an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, an agonist anti-CD30 antibody, an agonist anti-BTLA antibody, an agonist anti-HVEM antibody, an agonist anti-CD2 antibody, an agonist anti-CD5 antibody, and any combination thereof.

In some embodiments, an anti-SIRPA antibody of the present invention is administered in combination with radiation therapy and/or a chemotherapeutic agents. Chemotherapeutic agents include, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (methotrexate, pemetrexed, mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones, eribulin and navelbine; epidipodophyllotoxins (etoposide, teniposide); DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); DNA methyltransferase inhibitors (azacytidine); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkylsulfonates (busulfan), nitrosoureas (carmustine (BCNU) and analogs, streptozocin), triazenes (dacarbazine (DTIC)); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein, pomalidomide) and growth factor inhibitors (vascular endothelial growth factor (VEGF) inhibitors, such as ziv-aflibercept; fibroblast growth factor (FGF) inhibitors); inhibitors of apoptosis protein (IAP) antagonists (birinapant); histone deacetylase (HDAC) inhibitors (vorinostat, romidepsin, chidamide, panobinostat, mocetinostat, abexinostat, belinostat, entinostat, resminostat, givinostat, quisinostat, SB939); proteasome inhibitors (ixazomib); angiotensin receptor blocker; nitric oxide donors; anti-sense oligonucleotides; antibodies (trastuzumab, panitumumab, pertuzumab, cetuximab, adalimumab, golimumab, infliximab, rituximab, ocrelizumab, ofatumumab, obinutuzumab, alemtuzumab, abciximab, atlizumab, daclizumab, denosumab, efalizumab, elotuzumab, rovelizumab, ruplizumab, ustekinumab, visilizumab, gemtuzumab ozogamicin, brentuximb vedotin); chimeric antigen receptors; cell cycle inhibitors (flavopiridol, roscovitine, bryostatin-1) and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); PARP inhibitors (niraparib, olaparib); focal adhesion kinase (FAK) inhibitors (defactinib (VS-6063), VS-4718, VS-6062, GSK2256098); growth factor signal transduction kinase inhibitors (cediranib, galunisertib, rociletinib, vandetanib, afatinib, EGF816, AZD4547); c-Met inhibitors (capmatinib, INC280); ALK inhibitors (ceritinib, crizotinib); mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors. In some embodiments, a chemotherapeutic agent is a B-Raf inhibitor, a MEK inhibitor, a VEGF inhibitor, a VEGFR inhibitor, a tyrosine kinase inhibitor, an anti-mitotic agent, or any combination thereof.

In some embodiments, an anti-SIRPA antibody of the present disclosure is administered in combination with adoptive cell transfer (ACT) therapy, chimeric antigen receptor T cell transfer (CAR-T) therapy, vaccine therapy, and/or cytokine therapy.

In some embodiments, an anti-SIRPA antibody of the present disclosure is administered in combination with at least one antibody that specifically binds to an inhibitory cytokine, e.g., an inhibitory cytokine such as an anti-CCL2 antibody, an anti-CSF-1 antibody, or an anti-IL-2 antibody.

In some embodiments, an anti-SIRPA antibody of the present disclosure is administered in combination with at least one stimulatory cytokine. In some embodiments that may be combined with any of the preceding embodiments, the at least one stimulatory cytokine is selected from the group consisting of IFN-α4, IFN-β, TNF-α, IL-6, IL-8, CRP, IL-20 family members, LIF, IFN-γ, OSM, CNTF, GM-CSF, IL-11, IL-12, IL-15, IL-17, IL-18, IL-23, CXCL10, IL-33, MCP-1, MIP-1-beta, and any combination thereof.

In some embodiments, an agent that down-regulates SIRPA, e.g., an anti-SIRPA antibody, is administered to a patient that has a neurological disorder, or is administered to reduce risk, slow onset, or prevent a neurological disorder. In some embodiments, the neurological disorder is dementia, including frontotemporal dementia, Alzheimer's disease, or vascular dementia. In some embodiments, the patient has mild cognitive impairment.

In some embodiments, an agent that down-regulates SIRPA, e.g., an anti-SIRPA antibody, is administered to a patient that has Parkinson's disease, amyotrophic lateral sclerosis, Huntington's disease, Taupathy diseases, or multiple sclerosis. In some embodiments, the agent is administered to a patient that has Creutzfeldt-Jakob disease, normal pressure hydrocephalus, Nasu-Hakola disease, stroke, an infection, traumatic brain injury, progressive supranuclear palsy, dementia pugilistica (chronic traumatic encephalopathy), Parkinsonism linked to chromosome 17, Lytico-Bodig disease (Parkinson-dementia complex of Guam), tangle-predominant dementia, ganglioglioma and gangliocytoma, meningioangiomatosis, subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), frontotemporal lobar degeneration, dementia with Lewy bodies, multiple system atrophy, Shy-Drager syndrome, progressive supranuclear palsy, or cortical basal ganglionic degeneration.

EXAMPLES

The following examples are provided by way of illustration only and not by way of limitation. Those of skill in the art will readily recognize a variety of non-critical parameters that could be changed or modified to yield essentially similar results.

Example 1: Production of Anti-SIRPA Antibodies

The amino acid sequence of the human SIRPA preprotein is set forth below in SEQ ID NO:1. Human SIRPA contains a signal peptide located at amino residues 1-30 of SEQ ID NO:1. Human SIRPA contains an extracellular immunoglobulin-like variable-type (IgV) domain located at amino residues 32-137 of SEQ ID NO:1; additional extracellular immunoglobulin-like constant-type (IgC) domain sequences located at amino residues 148-247 and 254-348 of SEQ ID NO:1; a transmembrane domain located at amino residues 374-394 of SEQ ID NO:1; and an intracellular domain located at amino residues 395-504 of SEQ ID NO:1.

```
SIRPAv1 amino acid sequence (SEQ ID NO: 1):
            10         20         30         40         50
    MEPAGPAPGR LGPLLCLLLA ASCAWSGVAG EEELQVIQPD KSVLVAAGET 60         70         80         90        100
    ATLRCTATSL IPVGPIQWFR GAGPGRELIY NQKEGHFPRV TTVSDLTKRN 110        120        130        140        150
    NMDFSIRIGN ITPADAGTYY CVKFRKGSPD DVEFKSGAGT ELSVRAKPSA 160        170        180        190        200
    PVVSGPAARA TPQHTVSFTC ESHGFSPRDI TLKWFKNGNE LSDFQTNVDP 210        220        230        240        250
    VGESVSYSIH STAKVVLTRE DVHSQVICEV AHVTLQGDPL RGTANLSETI 260        270        280        290        300
    RVPPTLEVTQ QPVRAENQVN VTCQVRKFYP QRLQLTWLEN GNVSRTETAS 310        320        330        340        350
    TVTENKDGTY NWMSWLLVNV SAHRDDVKLT CQVEHDGQPA VSKSHDLKVS 360        370        380        390        400
    AHPKEQGSNT AAENTGSNER NIYIVVGVVC TLLVALLMAA LYLVRIRQKK 410        420        430        440        450
    AQGSTSSTRL HEPEKNAREI TQDTNDITYA DLNLPKGKKP APQAAEPNNH 460        470        480        490        500
    TEYASIQTSP QPASEDTLTY ADLDMVHLNR TPKQPAPKPE PSFSEYASVQ

VPRK
```

Crystal structure analyses of SIRPA-CD47 complexes resolve the ligand binding site to the variable loops that link the β-sheet strands in the IgV domain of SIRPA. The CD47-binding interface consists of amino acid residues S59-P65, L96-F104, and K123-D130.

Multiple polymorphisms of SIRPA have been identified in humans. An alignment of the amino acid sequences of the two most common variants, referred to as SIRPA v1 and v2, was generated by 2-way blast (FIG. 1A). Since most variations in sequence lie beyond the ligand binding site, both SIRPA variants are reported to bind CD47 with similar affinities. Alternatively, another member of the SIRP family, SIRPB1, shares high sequence homology with SIRPA but fails to bind CD47. An alignment of the amino acid sequences of SIRPAv1 and SIRPB1 was generated by 2-way blast (FIG. 1B) and shows that the extracellular domain of both proteins (excluding leader sequence) shares ~90% identity. However a single A57M substitution is sufficient to rearrange the S59-P65 ligand-binding interface to prevent SIRPB1 binding to CD47. Furthermore, CD47 binding is highly species-specific with human CD47 recognizing a single allelic variant of mouse SIRPA expressed only by NOD mice. An alignment of the amino acid sequences of human SIRPAv1 and C57BL6 SIRPA was generated by 2-way blast (FIG. 2) and shows that the extracellular domain of both proteins (excluding leader sequence) shares ~60% identity.

Anti-SIRPA Antibody Production

Immunization Procedure

Rapid Prime Method:

Four 50-day old female BALB/c mice were immunized with using the following procedure. A series of subcutaneous aqueous injections containing human SIRPA antigen but no adjuvant were given over a period of 19 days. Mice were housed in a ventilated rack system from Lab Products. All four mice were euthanized on Day 19 and lymphocytes were harvested for hybridoma cell line generation.

Standard Method:

Four 50-day old female BALB/c or NZB/W mice were immunized using the following procedure. Mice were housed in a ventilated rack system from Lab Products. Mice were injected intraperitoneally every 3 weeks with a human SIRPA antigen mixed in CpG-ODN adjuvant at 25 µg protein antigen per mouse (total volume 125 µL per mouse). Test bleeds were done by saphenous vein lancing seven days after the second boost. The test bleed (immune sera) was tested by indirect ELISA assay to determine the best two responding mice for the fusion. The mice may require a 3rd and 4th boost and another test bleed 7 days after boost to assess titre before fusion. When the antibody titre is high enough the best two responding mice are given a final intravenous boost via lateral tail vein. Four days after the IV boost the mice were euthanized for fusion. The spleens were harvested and lymphocytes isolated from the spleen were used in the fusion process to produce hybridomas.

Hybridoma Development

Lymphocytes were isolated and fused with murine SP2/0 myeloma cells in the presence of poly-ethylene glycol (PEG 1500) as per standard Roche Protocol. Fused cells were cultured using a single-step cloning method (HAT selection). This method uses a semi-solid methylcellulose-based HAT selective medium to combine the hybridoma selection and cloning into one step. Single cell-derived hybridomas grow to form monoclonal colonies on the semi-solid media. Ten days after the fusion event, 948 of the resulting hybridoma clones were transferred to 96-well tissue culture plates and grown in HT containing medium until mid-log growth was reached (5 days).

Hybridoma Screening

Tissue culture supernatants from the 948 hybridomas were tested by indirect ELISA on screening antigen (Primary Screening) and probed for both IgG and IgM antibodies using a Goat anti-IgG/IgM(H&L)-HRP secondary and developed with TMB substrate. Clones >0.2 OD in this assay were taken to the next round of testing. Positive cultures were retested on screening antigen to confirm secretion and on an irrelevant antigen (Human Transferrin) to eliminate non-specific or "sticky" mAbs and rule out false positives. All clones of interest were isotyped by antibody trapping ELISA to determine if they are IgG or IgM isotype.

Hybridoma Cell Culture

The hybridoma cell lines of interest were maintained in culture in 24-well culture plates for 32 days post transfer to 96-well plates. This is referred to as the stability period and tests whether clones remain stable and secreting. During this stability period time temporary frozen cell line back up is made of all the clones of interest for −80° C. storage (viable 6 months). Hybridomas were periodically tested during this time period for secretion and specificity.

Subcloning

The top hybridoma cell lines (clones) were subcloned to ensure monoclonality. Subcloning was performed by plating parental clones out again using the single-step cloning system. Between 24 and 90 subclones were transferred to 96-well culture plates. Subclones were screened by indirect ELISA and antibody trapping ELISA. The top subclones for each parent were taken for expansion in culture. Any parental clones that were <50% clonal had a second round of subcloning performed.

The antibodies were then screened for SIRPA binding. Antibodies that were positive for binding to human SIRPA were tested for ability to block ligand binding and ability to inhibit ligand-induced SIRPA activity in multiple cell types. The isotype and bin category of each of the antibodies are listed in Table 1. In Table 1, "ND" refers to antibodies for which the Bin category has not been determined.

TABLE 1

Isotype and epitope bin category for anti-human SIRPA antibodies

| AB ID | Isotype | Bin |
|-------|---------|-----|
| 3F9   | mIgG1   | 3   |
| 9C2   | mIgG1   | 3   |
| 8A9   | mIgG    | 3   |
| 12D6  | mIgG    | 1   |
| 8F4   | mIgG    | 2   |
| 1E2   | mIgG    | 2   |
| 7H9   | mIgG    | 2   |
| 4D8   | mIgG    | 3   |

Antibody Heavy Chain and Light Chain Variable Domain Sequences

Using standard techniques, the amino acid sequences encoding the light chain variable and the heavy chain variable domains of the generated antibodies were determined. The EU or Kabat light chain HVR sequences of the antibodies are set forth in Table 2-5. The EU or Kabat light chain HVR sequences of the antibodies are set forth in Table 2. The EU or Kabat heavy chain HVR sequences of the antibodies are set forth in Table 3. The EU or Kabat light chain framework (FR) sequences of the antibodies are set forth in Table 4. The EU or Kabat heavy chain framework (FR) sequences of the antibodies are set forth in Table 5.

```
3F9: Heavy chain variable domain sequence
                                       (SEQ ID NO: 2)
EVKLVESGGGLVKPGGSLKLSCAASGFTFSSYAMSWVRQT
PEKRLEWVATISDYGGSYTYYPDSVKGRFTISRDNAKYTLYLQMSSLRSE
DTALYYCARPPYDDYYGGFAYWGQGTLVTVSA 3E2: Light chain variable domain sequence
                                       (SEQ ID NO: 3)
DIVLTQSPASLAVSLGQRATISCRASKSVSSSGYSYMIHWY
QQKPGQPPKWYLASNLESGVPARFSGSGSGTDFTLNIHPVEEEDAATYYC
QHNRELPCTFGGGTKLEIK 9C2: Heavy chain variable domain sequence
                                       (SEQ ID NO: 4)
EFQLQQSGAELVKPGASVKISCKASGYSLTGYNMNWVKQS
RGKSLEWIGNINPHYGSSTYNQNFKDKATLTVDKSSSAAYMQFNSLTSED
SAVYYCAREGYDGVFDYWGQGTTLTVSS
```

9C2: Light chain variable domain sequence
(SEQ ID NO: 5)
QIVLSQSPAILSASPGEKVTMTCRASSSVSYMHWYQQKPG
SSPKPWIYVTSNLASGVPTRFSGSGSGTSYSLTISRVEAEDAATYYCQQW
SSNPRTFGGGTKLEIK 8A9: Heavy chain variable domain sequence
(SEQ ID NO: 35)
QVQLQQPGAELVKPGASVKMSCKASGYTFTSYWMIHWVKQR
PGQGLEWIGVIDPSDSYTNYNQKFKGKATLTVDTSSSTAYMQLSSLTSED
SAVYYCTRSGYGKYDFDYWGQGTTLTVSS 8A9: Light chain variable domain sequence
(SEQ ID NO: 36)
DIVLTQSPASLAVSLGQRATISCRASQSVSTSSYSYMHWY
QQKPGQPPKLLIKYASNLESGVPARFSGSGSGTDFTLNIHPVEEEDTATY
YCQHNWEIPWTFGGGTKLEIK 8F4: Heavy chain variable domain sequence
(SEQ ID NO: 37)
QIQLVQSGPELKKPGETVKISCKASDYTFTDYSMHWVKQA
PGKDLKWMGWINTETGEPTYADDFKGRFAFSLEASASTAYLQINNLKNED
TATYFCARHGYPHYYFDYWGQGTTLTVSS 8F4: Light chain variable domain sequence
(SEQ ID NO: 38)
DIVMTQSQKFMSTSVGDRVSITCKASQNVPTAVAWYQQKP
GQSPKALIYLASNRHTGVPDRFTGSGSGTDFTLTITNVQSEDLADYFCLQ
HWNYPRTFGGGTKLEIK 1E2: Heavy chain variable domain sequence
(SEQ ID NO: 39)
EVQLVESGGDLVKPGGSLKLSCAASGFSFSSYAMSWVRQT
PAKRLEWVATISGSGGYTYYPDSMKGRFTISRDNAKDILYLQMSSLRSED
TAMYYCARDPRYTTLYAMDYWGQGTSVTSS 1E2: Light chain variable domain sequence
(SEQ ID NO: 40)
NIMMTQSPSFLAVSAGEKVTMSCKSSQSIFSGSNQKNYLA
WYQQKPGQSPKLLIYWASTRESGVPDRFTGSGSGTDFTLTISSVQAEDLA
VYYCHQHLSSCTFGGGTKLEIK 7H9: Heavy chain variable domain sequence
(SEQ ID NO: 41)
DVQLQESGPGLVKPSQSLSLTCTVTGFSISRGYDWHWIRH
FPGNILEWMGYITYSGISNYNPSLKSRISITHDTSKNHFFLRLNSVTAED
TATYYCARGGGAWFTYWGQGTLVTVSA 7H9: Light chain variable domain sequence
(SEQ ID NO: 42)
DIVMTQSPATLSVTPGDRVSLSCRASQSISDSLHWYHQKS
HESPRLLIKYASQSISGIPSRFSAGGSGSDFTLTINSVEPEDVGVYYCQN
GHSLPWTFGGGTKLEIK 4D8: Heavy chain variable domain sequence
(SEQ ID NO: 43)
EVKLEESGGGLVKPGGSMKLSCAASGFTFSDAWMDWVRQS
PEKGLEWVAEIRGKTTNYATYYAESVKGRFTISRDDSKSSVYLQMNSFST
EDTGIYYCTRRNWGFAYWGQGTLVTVSA 4D8: Light chain variable domain sequence
(SEQ ID NO: 44)
DILLTQSPAILSVSPGERVSFSCRASQTIGTSIHWYQQRT
NGSPRLLIKYASESISGIPSRFSGSGSGTDFTLSINSVESEDIADYYCQQ
TNSWPLTFGAGTKLELK

TABLE 2

EU or Kabat light chain HVR sequences of anti-SIRPA antibodies

| AB ID | HVR L1 | HVR L2 | HVR L3 |
|---|---|---|---|
| 3F9 | RASKSVSSSGYSY MH (SEQ ID NO: 6) | LASNLES (SEQ ID NO: 7) | QHNRELPCT (SEQ ID NO: 8) |
| 9C2 | RASSSVS-YMH (SEQ ID NO: 12) | VTSNLAS (SEQ ID NO: 13) | QQWSSNPRT (SEQ ID NO: 14) |

TABLE 3

EU or Kabat heavy chain HVR sequences of anti-SIRPA antibodies

| AB ID | HVR H1 | HVR H2 | HVR H3 |
|---|---|---|---|
| 3F9 | GFTFSSYAMS (SEQ ID NO: 9) | TISDYGGSYTY (SEQ ID NO: 10) | PPYDDYYGGFAY (SEQ ID NO: 11) |
| 9C2 | GYSLTGYNMN (SEQ ID NO: 15) | NINPHYGSST (SEQ ID NO: 16) | EGYDGVFDY (SEQ ID NO: 17) |

TABLE 4

EU or Kabat light chain Framework sequences of anti-SIRPA antibodies

| AB ID | VL FR1 | VL FR2 | VL FR3 | VL FR4 |
|---|---|---|---|---|
| 3F9 | DIVLTQSPASLAV SLGQRATISC (SEQ ID NO: 22) | WYQQKPGQPP KLLIY (SEQ ID NO: 23) | GVPARFSGSGSGTD FTLNIHPVEEEDAAT YYC (SEQ ID NO: 24) | FGGGTKLEIK (SEQ ID NO: 25) |

TABLE 4-continued

EU or Kabat light chain Framework sequences of anti-SIRPA antibodies

| AB ID | VL FR1 | VL FR2 | VL FR3 | VL FR4 |
|-------|--------|--------|--------|--------|
| 9C2 | QIVLSQSPAILSAS PGEKVTMTC (SEQ ID NO: 30) | WYQQKPGSSP KPWIY (SEQ ID NO: 31) | GVPTRFSGSGSGTSY SLTISRVEAEDAATY YC (SEQ ID NO: 32) | FGGGTKLEIK (SEQ ID NO: 33) |

TABLE 5

EU or Kabat heavy chain Framework sequences of anti-SIRPA antibodies

| Ab ID | VH FR1 | VH FR2 | VH FR3 | VH FR4 |
|-------|--------|--------|--------|--------|
| 3F9 | EVKLVESGGGLV KPGGSLKLSCAAS (SEQ ID NO: 18) | WVRQTPEKRL EWVA (SEQ ID NO: 19) | YPDSVKGRFTISRDN AKYTLYLQMSSLRS EDTALYYCAR (SEQ ID NO: 20) | WGQGTLVT VSA (SEQ ID NO: 21) |
| 9C2 | EFQLQQSGAELV KPGASVKISCKAS (SEQ ID NO: 26) | WVKQSRGKSL EWIG (SEQ ID NO: 27) | YNQNFKDKATLTV DKSSSAAYMQFNSL TSEDSAVYYCAR (SEQ ID NO: 28) | WGQGTTLT VSS (SEQ ID NO: 29) |

Example 2: Characterization of Anti-SIRPA Antibody

Initial characterization of SIRPA antibodies involved screening their ability to bind the human receptor ectopically expressed on the rodent Chinese hamster ovary cell line, henceforth referred to as CHO-huSIRPA, followed by screening on primary human macrophages. Cells were harvested, plated at $10^5$ cells/well in a 96-well plate, washed, and incubated in 100 µl FACS buffer containing Fc blocking reagent and 1.0 µg/ml of indicated monoclonal antibody. Cells were then washed twice and incubated in FACS buffer containing APC-conjugated secondary antibody diluted 1:200 for 30 minutes on ice. Cells were washed twice in cold FACS buffer and acquired on a BD FACS Canto. Data analysis and calculation of mean fluorescence intensity (MFI) values or % positive cells was performed with FlowJo (TreeStar) software version 10.0.7.

Figure 3B:
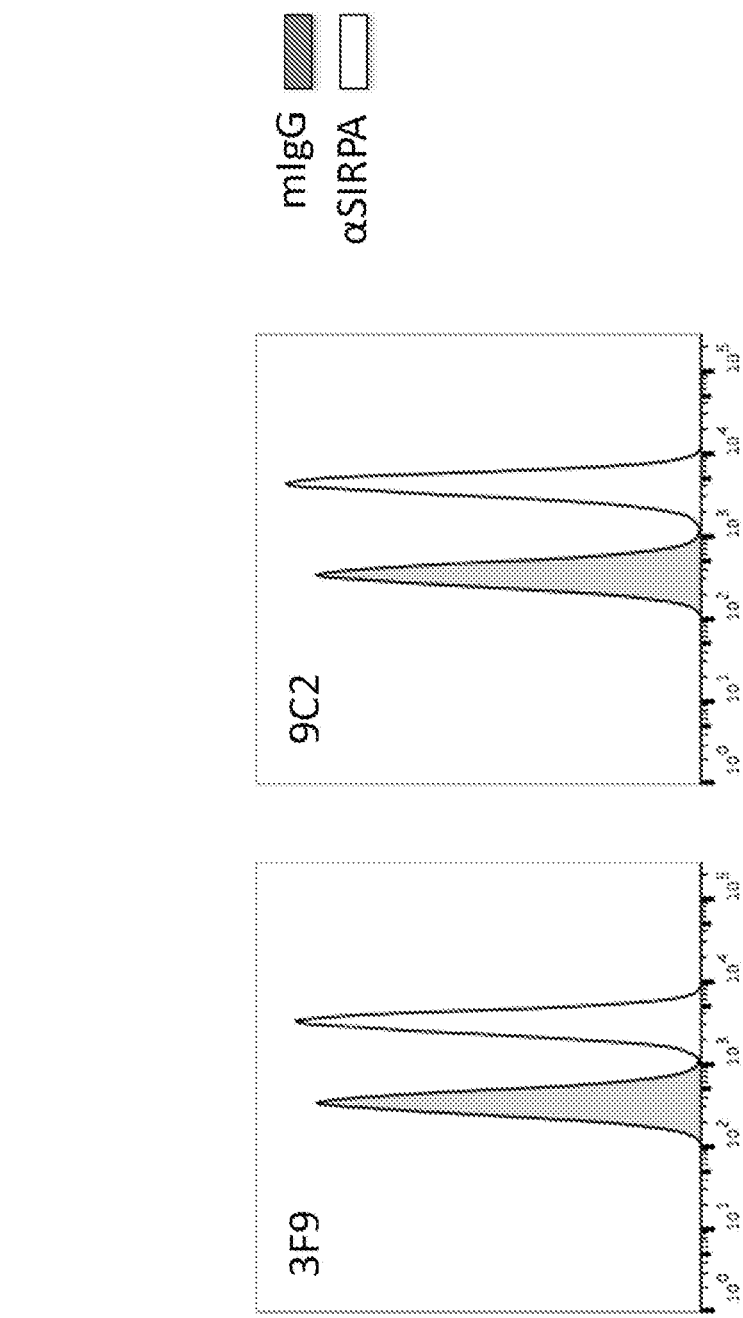
FIG. 3B shows FACS histograms of selected SIRPA antibodies binding to primary human macrophages. Antibody mIgG represents a negative isotype control. Shaded histograms represent the cells stained with anti-mouse IgG secondary antibody only. Black outlined histograms represent the SIRPA positive cell population.

Several antibodies, 3F9 and 9C2 for example, demonstrated binding to CHO-huSIRPA as indicated by positive SIRPA antibody staining detected via FACS analysis (black outlined histograms) (FIG. 3A). The negative isotype control (not shown) did not bind to cells. Likewise, 3F9 and 9C2 did not bind to CHO cells highly overexpressing mouse SIRPA (CHO-mSIRPA) (FIG. 3A, shaded histograms) confirming the specificity of the antibodies to the human antigen. Importantly, 3F9 and 9C2 also bound to primary human macrophages (FIG. 3B), the principal target cell population for in vivo efficacy. MFI values for cell lines bound by SIRPA antibodies are graphed in FIG. 3A and listed on Table 6, and typically show MFI values >100-fold over background levels.

TABLE 6

MFI values of anti-huSIRPA antibodies binding to cell surface receptor listed as fold over background

| AB ID | CHO-HuSIRPα | CHO-MuSIRPα |
|-------|-------------|-------------|
| mIgG | 1 | 1 |
| 1B3 | 129.9542 | 0.985036 |
| 3F9 | 136.6835 | 0.998266 |
| 9C2 | 127.6125 | 0.981093 |
| 9C5 | 89.64852 | 0.98305 |
| 12D6 | 128.3982 | 0.979942 |
| 1H11 | 149.9567 | 0.972255 |

Figure 3C:
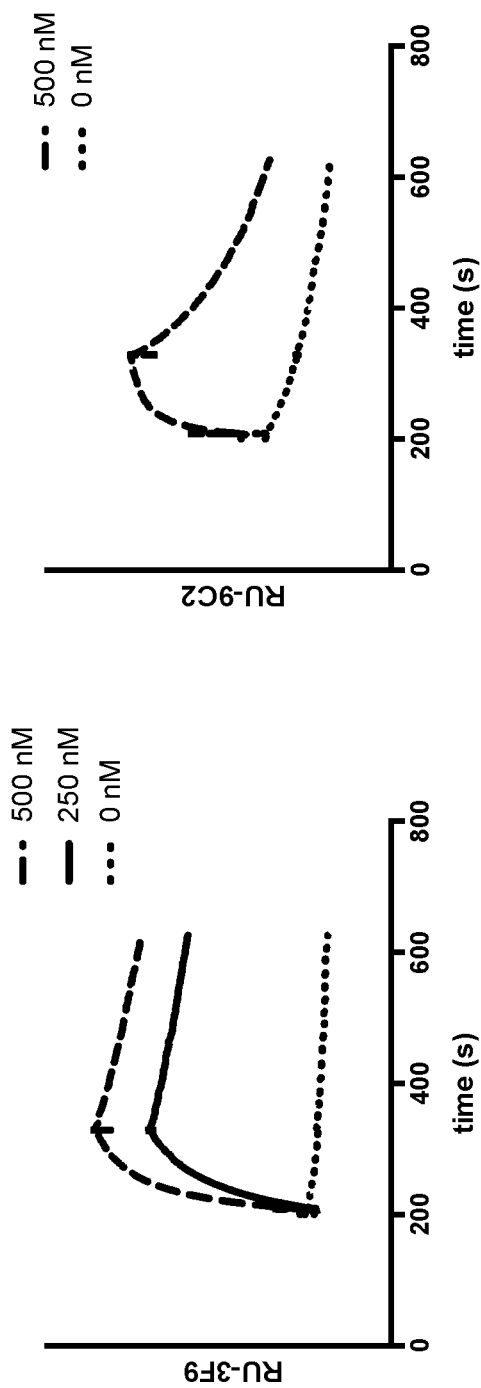
FIG. 3C shows surface plasmon resonance sensorgrams of indicated anti-SIRPA antibodies binding to recombinant soluble HuSIRPA protein. An anti-mouse IgG antibody immobilized on a CM5 chip captured anti-SIRPA antibodies and serial dilutions of His-tagged soluble HuSIRPA protein flowed over the antibody. Kd values were determined by curve fitting analysis.

Antigen affinity measurements for 3F9 and 9C2 were acquired with standard surface plasmon resonance (SPR) techniques (FIG. 3C). Binding studies were performed using a Biacore T200 (GE). An anti-mouse IgG capture antibody was amine coupled to a CM5 sensor chip using standard NHS/EDC activation. SIRPA antibodies were diluted to 50 nM in 1×HBS-EP+ running buffer and captured onto sensor chip surface. Serial dilutions of recombinant soluble human SIRPA antigen were injected over captured SIRPA antibodies to record sensorgram traces. Data were processed by subtracting RU values from the reference cell as well as the buffer injections. Binding curves were globally fit to a 1:1 interaction model to yield kinetic constants listed on Table 7. 3F9 and 9C2 bound to monomeric human SIRPA antigen with a $K_D$ of $1.0 \times 10^{-8}$ and $8.0 \times 10^{-8}$ M, respectively.

TABLE 7

Association rates, dissociation rates, and equilibrium binding constants of anti-huSIRPA antibodies

| AB ID | $k_{on}$ | $k_{off}$ | $K_D$ |
|-------|----------|-----------|-------|
| 3F9 | $5.5e4$ $(Ms)^{-1}$ | $5.7e-4$ $s^{-1}$ | 10 nM |
| 9C2 | $5.4e4$ $(Ms)^{-1}$ | $4.5e-3$ $s^{-1}$ | 80 nM |

Figure 3D:
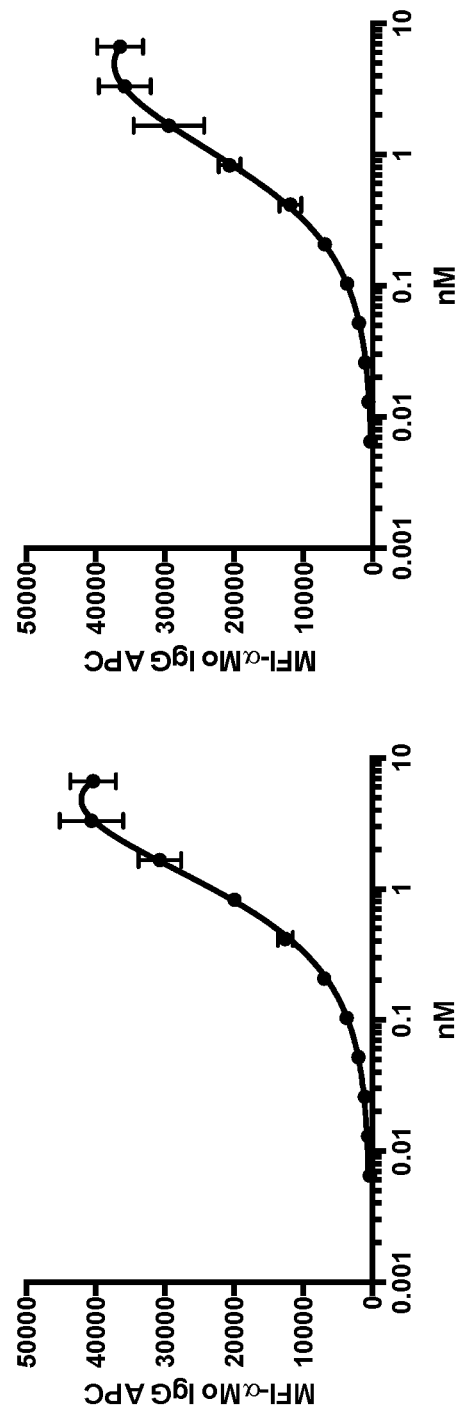
FIG. 3D shows binding of increasing concentrations of anti-SIRPA antibodies to human SIRPA overexpressed on CHO cells. EC50 values were calculated by fitting data to a sigmoidal curve with Graph Pad Prism.

Cell-based affinity measurements were also performed to ascertain the apparent affinities of 3F9 and 9C2 to cell surface antigen. Serial dilutions of monoclonal antibodies were added to $10^5$ CHO-huSIRPA cells and allowed to achieve binding equilibrium at 4° C. After addition of fluorescently labeled secondary antibody and brief washing steps, MFI values as a function of titrated antibody concentration was recorded via FACS analysis (FIG. 3D). Curves were fit using nonlinear regression analysis with Graphpad Prism 6 software. Cell-based titration experiments with 3F9 and 9C2 yielded EC50 values of 2.6 nM and 1.6 nM, respectively.

Example 3: Identifying CD47-Blocking and Non-Blocking SIRPA Antibodies

Given the role of the SIRPA-CD47 pathway in suppressing phagocytic cell effector functions, all antagonistic therapies described to date rely on competitive inhibition to block receptor-ligand interaction. Similarly, SIRPA antibodies in this application were screened for their ability to block CD47 binding to CHO-huSIRPA. Cells were harvested, plated at $10^5$ cells/well in a 96-well plate, washed, and incubated in 100 μl FACS buffer containing 1.0 μg/ml of indicated monoclonal antibody or isotype control. Cells were then washed and incubated in FACS buffer containing 250 nM His-tagged, soluble human CD47 for 30 minutes on ice. Cells were washed again and stained with PE-conjugated anti-His tag monoclonal antibody to detect surface bound CD47. Data analysis and calculation of MFI values or % positive cells was performed with FlowJo (TreeStar) software version 10.0.7.

Figure 4A:
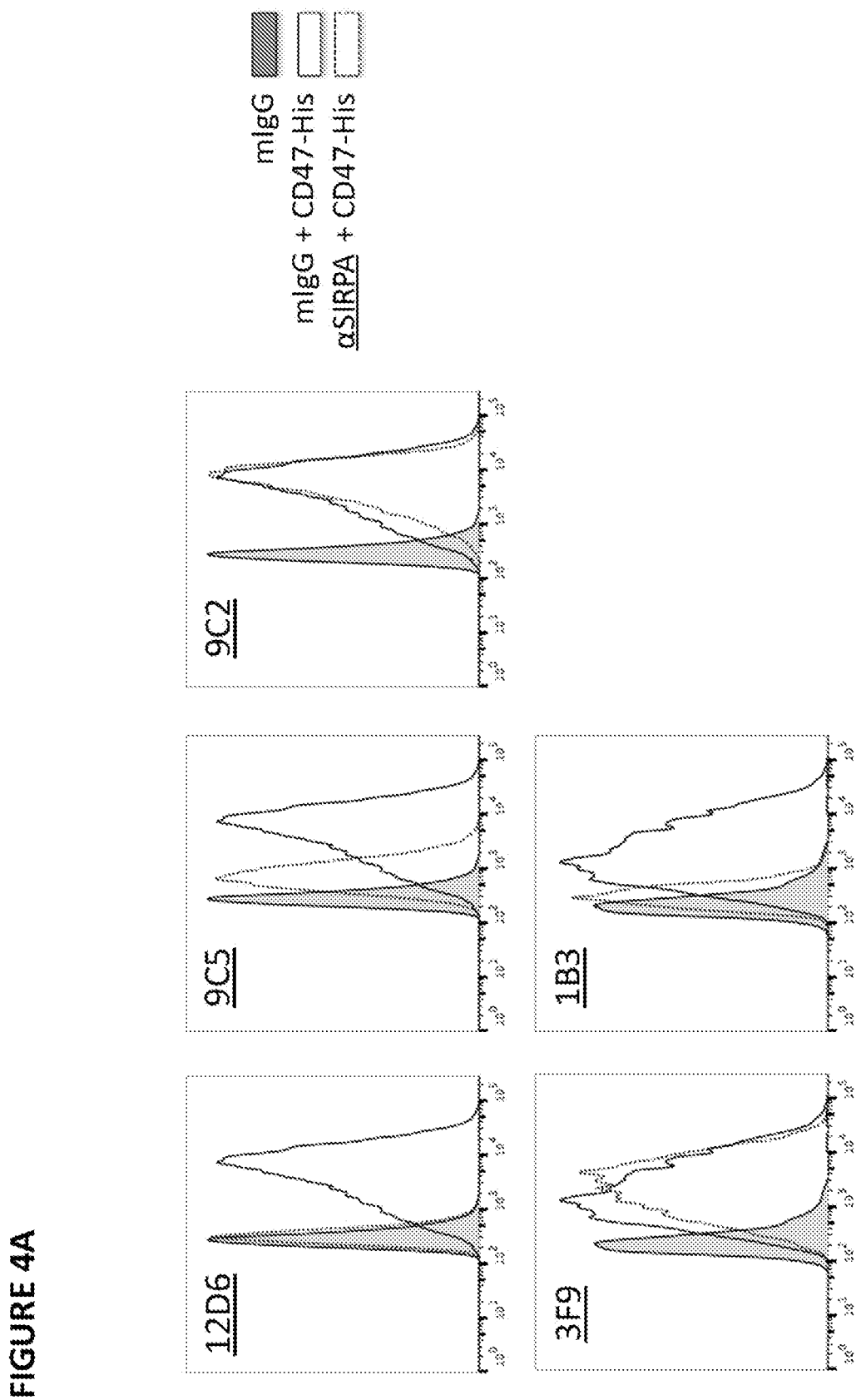
FIG. 4A shows FACS histograms of recombinant soluble human CD47 (HuCD47) binding to CHO-HuSIRPA cells in the presence of either anti-SIRPA antibodies (dashed line histogram) or mouse IgG1 isotype control (solid black outlined histogram). His-tagged HuCD47 was detected with PE-labeled anti-HIS tag secondary antibody. As a negative control (shaded histogram), CHO-HuSIRPA cells were stained with anti-HIS tag PE secondary antibody in the absence of HuCD47.
Figure 4B:
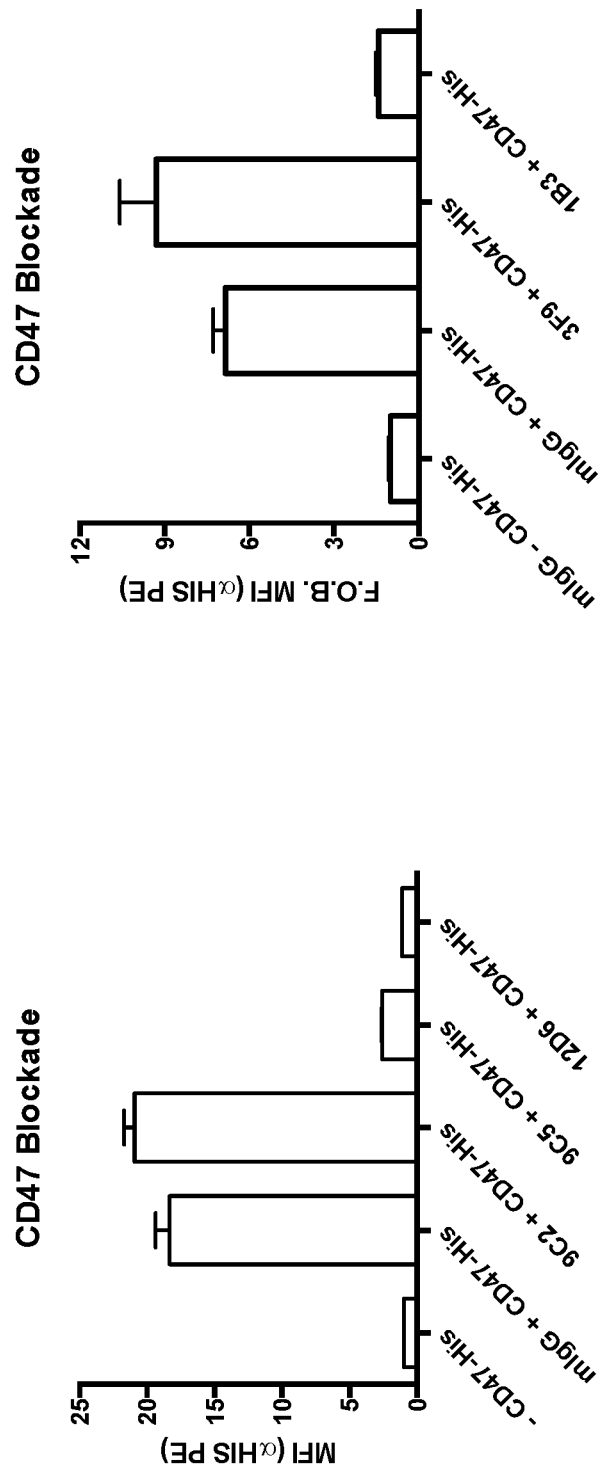
FIG. 4B shows the relative MFI values of HuCD47 binding to CHO-HuSIRPA cells in the presence of indicated anti-SIRPA antibodies or mouse IgG1 isotype control. Results are depicted as fold over background by dividing MFI values of samples treated with HuCD47 and antibodies by the MFI value of cells stained with anti-HIS tag PE in the absence of HuCD47.

As shown in FIG. 4A, soluble CD47 specifically bound CHO-huSIRPA cells as indicated by positive PE-staining via FACS analysis (black outlined histograms). In the absence of CD47-His, anti-His tag antibody failed to bind cells (shaded histograms). When CHO-huSIRPA cells were pre-incubated with indicated SIRPA antibodies, several clones, for example 12D6 and 1B3, exhibited near complete blockade of soluble CD47 binding (dashed line histograms). However, 3F9 and 9C2 represent two unique clones that do not inhibit soluble CD47 binding to CHO-huSIRPA cells. MFI values for cells bound by soluble CD47 are graphed as fold-over-background in FIG. 4B, and confirm that 3F9 and 9C2 do not interfere with CD47 interaction.

Example 4: SIRPA Antibodies Modulate SIRPA-Dependent Gene Expression

In addition to ligand blockade, SIRPA antibodies were also screened for ability to inhibit CD47-induced gene expression using a luciferase reporter gene under the control of an NFAT (nuclear factor of activated T-cells) promoter. The cell line BW5147.G.1.4 (ATCC® TIB48™), derived from mouse thymus lymphoma T lymphocytes, was infected with Cignal Lenti NFAT-luciferase virus (Qiagen) and a lentivirus expressing human SIRPA-DAP12 chimera, in which the intracellular ITIM motif of SIRPA was substituted with the intracellular ITAM motif of DAP12. Soluble human CD47 protein was serially diluted in PBS and adsorbed onto tissue culture plates. After washing, $10^5$ NFAT-luciferase reporter cells expressing the huSIRPA/DAP12 chimera (BWZ-huSIRPA) were seeded onto plates and incubated overnight at 37 C. Luciferase activity was measured by adding OneGlo Reagent (Promega) to each well and incubating samples for 3 min at room temperature on a plate shaker. The luminescence signal was quantified using a BioTek Synergy™ Microplate Reader using GEN5™ 2.04 software.

Figure 5A:
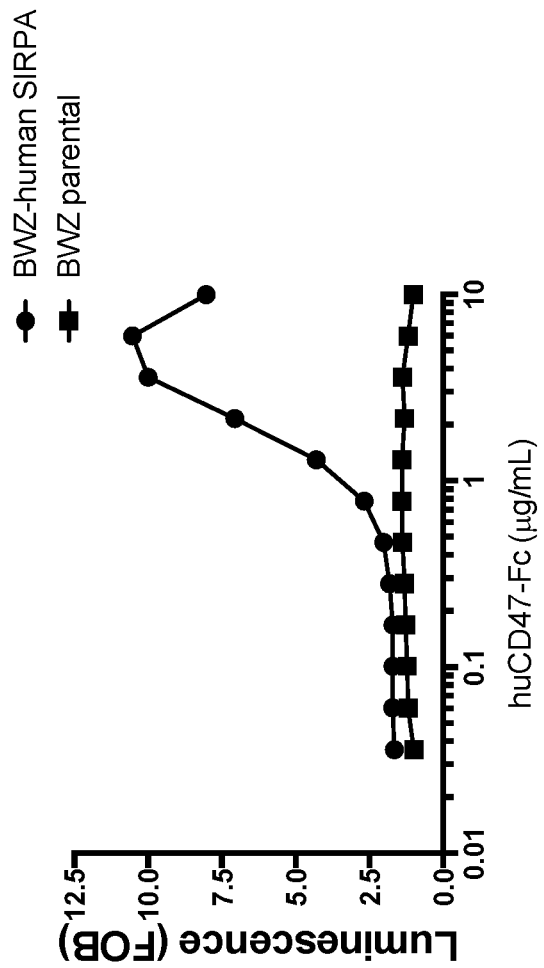
FIG. 5A shows induction of human SIRPA-dependent luciferase expression in a cell-based reporter assay. BWZ/NFAT-luciferase reporter cells (BWZ) were engineered to stably express human SIRPA-DAP12 chimera (BWZ-HuSIRPA). Cells were stimulated with increasing concentrations of plate-bound, recombinant HuCD47. Only cells expressing HuSIRPA chimera induced luciferase expression in a dose-dependent manner, as measured by luminescence signal. Results are expressed as fold over background. The background level is set to 1 on y-axis.
Figure 5B:
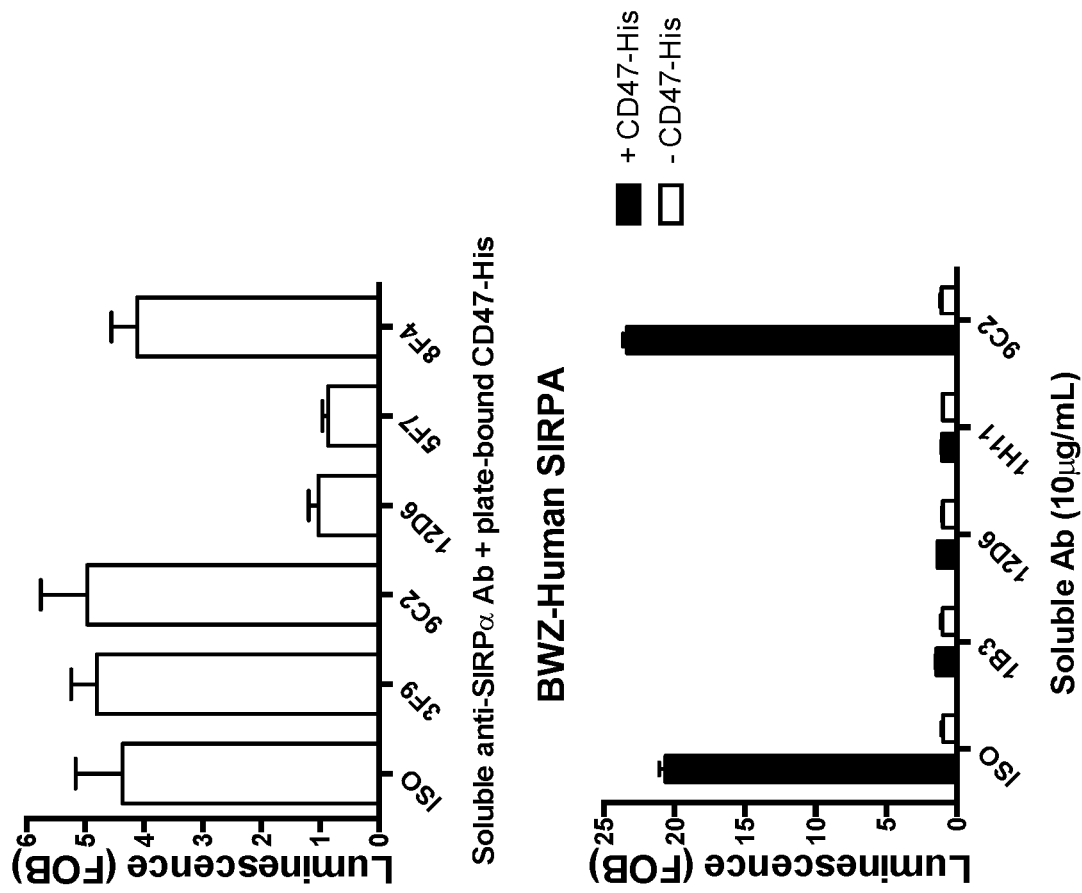
FIG. 5B shows the ability of CD47-blocking and CD47-non-blocking anti-SIRPA antibodies to affect HuSIRPA-dependent luciferase expression in a cell-based reporter assay. BWZ-HuSIRPA cells were seeded on wells with or without plate-bound CD47 protein. All CD47-blocking antibodies (1B3, 12D6, 1H11, 5F7) potently suppress luminescence signal. Two CD47-non-blocking anti-SIRPA antibodies did not reduce luciferase expression. Results are expressed as fold over background. The background level is set to 1 on y-axis.

As shown in FIG. 5A, plate-bound human CD47 induced luciferase activity in reporter cells expressing chimeric human SIRPA/DAP12 in a dose-dependent fashion. Importantly, the parental BWZ reporter cells, which lack SIRPA/DAP12 expression, did not emit a luminescence signal in response to CD47 verifying that the chimeric receptor mimics the signaling events initiated through ligand binding. Next, anti-SIRPA antibodies were assessed for their ability to block CD47-dependent luciferase activity in BWZ-huSIRPA reporter cells. As described above, soluble human CD47 protein was diluted in PBS and adsorbed onto 96-well tissue culture plates. After washing, $10^5$ BWZ-huSIRPA reporter cells were seeded onto plates with either isotype control antibody or the indicated anti-SIRPA antibody and incubated overnight at 37 C. FIG. 5B demonstrates that, in accordance with the CD47 binding assays described previously, anti-SIRPA antibodies that block CD47 binding to CHO-huSIRPA cells, such as 12D6 and 5F7, also inhibit CD47-dependent luciferase activity in reporter cells. Likewise, anti-SIRPA antibodies that do not block CD47 binding to CHO-huSIRPA cells, such as 9C2 and 3F9, also do not inhibit CD47-dependent luciferase activity in BWZ-huSIRPA cells. Furthermore, anti-SIRPA antibodies do not induce signaling in solution since reporter cells incubated with soluble SIRPA antibodies do not emit luminescence signal in the absence of plate-bound CD47.

Example 5: Identification of SIRPA-Specific Antibodies

The initial characterization of SIRPA antibodies identified a class of CD47-blocking and non-blocking antibodies capable of binding primary human myeloid cells. However, given the high sequence homology between SIRPα and SIRPβ1 (~90% identity), SIRPA-specific binding remains a critical feature of an ideal anti-SIRPA lead antibody. In order to screen SIRPA antibodies for SIRPβ1 cross-reactivity, BWZ-NFAT/luciferase reporter cells were transduced with a lentivirus expressing human SIRPβ1. Unlike SIRPα, SIRPβ1 requires co-expression of DAP12 adaptor for full cell surface localization. As a result, BWZ-huSIRPβ1 cells were also transduced with a lentivirus separately expressing human DAP12. To test luciferase activation, selected SIRPA antibodies or isotype control were diluted in PBS at 10 μg/mL and adsorbed onto tissue culture plates. After washing, $10^5$ NFAT-luciferase reporter cells expressing either huSIRPA/DAP12 chimera (BWZ-huSIRPA) or huSIRPβ1+DAP12 (BWZ-huSIRPβ1) were seeded onto plates and incubated overnight at 37 C. Luciferase activity was measured by adding OneGlo Reagent (Promega) to each well and incubating samples for 3 min at room temperature on a plate shaker. The luminescence signal was quantified using a BioTek Synergy™ Microplate Reader using GEN5™ 2.04 software.

Figure 6A:
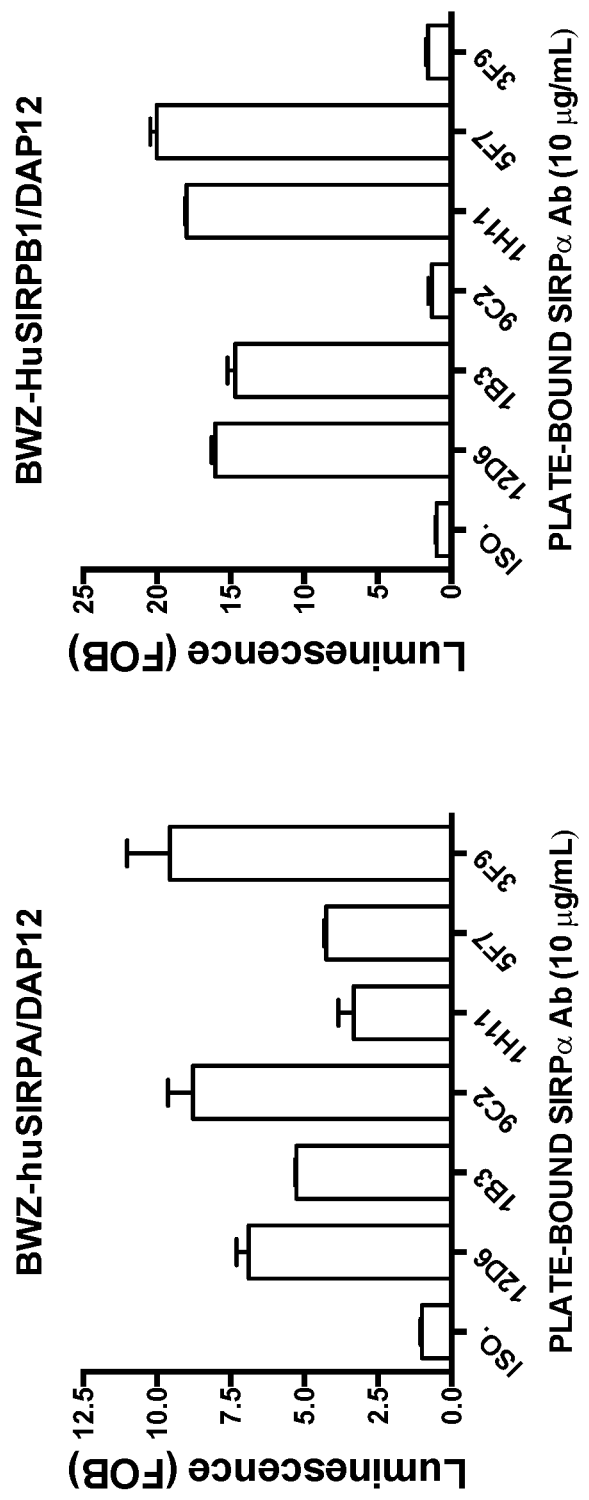
FIG. 6A shows induction of human SIRPA-dependent or human SIRPB1-dependent luciferase expression in a cell-based reporter assay. BWZ-HuSIRPA and BWZ-HuSIRPB1 reporter cells were stimulated with plate-bound, full-length anti-SIRPA antibodies or mIgG1 isotype control. CD47-blocking anti-SIRPA antibodies activated both SIRPA-expressing and SIRPB1-expressing reporter cells, whereas the CD47-non-blocking anti-SIRPA antibodies (3F9 and 9C2) specifically activated only BWZ-HuSIRPA cells.

As shown in FIG. 6A, plate-bound SIRPA antibodies induced luciferase activity in reporter cells expressing chimeric human SIRPA/DAP12 to a similar extent as previously observed with plate-bound CD47. However, most SIRPA antibodies also induced luciferase activity in BWZ-huSIRPβ1 reporter cells indicating that these antibodies cross-react with both SIRPα and SIRPβL Interestingly, two antibody clones, 3F9 and 9C2, specifically activated BWZ-huSIRPA cells but not BWZ-huSIRPβ1 suggesting that these 2 clones represent unique SIRPA-specific antibodies.

Figure 6B:
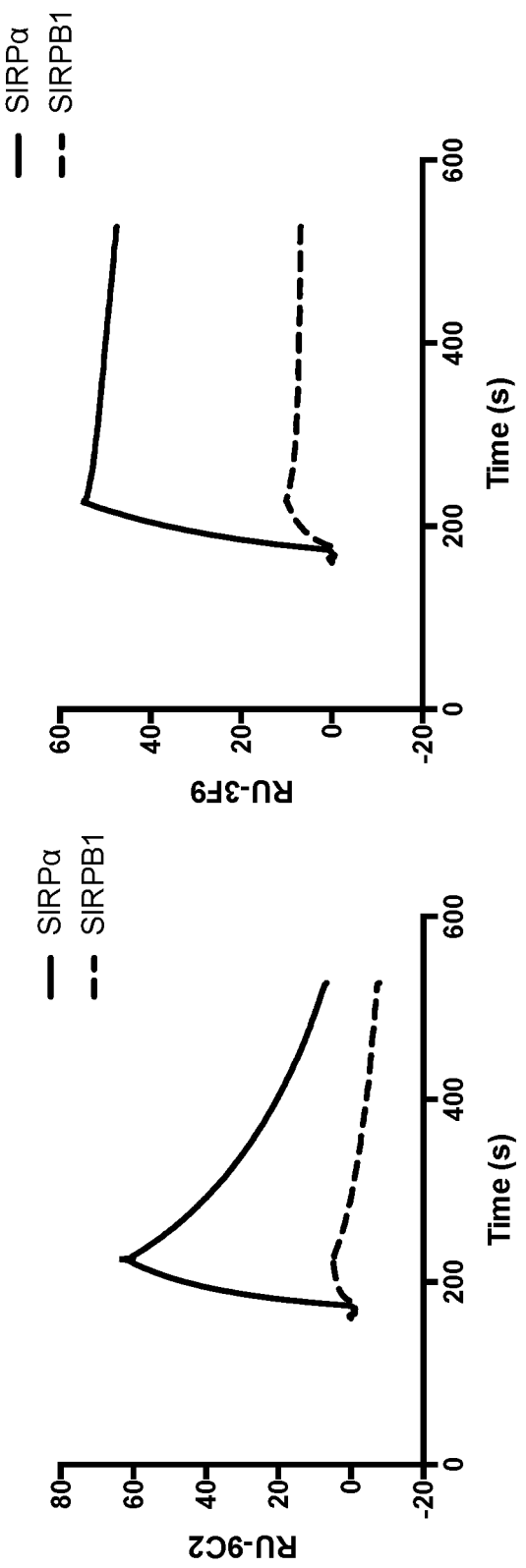
FIG. 6B shows surface plasmon resonance sensorgrams of indicated anti-SIRPA antibodies binding to recombinant soluble HuSIRPA antigen or HuSIRPB1 antigen. An anti-mouse IgG antibody immobilized on a CM5 chip captured anti-SIRPA antibodies and equimolar concentration of antigen flowed over the captured antibody.

To confirm this observation, we performed SPR-based binding studies with Biacore T200 (GE). An anti-mouse IgG capture antibody was amine coupled to a CM5 sensor chip using standard NHS/EDC activation. SIRPA antibodies, either 3F9 or 9C2, were diluted to 50 nM in 1×HBS-EP+ running buffer and captured onto sensor chip surface. Equimolar concentrations of recombinant soluble human SIRPA antigen or human SIRPB1 antigen were injected over captured SIRPA antibodies to record sensorgram traces. Data were processed by subtracting RU values from the reference cell as well as the buffer injections. The sensorgrams in FIG. 6B clearly show an increase in response units following injection of SIRPA antigen over captured antibodies 3F9 and 9C2. In contrast, flowing SIRPB1 antigen over captured antibodies barely records a binding response above background. Thus, the results from FIGS. 6A and 6B identify clones 3F9 and 9C2 as SIRPA-specific antibodies.

Example 6: SIRPA-Specific Antibodies Decrease Cell Surface Expression of SIRPα in Human Macrophages It is frequently observed that antibodies targeting certain ITIM/ITAM receptors expressed on the surface of immune cells can reduce the surface levels of said receptor on monocytes, macrophages, dendritic cells, neutrophils, and/or microglia.

The ability of anti-SIRPA antibodies to reduce cell surface expression of SIRPα was evaluated on primary human macrophages (huMacs). Human monocytes were isolated from peripheral blood of healthy donors and differentiated into macrophages in vitro. Following differentiation, $10^5$ huMacs were harvested and seeded onto 96-well tissue culture plates with either 1-5 μg/ml of isotype control or soluble anti-SIRPA antibodies. Cells were analyzed by flow cytometry for SIRPα surface expression following 4 hr treatment or overnight incubation. SIRPα expression was detected using a DyLight650-conjugated anti-human SIRPA antibody belonging to a separate epitope bin than 9C2 and 3F9.

Figure 7A:
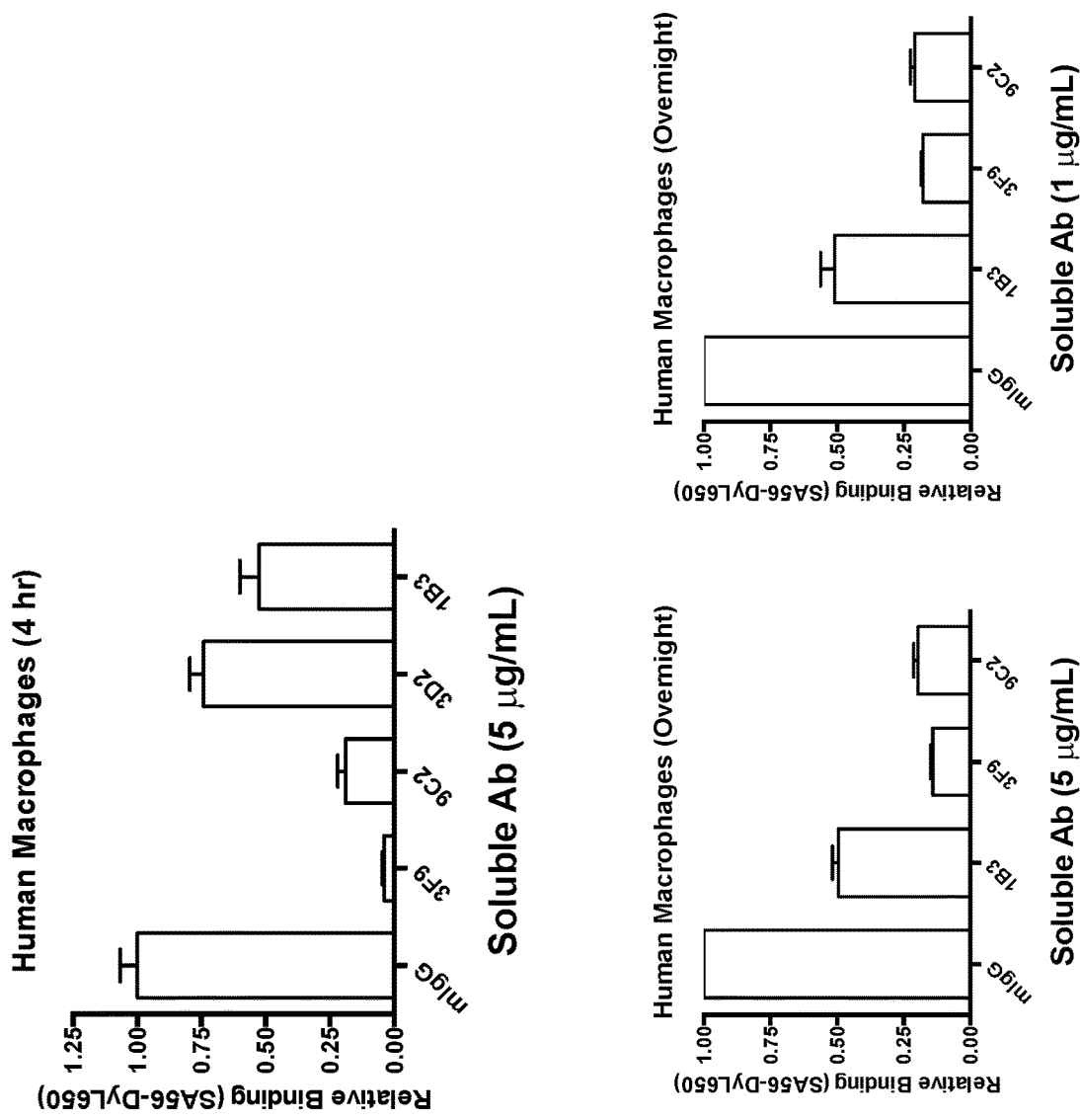
FIG. 7A shows SIRPA receptor down-regulation in primary human macrophages in response to antibody stimulation. Cells were treated with either soluble full-length isotype control or soluble full-length anti-SIRPA antibodies and subsequently stained with a DyLight650-conjugated anti-SIRPA reference antibody (SA56-DyL650) that binds to a distinct epitope bin.
Figure 7B:
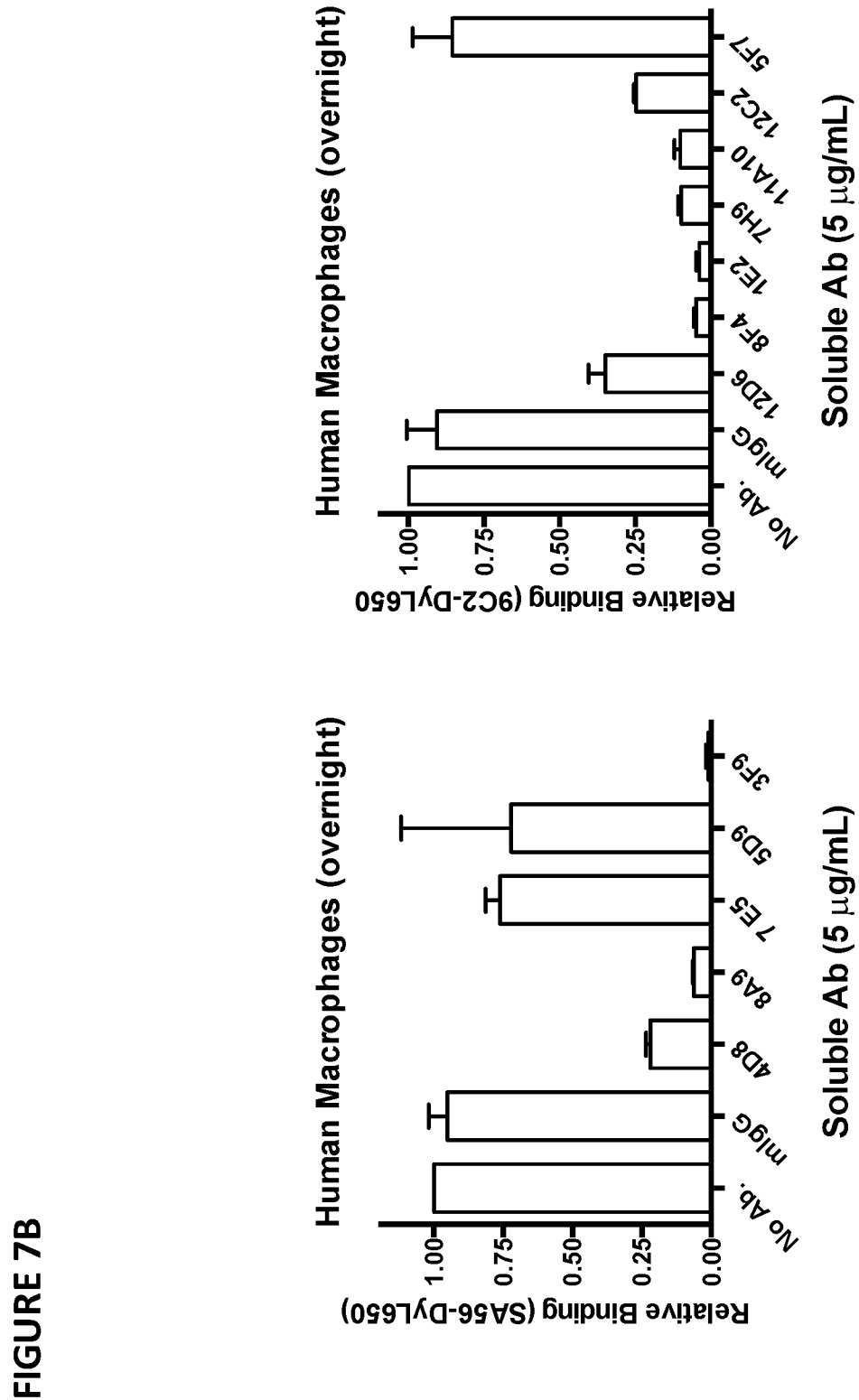
FIG. 7B shows SIRPA receptor down-regulation in primary human macrophages treated with CD47-non-blocking antibodies. For comparison, macrophages were also treated with 2 CD47-blocking antibodies (12D6 and 5F7). Results are presented as percent of reference antibody binding by dividing MFI value of samples treated with anti-SIRPA antibodies by the MFI value of samples treated with the isotype control.

As shown in FIG. 7A, the SIRPA-specific antibodies, 3F9 and 9C2, significantly reduce SIRPα expression by ~90% relative to isotype control-treated macrophages. FACS analysis reveals that receptor down-regulation occurs within hours after antibody addition and is sustained through overnight treatment. This is in contrast to the CD47-blocking antibodies, for example 1B3 or 3D2, which only reduced receptor expression by 50% or less. Since antibody clones 3F9 and 9C2 are also CD47-non-blocking antibodies, other CD47-non-blocking antibodies were screened for receptor down-regulation. FIG. 7B shows that, in most cases, CD47-non-blocking antibodies as a class significantly reduced SIRPα expression by ~90% or more. Again, consistent with previous observations, CD47-blocking antibodies, in this example 5F7 and 12D6, were less effective at receptor downregulation by comparison. Thus, FIGS. 7A and 7B establishes the downregulation of SIRPα as a defining characteristic of the non-ligand blocking SIRPA antibodies. By reducing receptor expression, these antibodies may antagonize the SIRPα-CD47 signaling pathway through non-competitive inhibition, a novel mechanism not previously explored in the field.

Example 7: SIRPα Down-Regulation Enhances Phagocytosis of Tumor Cells by Human Macrophages Tumor cells evade immune surveillance through the upregulation of CD47 thereby transmitting an inhibitory signal to phagocytic cells. Antagonistic antibodies therefore counteract this inhibition to enhance tumor cell phagocytosis. In order to determine if SIRPA antibodies effectively inhibit SIRPα signaling by receptor downregulation, a tumor cell phagocytosis assay was developed based on the acquisition of pHrodo fluorescence. Red Avidin (Invitrogen) is a streptavidin molecule conjugated with pHrodo Red dye, a fluorogenic marker that acquires fluorescence in acidic environments, such as the phagosome. For target tumor cell labeling, 500 nM Red Avidin was mixed with 15 nM biotinylated Lens Culinaris Agglutinin (LCA; Vector Labs). Red Avidin-LCA complexes were then mixed in a 1:1 volumetric ratio with 250,000 Raji cells in serum-free RPMI media on ice. The sugar-binding properties of LCA links Red Avidin to carbohydrate structures on the tumor cell surface. After brief washing steps, Red Avidin-LCA-labeled Raji cells were mixed with monocyte-derived human macrophages in serum-free RPMI media and incubated at 37C for 2 hours. Macrophages were then collected and stained on ice with anti-CD14 APC in FACS buffer containing FcγR-blocking antibodies. Phagocytic activity was measured by counting percent of APC/pHrodo-double positive macrophages. As a control, unlabeled Raji cells were mixed with macrophages to establish background fluorescence.

Figure 8A:
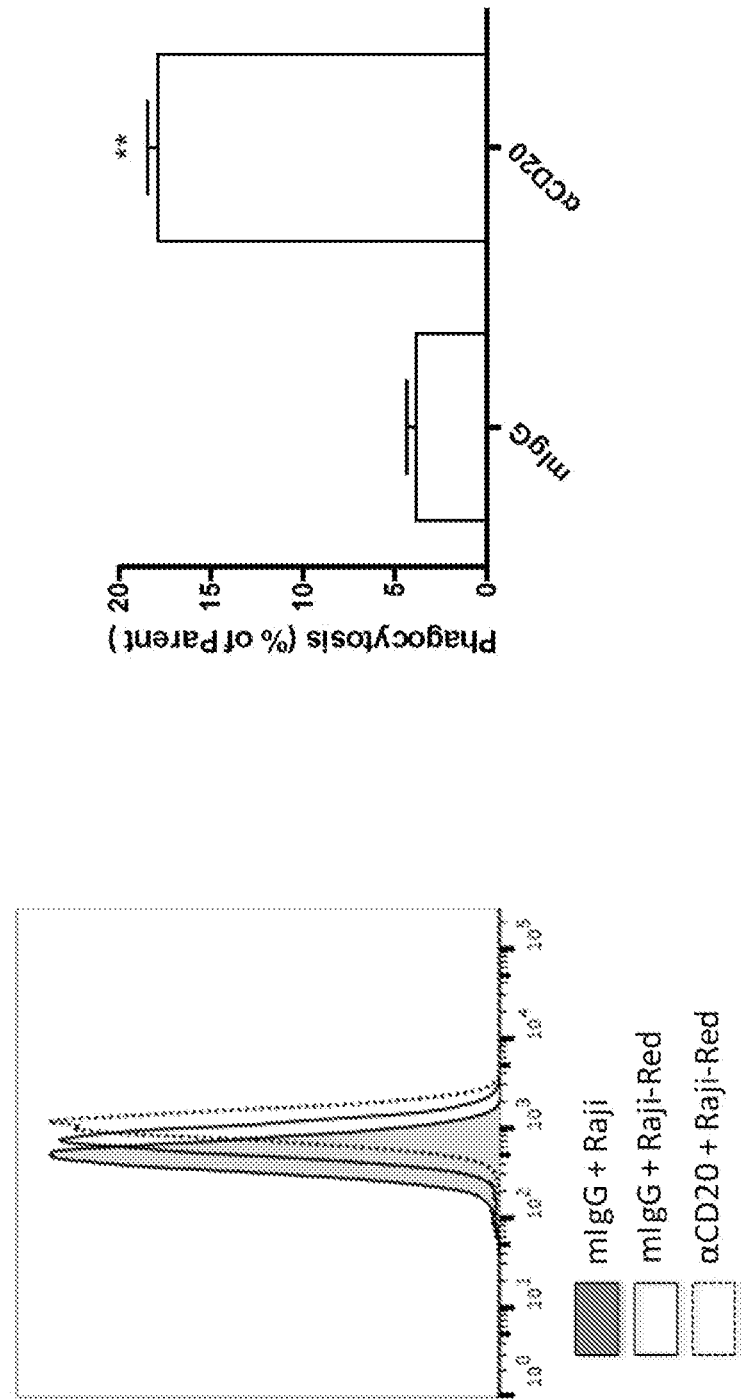
FIG. 8A establishes a live cell phagocytosis assay with macrophages as effector cells and pHrodo-labeled tumor cells as targets. Biotinylated Lens culinaris agglutinin (LCA), a mannose binding lectin, was complexed with avidin-conjugated pHrodo red dye. LCA-pHrodo complexes were then mixed with Raji cells (human B-cell lymphoma line) in order to coat cell surface with pHrodo through LCA binding carbohydrate structures on the cell membrane. Labeled Raji cells (Raji-Red) either alone or opsonized with anti-CD20 antibody were mixed with macrophages at a 2:1 ratio and incubated for 2 hours to allow phagocytosis of cells. Phagocytic activity was measured by counting percent of CD14-APC+/PE+ macrophages by FACS analysis.

FIG. 8A(i-ii) establishes the validity of this assay. Monocyte-derived macrophages were seeded onto 96-well tissue culture plates at $10^5$ cells/well and treated overnight with isotype control antibody. The following day, 250,000 Red Avidin-labeled Raji cells or unlabeled Raji cells were mixed with macrophages for 2 hours and subsequently analyzed by flow cytometry. The histograms in FIG. 8A(i) demonstrate the shift in pHrodo-fluorescence observed when macrophages are co-cultured with Red Avidin-labeled Raji cells (solid black outlined histogram) compared to unlabeled cells (shaded histogram). However, this shifted population only represents ~5% of total $CD14^+$ macrophages (FIG. 8Aii). Opsonization of Red Avidin-labeled Raji cells with an anti-CD20 antibody (Rituximab) shifts $pHrodo^+$ macrophage population even further (dashed outline histogram) consistent with antibody-dependent phagocytosis enhancing tumor cell clearance. As a result of adding Rituximab, $pHrodo^+$ macrophages represent ~20% of total $CD14^+$ macrophages, a nearly 4-fold increase in phagocytic activity.

Figure 8B:
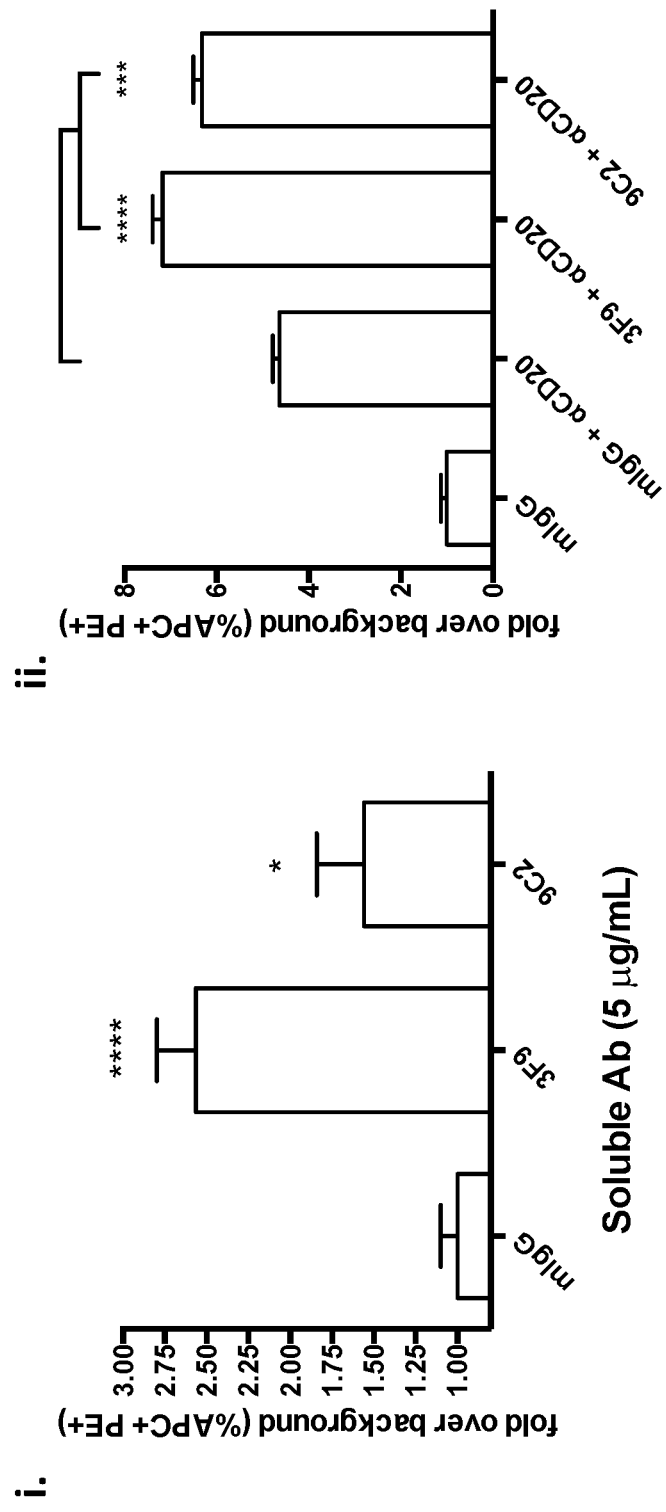
FIG. 8B shows enhanced phagocytic activity of macrophages treated with CD47-non-blocking anti-SIRPA antibodies. Macrophages were cultured overnight in 2.5% FBS RPMI media with 5 µg/mL of 3F9, 9C2, 1B3 (CD47-blocker), or isotype control. Raji-Red cells either alone or opsonized with anti-CD20 antibody were mixed with macrophages at a 2:1 ratio and phagocytic activity was determined as previously described.
Figure 8C:
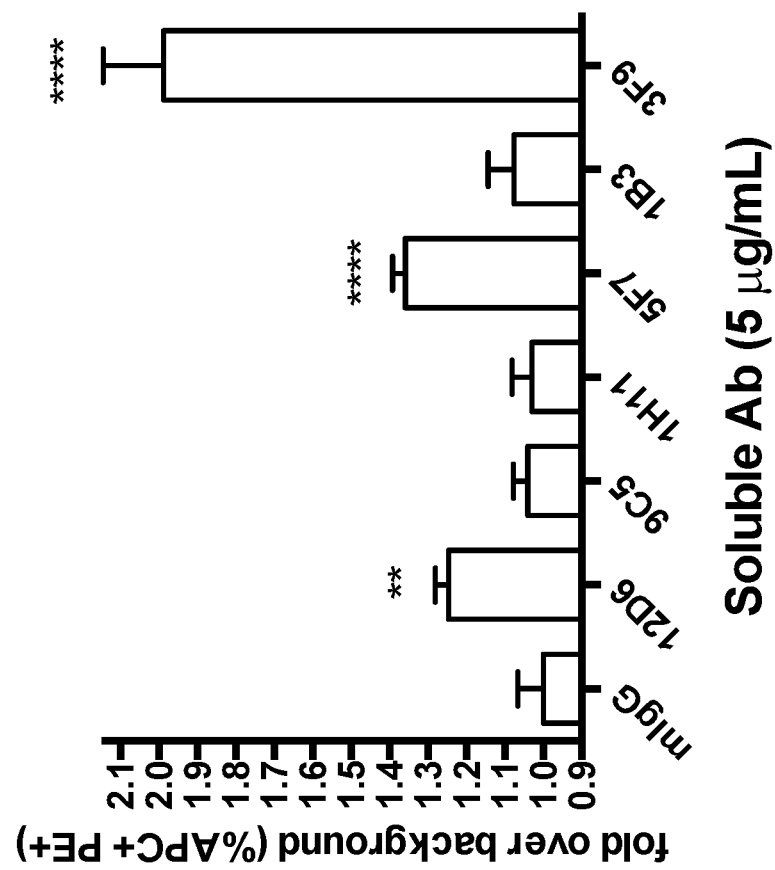
FIG. 8C shows enhanced phagocytic activity of macrophages treated with CD47-blocking anti-SIRPA antibodies. Macrophages were cultured overnight in 2.5% FBS RPMI media with 5 µg/mL of 12D6, 9C5, 1H11, 5F7, 1B3, 3F9 (CD47-non-blocker) or isotype control. Phagocytic activity was measured as described above.

To test SIRPA antibodies, macrophages were treated overnight with the indicated candidate antibody or isotype control. The next day, labeled Raji cells were added to treated macrophages followed by quantification of phagocytic activity. As shown in FIG. 8B, both 3F9 and 9C2 increased the population of $CD14^+/pHrodo^+$-macrophages 2.5-fold and 1.5-fold, respectively, over isotype treated macrophages. Combination therapy, in which rituximab-opsonized Raji cells were added to 3F9- or 9C2-treated macrophages, further enhanced tumor cell engulfment relative to isotype-treated macrophages. Whereas rituximab alone increased phagocytic activity ~4-fold over untreated cells, rituximab+3F9 or rituximab+9C2 treatment augmented phagocytosis 7-fold and 6-fold, respectively. Since 3F9 and 9C2 are SIRPA-specific antibodies that do not competitively inhibit CD47 binding, FIG. 8C compares the phagocytic activity of macrophages treated with CD47-blocking versus CD47-non-blocking antibodies. Among the CD47-blocking antibodies, only 12D6 and 5F7 significantly increased tumor cell uptake by ~30-40% above isotype treated macrophages. By comparison, phagocytic activity of 3F9-treated macrophages increased 2-fold. Thus the results from FIG. 8A-C establish that antibody-mediated down-regulation of SIRPα on macrophages enhances phagocytic uptake of tumor cells. Combining SIRPA antibodies with anti-tumor antigen antibodies further potentiates tumor cell clearance by effector cells. Finally, in comparison to anti-SIRPA antibodies that competitively inhibit CD47 interaction, antibodies that non-competitively inhibit CD47 binding by reducing SIRPα expression demonstrate a superior capacity to stimulate engulfment of tumor cells by macrophages.

Example 8: SIRPα Down-Regulation Activates Primary Human Monocytes

Though macrophages may be the principal effector cell population driving tumor cell clearance in response to anti-SIRPA therapy, SIRPA antibodies will engage multiple myeloid cell lineages expressing SIRPα. Among these cells are monocytes, which populate the peripheral blood, and thus, are easily accessible to assay target engagement upon antibody administration in vivo. In order to identify potential biomarkers, primary monocytes were isolated from peripheral blood of healthy donors and assayed for activation markers following antibody treatment.

Figure 9A:
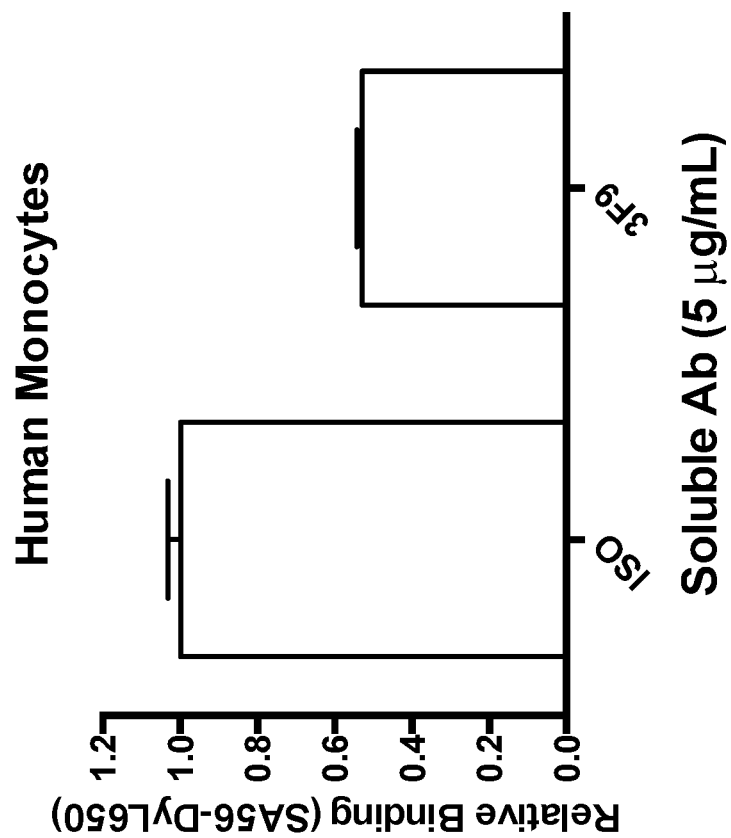
FIG. 9A shows SIRPA receptor down-regulation in primary human monocytes in response to antibody stimulation. Cells were treated with either soluble full-length isotype control or anti-SIRPA antibody, 3F9, and subsequently stained with a DyLight650-conjugated anti-SIRPA reference antibody (SA56-DyL650) that binds to a distinct epitope bin.
Figure 9B:
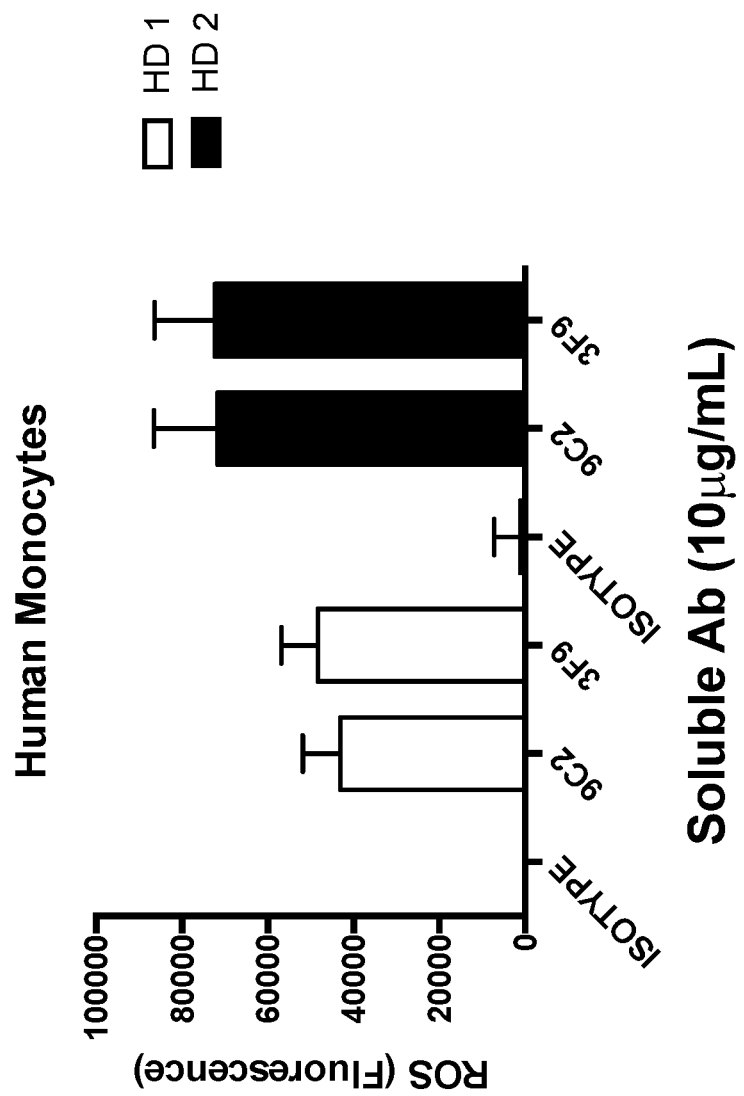
FIG. 9B shows respiratory burst from primary human monocytes isolated from 2 healthy donors (HD). Cells were stimulated with soluble full-length mouse IgG1 isotype control or the anti-SIRPA antibodies 3F9 and 9C2. In all experiments, production of reactive oxygen species (ROS) was monitored by labeling cells with 2 µM of the fluorescent indicator, CM-H2DCFDA.
Figure 9C:
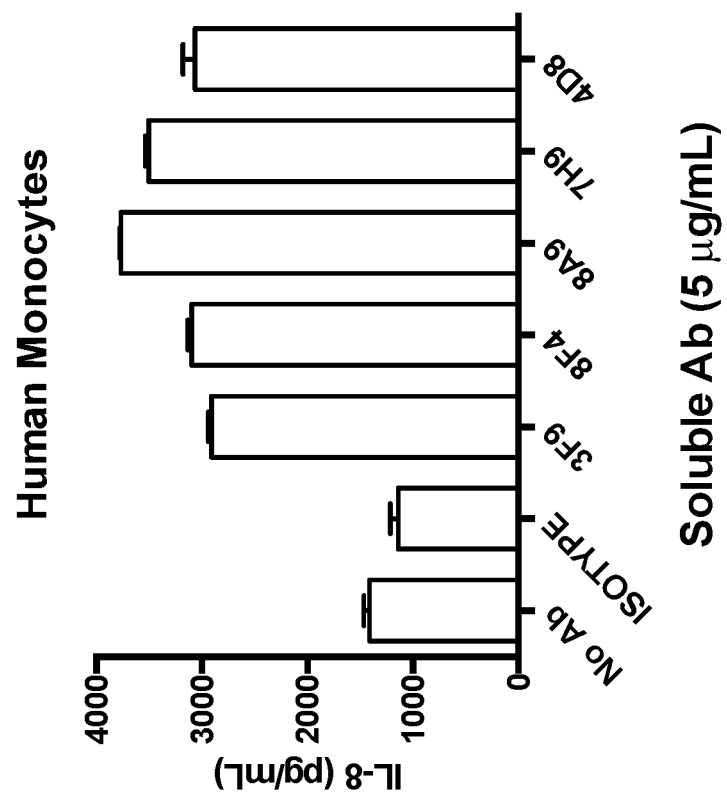
FIG. 9C shows IL-8 secretion from primary human monocytes stimulated overnight with CD47-non-blocking antibodies. Supernatants were collected and cytokine concentration determined by standard ELISA protocols as instructed by manufacturer (eBioscience).

The ability of anti-SIRPA antibodies to reduce surface expression of SIRPα was verified on monocytes. Following isolation, $10^5$ monocytes were seeded onto 96-well tissue culture plates with either 5 μg/ml of isotype control or soluble anti-SIRPA antibodies. Cells were analyzed by flow cytometry for SIRPα surface expression after overnight incubation. SIRPα expression was detected using a DyLight650-conjugated anti-human SIRPA antibody belonging to a distinct epitope bin. FIG. 9A shows that 3F9 reduces surface expression of SIRPα by 50% relative to isotype control treated cells. Though receptor downregulation appears less robust in monocytes than previously observed in macrophages, monocytes were assayed for production of inflammatory mediators, for example production of reactive oxygen species (ROS) and pro-inflammatory cytokines. To detect ROS production, $10^5$ monocytes were seeded onto 96-well tissue culture plates with either 10 μg/ml of isotype control or soluble anti-SIRPA antibodies. Subsequently, cells were labeled with 2 μM of the fluorescent dye, CM-H2DCFDA. Following 1 hour of antibody-mediated stimulation at 37° C., the relative fluorescence units in cells were measured at excitation wavelength 495 nm and emission wavelength 530 nm. Specific fluorescence index of stimulated cells was obtained by subtraction of background fluorescence of labeled cells incubated in medium alone and/or with isotype control antibody. Plates were read with a BioTek Synergy™ Microplate Reader using GEN5™ 2.04 software. FIG. 9B shows that SIRPA-specific antibodies, 3F9 and 9C2, stimulated ROS production in monocytes isolated from 2 healthy donors. Additionally, FIG. 9C shows that $10^5$ monocytes treated overnight with SIRPα-downregulating antibodies produces elevated amounts of IL-8. Thus, the results from FIG. 9A-C suggest that, in addition to reducing receptor surface expression, anti-SIRPA antibodies may also polarize cells towards a more active phenotype.

Figure 10A:
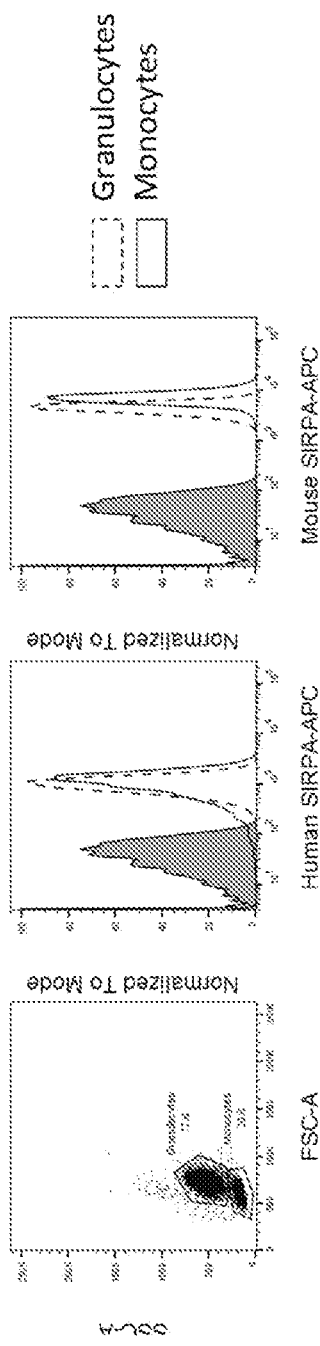
FIG. 10A shows the expression of mouse and human SIRPA in peripheral blood monocytes (solid line) and granulocytes (dashed line) by FACS staining in huSIRPA-tg mice. Human SIRPA was detected with anti-hSIRPα/β-APC (clone SE5A5, Biolegend); mouse SIRPA was detected with anti-mSIRPα-APC (clone p84, Biolegend). Isotype staining is shown as a shaded histogram.
Figure 10B:
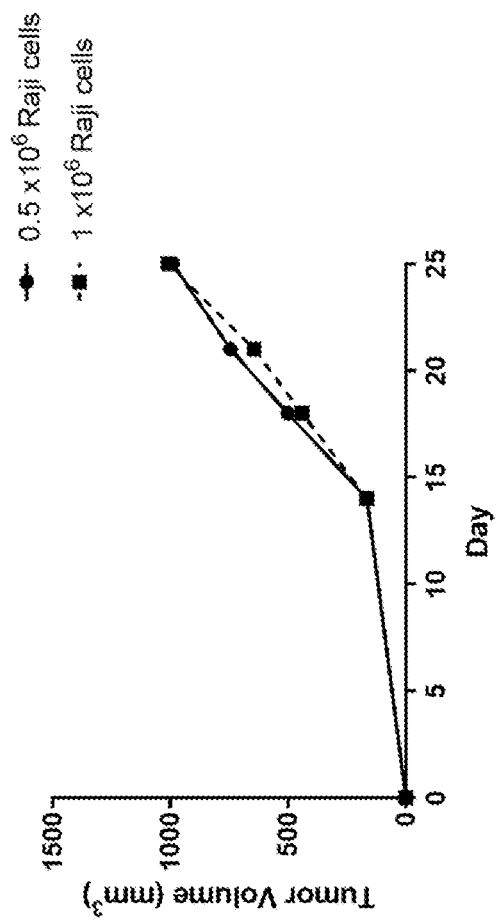
FIG. 10B shows tumor volume measurements of huSIRPA-tg mice implanted subcutaneously with Raji B cell lymphoma cells. Three mice per group received either $5 \times 10^5$ or $1 \times 10^6$ Raji cells. Solid tumor formation was determined by caliper measurements twice per week.

Example 9: SIRPA-Specific Antibodies Decrease Cell Surface Expression of SIRPα In Vivo In order to determine if anti-SIRPA antibodies reduce cell surface expression of the receptor in in vivo model systems, human BAC transgenic mice encoding the human SIRPA gene in a RAG2-deficient and IL2R γ chain-deficient background were obtained. The expression level of huSIRPA was analyzed on mouse myeloid cells by flow cytometry. As shown in FIG. 10A, monocytes and granulocytes isolated from mouse peripheral blood expressed human SIRPA, as well as endogenous mouse SIRPA. Macrophages and dendritic cells derived from bone marrow cells also express huSIRPA. Thus, the huSIRPA-tg mice faithfully recapitulate the expression pattern of human SIRPA in mouse cells. Furthermore, to determine if huSIRPA retained its inhibitory function, huSIRPA-tg mice were implanted with Raji cells, a human B cell lymphoma cell line that overexpresses human CD47. As shown in FIG. 10B, subcutaneous administration of Raji cells results in solid tumor formation suggesting that huSIRPA-tg mice support engraftment of CD47+ human cells.

Figure 10C:
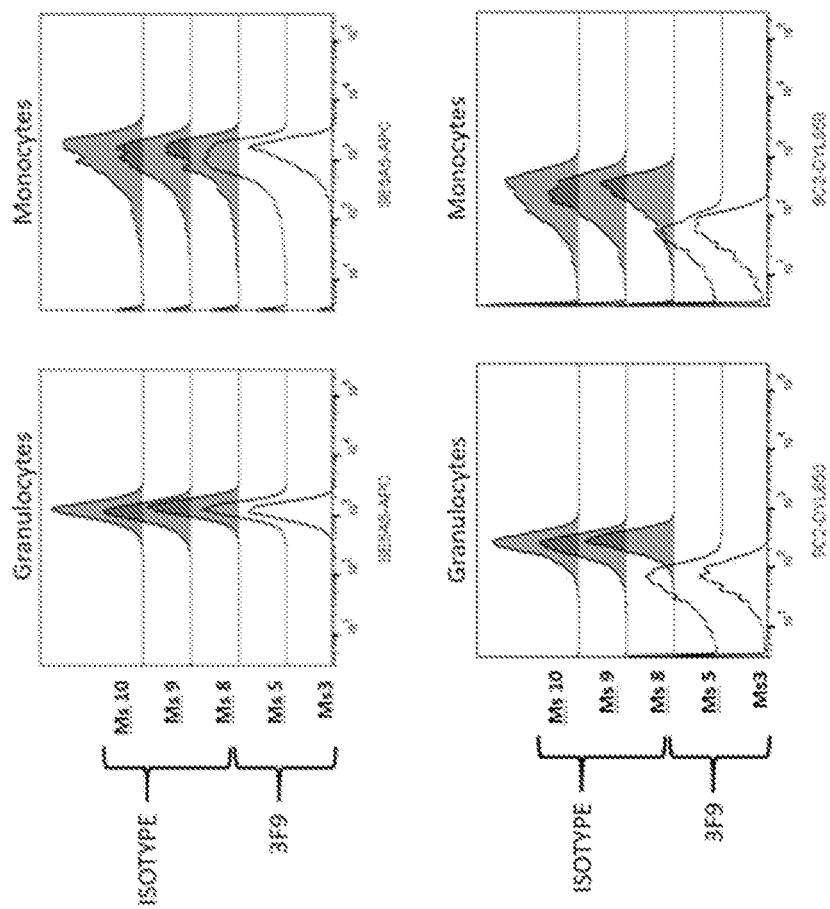
FIG. 10C shows huSIRPA expression in peripheral blood cells from mice administered 10 mg/kg of either 3F9 (solid line histograms) or isotype control (shaded histograms) antibody. The top panel of FIG. 10C shows detection of huSIRPA with a commercial anti-hSIRPα/O-APC (clone SE5A5, Biolegend), an antibody which binds to a different epitope than 3F9. The bottom panel of FIG. 10C shows the detection of huSIRPA with an internally generated anti-hSIRPα-DyLight 650 (clone 9C2), an antibody which binds to the same epitope as 3F9.
Figure 10D:
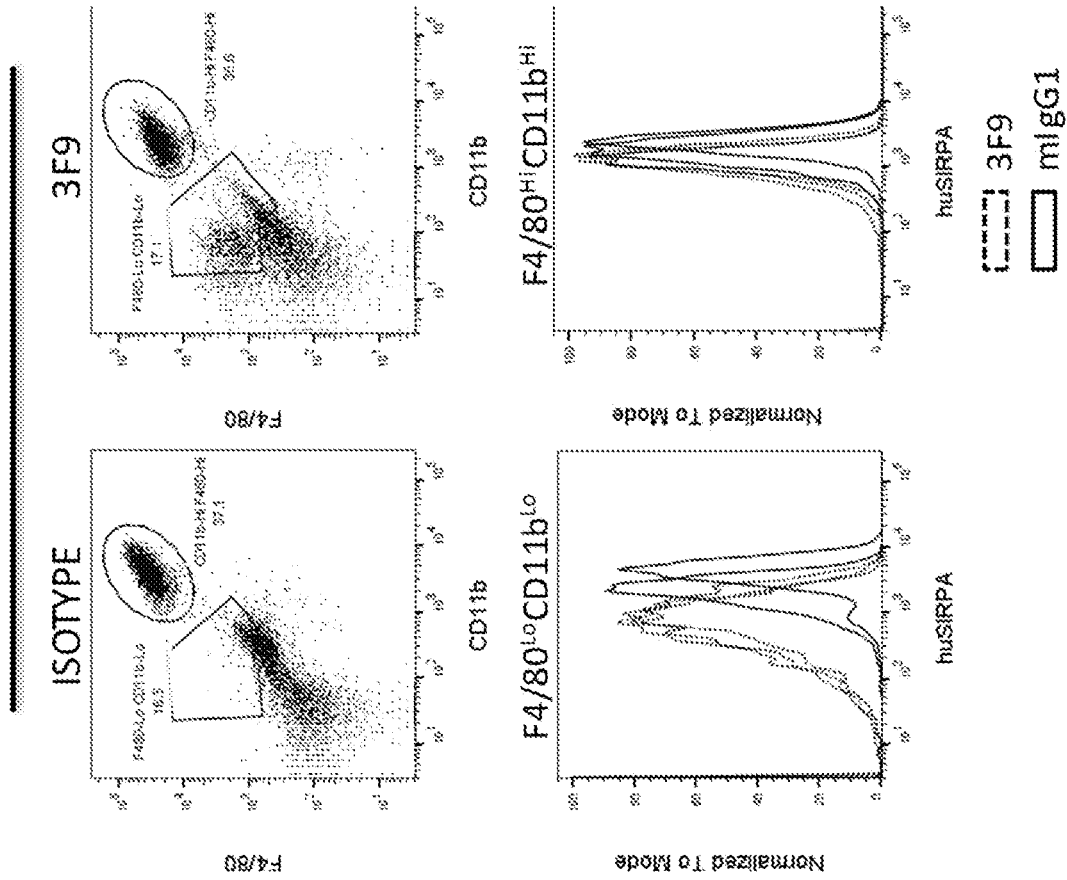
FIG. 10D shows the downregulation of huSIRPA expression in splenocytes following antibody treatment in vivo. The top panel of FIG. 10D shows the gating strategy of single-cell suspensions from mouse spleens stained with anti-mouse F4/80 FITC and anti-mouse CD11b Pacific Blue. The bottom panel of FIG. 10D shows huSIRPA expression from two splenic myeloid populations (F4/80LoCD11bLo and F4/80HiCD11bHi). Solid line histograms represent huSIRPA expression in mice administered isotype control antibody, whereas the dashed line histograms represent huSIRPA expression in mice administered 3F9.

To test antibody-mediated receptor downregulation in vivo, huSIRPA-tg mice received a single intraperitoneal (i.p.) injection of 10 mg/kg of 3F9 (anti-SIRPA antibody) or MOPC21 (mouse IgG1 isotype control). The following day, blood samples were drawn from mice into heparin-coated collection tubes and processed for FACS analysis. Additionally, spleens were also harvested and processed for FACS analysis. Briefly, blood and splenocyte samples were incubated for 5 minutes in ACK lysis buffer to lyse red blood cells and then washed extensively with cold PBS. Cells were then resuspended in FACS buffer (PBS+2% FBS+Fc receptor blocking solution). Peripheral blood myeloid cells were stained with anti-mouse CD11b-Pacific Blue and, either, anti-human SIRPα/β-APC (clone SE5A5) or DyLight 650-conjugated 9C2, the human SIRPA-specific antibody identified through hybridoma screens. Data were acquired on a BD FACS CANTO™ II cytometer (Becton Dickinson) and analyzed with FlowJo software. As shown in FIG. 10C, gating on CD11b+ blood monocytes and granulocytes labeled with anti-human SIRPα/β-APC reveals that 3F9 treatment fails to decrease cell surface levels of huSIRPA on both cell types when compared to isotype control-treated mice. However, 3F9 treatment blocks 9C2-DyLight 650 from binding huSIRPA on peripheral blood cells. Since 3F9 and 9C2 bind to the same epitope, this blockade verifies that 3F9 occupies the receptor on peripheral blood cells without downregulating expression.

Single-cell suspensions from mouse spleens were also obtained from isotype control- and 3F9-treated animals. Splenocytes were stained with anti-mouse CD11b-Pacific Blue, anti-mouse F4/80-FITC, and anti-human SIRPα/β-APC (clone SE5A5). Data were acquired on a BD FACS CANTO™ II cytometer (Becton Dickinson) and analyzed with FlowJo software. As shown if FIG. 10D, two major myeloid cell populations were identified in spleens based on F4/80 and CD11b markers: an $F4/80^{Lo}$ $CD11b^{+/-}$ population (likely red pulp macrophages) and an $F4/80^{Hi}$ $CD11b^{Hi}$ population. Though both populations express huSIRPA, as demonstrated in control-treated mice, 3F9 treatment downregulated huSIRPA expression primarily in $F4/80^{Lo}$ $CD11b^{+/-}$ cells. Additionally, an $F4/80^{Lo}$ $CD11b^-$ population expands in the spleens of 3F9-treated mice only. Marginal decrease in huSIRPA is observed in the $F4/80^{Hi}$ $CD11b^{Hi}$ splenic population.

These results demonstrated that when utilizing huSIRPA-tg mice, anti-SIRPA antibodies engage huSIRPA in vivo and functionally downregulate the receptor on myeloid cells. The results further demonstrate that the huSIRPA antibody, 3F9, engages huSIRPA on peripheral blood cells and splenic myeloid cells, but internalizes the receptor in a cell type-dependent or a context-dependent manner.

Figure 11A:
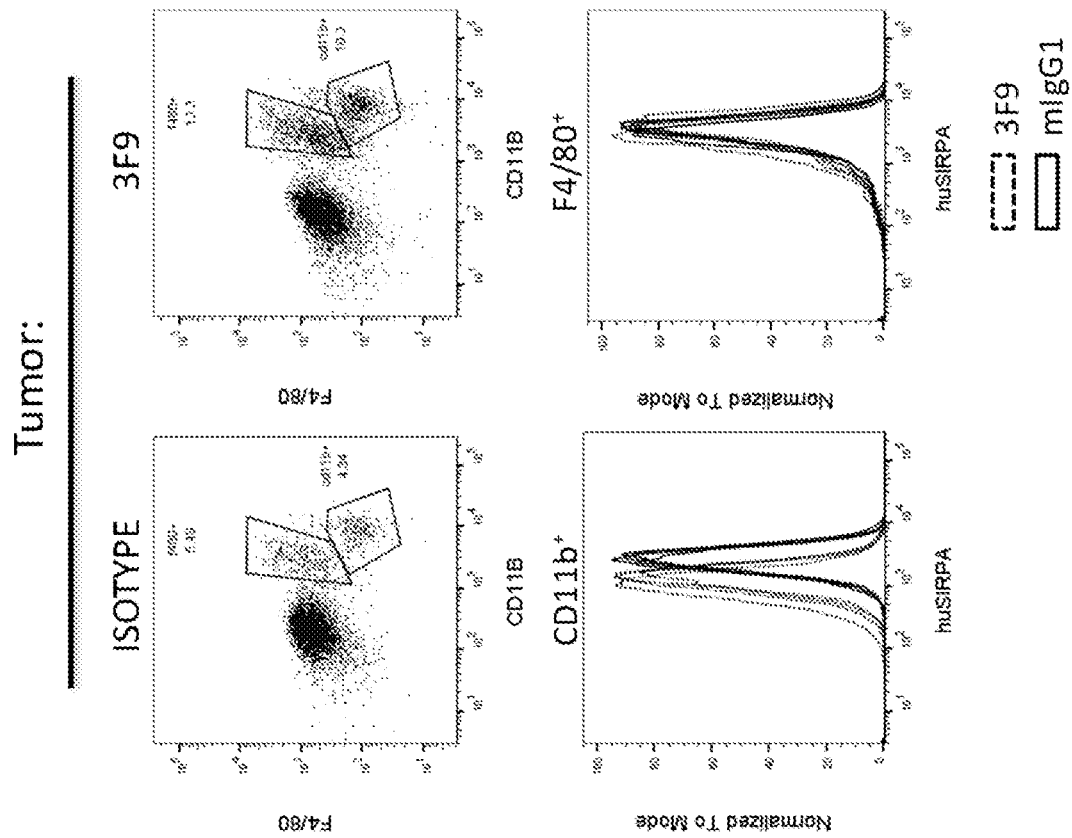
FIG. 11A shows the downregulation of huSIRPA expression in tumor-associated myeloid cells following antibody treatment in vivo. The top panel of FIG. 11A shows the gating strategy of single-cell suspensions from tumors stained with anti-mouse F4/80 FITC and anti-mouse CD11b Pacific Blue. The bottom panel of FIG. 11A shows huSIRPA expression from two splenic myeloid populations (F4/80+ and CD11b+). Solid line histograms represent huSIRPA expression in mice administered isotype control antibody, whereas the dashed line histograms represent huSIRPA expression in mice administered 3F9.

Example 10: Anti-Tumor Effects of Anti-SIRPA Antibodies in BAC-Transgenic Mouse Models Pilot experiments with huSIRPA-tg mice were performed to assess the anti-tumor effects of anti-SIRPA antibodies. Twelve huSIRPA-tg female mice, approximately 8-12 weeks of age, were implanted unilaterally on the right flank with 500,000 Raji-Luciferase cells mixed in Matrigel solution. Tumor engraftment was monitored beginning seven to ten days post-implantation by caliper measurements of tumor volume and bioluminescence imaging. On Day 10, when tumors reached approximately 80-120 mm$^3$ in volume, mice were administered D-luciferin substrate by i.p. injection and imaged with an in vivo imaging system. Mice were subsequently randomized into treatment or control groups (6 mice per group) based on the average radiance (photons/second/cm$^2$/sr) values of the luciferase signal from Raji cells. Beginning on Day 10, mice received i.p. injections at 10 mg/kg of either 3F9 (anti-SIRPA) or mouse IgG1 control antibody 2x/week for the duration of the study. Mice were observed daily and weighed twice weekly using a digital scale. The study was concluded when the mean tumor volume of the control group reached 1500 mm$^3$. At study termination tumors were harvested and processed for FACS analysis. Briefly, tumor samples were treated with collagenase for 30 min at 37° C. Samples were dissociated through a cell strainer and resuspended in 2% FBS in PBS. Red blood cells in samples were lysed using ACK lysis buffer and cells were then washed in 2% FBS in PBS. Cells were counted using a hemocytometer and one million cells were stained with fluorochrome-conjugated antibodies for 30 minutes on ice, then washed with 2% FBS in PBS. Cells were fixed with 4% paraformaldehyde in PBS. All the stained cells were analyzed on a FACS Canto (BD Biosciences) and the data analyzed with FlowJo software (Tree-Star). Tumor-infiltrating myeloid cells were stained with anti-mouse CD11b-Pacific Blue, anti-mouse F4/80-FITC, and anti-human SIRPα/β-APC (clone SE5A5). As shown in FIG. 11A, two major myeloid populations were identified based on F4/80 and CD11b markers: an F4/80$^+$ CD11b$^+$ population (F4/80$^+$ cells) and an F4/80$^-$ CD11b$^+$ population (CD11b+ cells). As shown in isotype control-treated mice, both populations express huSIRPA. However, 3F9 treatment downregulated huSIRPA expression only in F4/80$^-$ CD11b$^+$ cells, whereas huSIRPA expression in F4/80$^+$ CD11b$^+$ cells was not decreased.

Figure 11B:
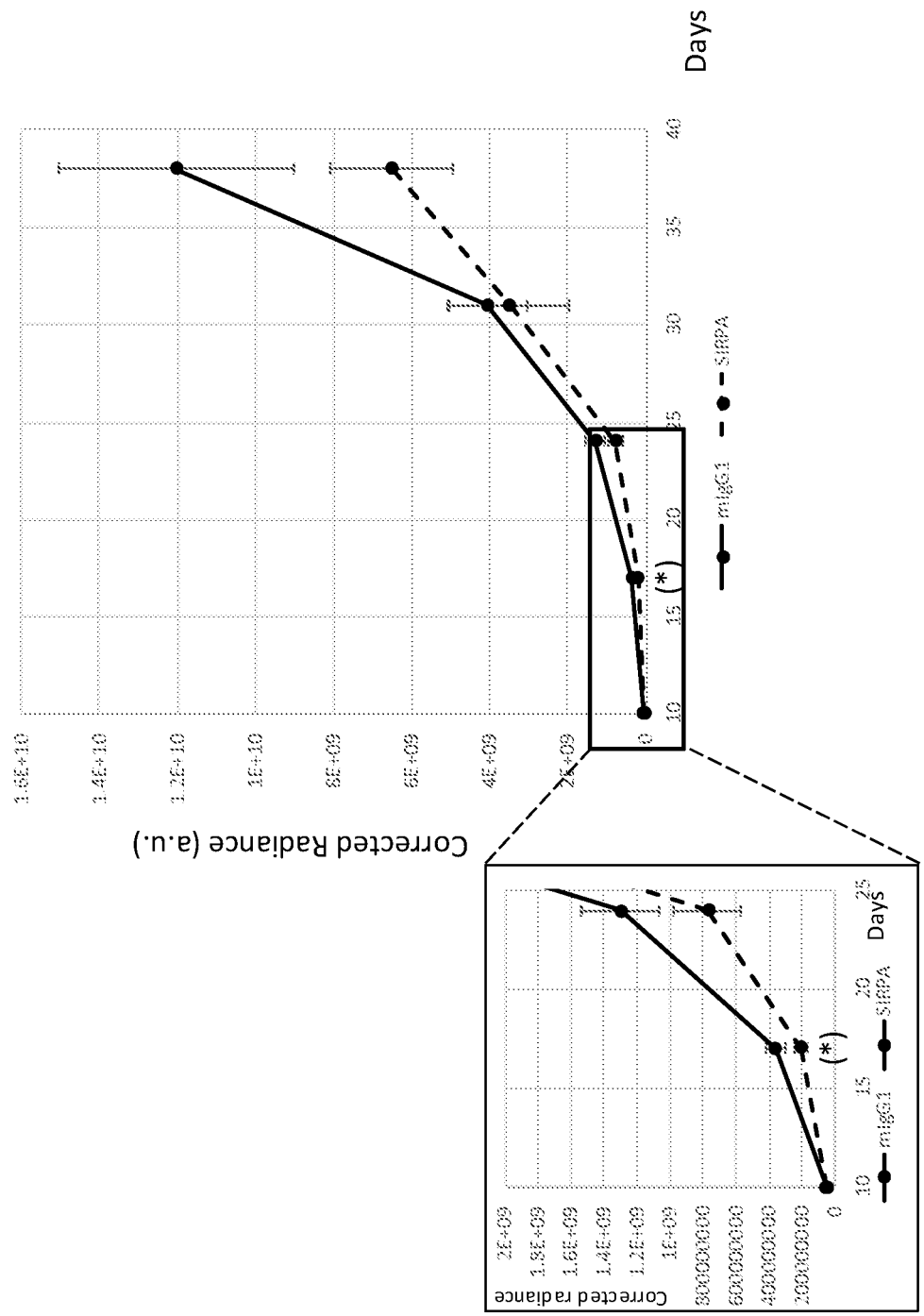
FIG. 11B shows the radiance values of Raji-Luciferase lymphoma cells injected subcutaneously into huSIRPA-tg mice. On Day 10, mice were randomized into treatment or control groups based on radiance values and were dosed with i.p. injections of 3F9 or mouse IgG1 antibody at 10 mg/kg every 3-4 days until study termination. Tumor luminescence values post dosing initiation were corrected for with luminescence values at day of randomization and analyzed by linear regression for significance.

As shown in FIG. 11B, administering the anti-SIRPA antibody, 3F9, appeared to inhibit tumor growth in vivo compared to vehicle control-treated animals when measuring tumor burden by bioluminescent imaging. Linear regression analysis of average radiance values indicates that a near-significant trend for efficacy emerges at Day 17 (p=0.06) when correcting for pre-treatment radiance values at Day 10. This trend continues in subsequent measurements (with p-values of 0.16, 0.77 and 0.18), but given the variability in tumor growth and limited number of huSIRPA-tg mice available, this study is statistically underpowered to reach desired significance levels.

Example 11: Anti-Tumor Effects of Anti-SIRPA Antibodies in Humanized Mouse Models Immunocompromised female NSG mice (Jax) engrafted with human cord blood-derived CD34+ hematopoietic stem cells to reconstitute human immune cell lineages, including the myeloid and lymphoid cell compartments, served as a platform to measure the immune modulating ability of anti-SIRPA antibodies. Successful engraftment of mature human immune cells is defined as >25% of huCD45+ cells in peripheral blood 12 weeks post-injection. Humanized mice were additionally screened for high cell counts of human CD14+, human CD11b+, and human CD33+ cells in peripheral blood.

For immuno-oncology efficacy studies, humanized mice were implanted subcutaneously on the right flank with MDA-MB-231 cells, a triple-negative human breast cancer cell line responsive to checkpoint inhibitor therapy in this model system. Pre-treatment tumor volumes were measured by digital calipers when tumors became palpable, and mice were randomized into treatment or control groups (12 mice per group) when tumor volumes reach 60-120 mm$^3$ on Day −1. Beginning on Day 0, mice received i.p. injections at 40 mg/kg of either 3F9 (anti-SIRPA) or mouse IgG1 control antibody every 4 days for the duration of the study. A third group instead received i.p. injections of pembrolizumab (Keytruda, Merck) at 10 mg/kg every 5 days for the duration of the study. Body weights, clinical observations, and digital caliper measurements were recorded twice weekly post dose initiation. The study was concluded when the mean tumor volume of the control group reached 2000 mm$^3$. At termination, blood, spleen, and tumors were harvested and processed for FACS analysis. Briefly, tumor samples were treated with collagenase for 30 min at 37° C. Spleen and tumor samples were dissociated through a cell strainer and resuspended in 2% FBS in PBS. Red blood cells in samples were lysed using ACK lysis buffer and cells were then washed in 2% FBS in PBS and stained with fluorochrome-conjugated antibodies for 30 minutes on ice. Cells were fixed with 4% paraformaldehyde in PBS. All the stained cells were analyzed on a FACS Canto (BD Biosciences) and the data analyzed with FlowJo software (Tree Star).

Figure 12A:
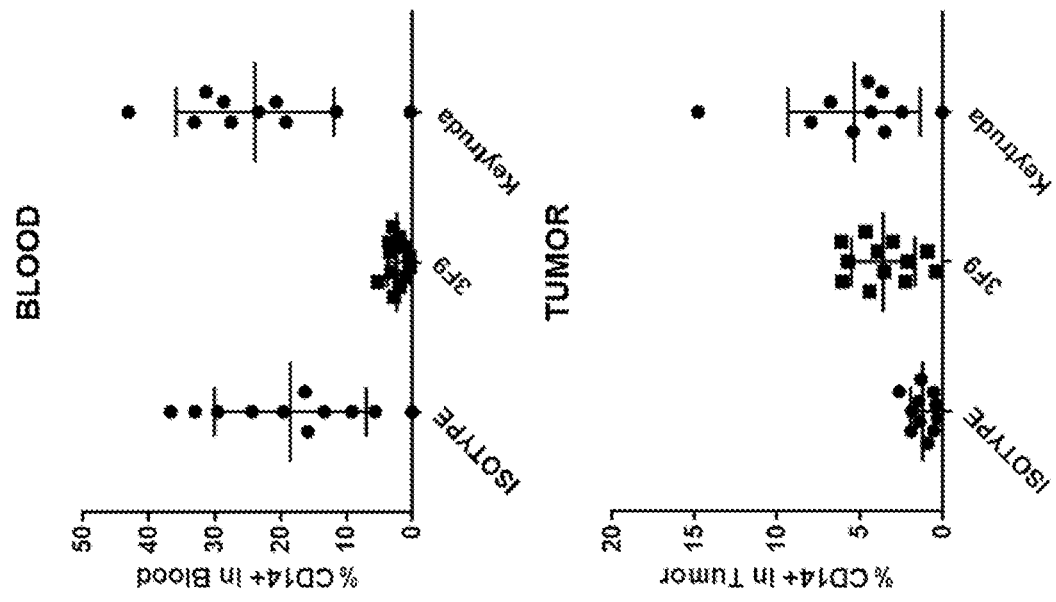
FIG. 12A shows the downregulation of huSIRPA expression huCD45+huCD14+ cells harvested from MDA-MB-231 tumor-bearing humanized mice following antibody treatment in vivo. The top panel of FIG. 12A shows huSIRPA expression level in peripheral blood huCD45+huCD14+ cells from mice administered i.p. injections of either isotype control, 3F9, or Keytruda (pembrolizumab, Merck). The bottom panel of FIG. 12A shows huSIRPA expression level in tumor infiltrating huCD45+huCD14+ cells from mice administered i.p. injections of either isotype control, 3F9, or Keytruda (pembrolizumab, Merck).

As shown in FIG. 12A, treatment with the SIRPA antibody, 3F9, reduced cell surface levels of SIRPA in peripheral blood huCD45+ huCD14+ myeloid cells in tumor-bearing humanized mice when compared to either isotype control-treated or Keytruda-treated mice. However, cell surface expression levels of SIRPA was not reduced on intratumoral huCD45+ huCD14+ myeloid cells. These results resemble previous observations in huSIRPA-tg mice in which antibody-mediated receptor downregulation occurred in a cell type-dependent or context-dependent manner.

Figure 12B:
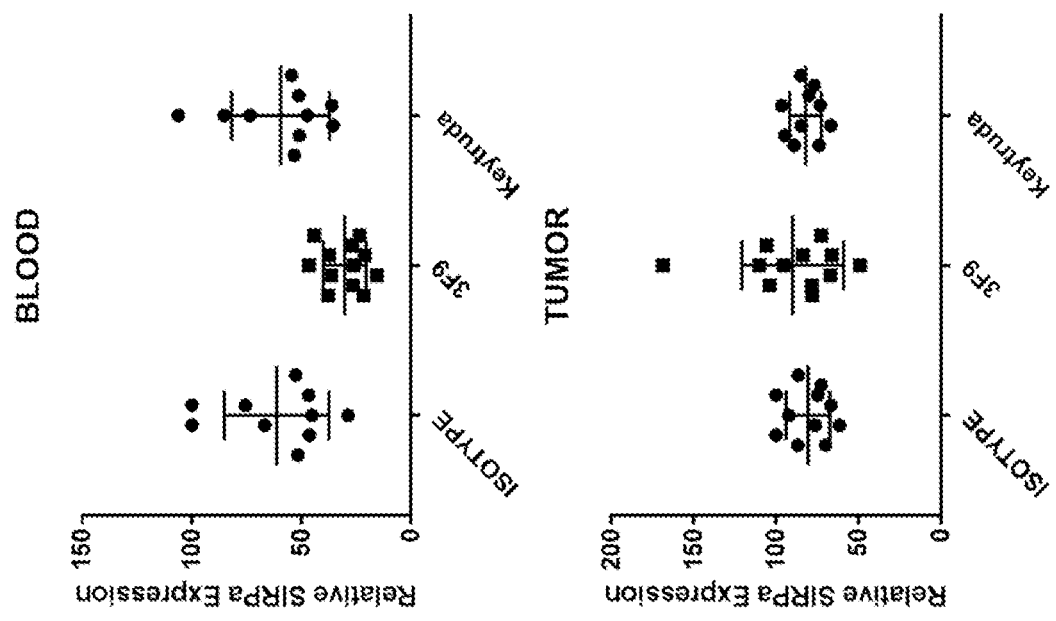
FIG. 12B shows the percent of huCD45+huCD14+ cells present in peripheral blood (FIG. 12B, top panel) or within tumors (FIG. 12B, bottom panel) from mice administered i.p. injections of either isotype control, 3F9, or Keytruda (pembrolizumab, Merck).
Figure 12C:
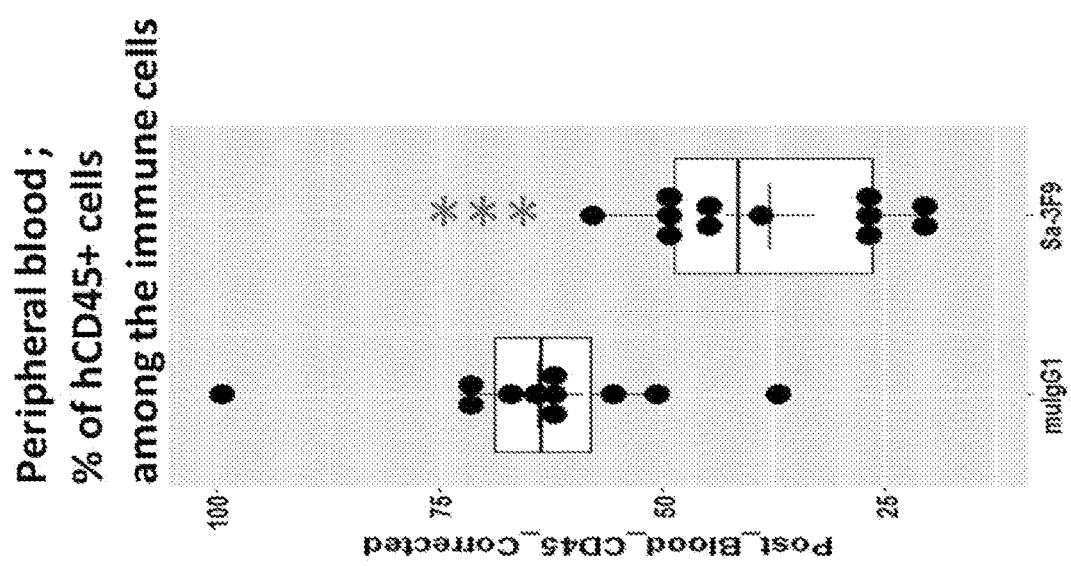
FIG. 12C provides data showing that the % of human CD45+ cells in blood of humanized mice is decreased after dosing with SIRPA antibody 3F9. Data are corrected for donor, initial blood parameters (CD45, CD33, CD3), initial animal weight, and initial tumor volume. ***$p<0.002$ by multiple linear regression (Rlm( ) function) vs control group (muIgG1).

As shown in FIG. 12B, treatment with the SIRPA antibody, 3F9, reduced the percentage of peripheral blood huCD45+ huCD14+ myeloid cells in tumor-bearing humanized mice when compared to either isotype control-treated or Keytruda-treated mice. In contrast, both 3F9 and Keytruda increased the percentage of intratumoral huCD45+ huCD14+ myeloid cells. Furthermore, 3F9 treatment decreased overall percentage of human CD45+ leukocytes in peripheral blood (FIG. 12C) of tumor-bearing humanized mice when compared to the isotype control group.

Figure 13A:
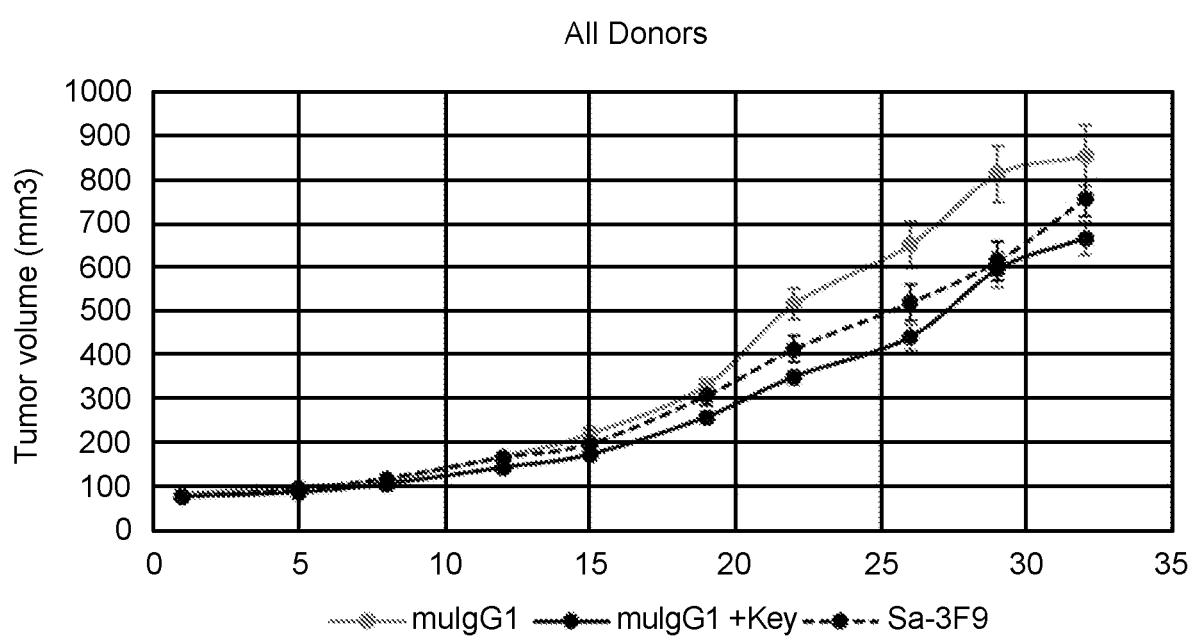
FIG. 13A plots mean tumor volume in NSG mice engrafted with human immune stem cells from various cord blood donors (donors 5031, 5048, 129). Humanized mice were implanted subcutaneously with the human breast cancer cell line MDA-MB-231 and randomized into treatment or control groups based on tumor volume at Day −1, huCD34+ stem cell donor, body weight before randomization, and huC45+ engraftment rate before randomization. Mice were dosed with i.p. injections of either mouse IgG1 or 3F9 at 40 mg/kg every 4 days or Keytruda at 10 mg/kg every 5 days. Solid gray line represents mean tumor volume of isotype control-treated mice, solid black line represents mean tumor volume of Keytruda-treated mice, and dashed black line represents mean tumor volume of 3F9-treated mice.
Figure 16:
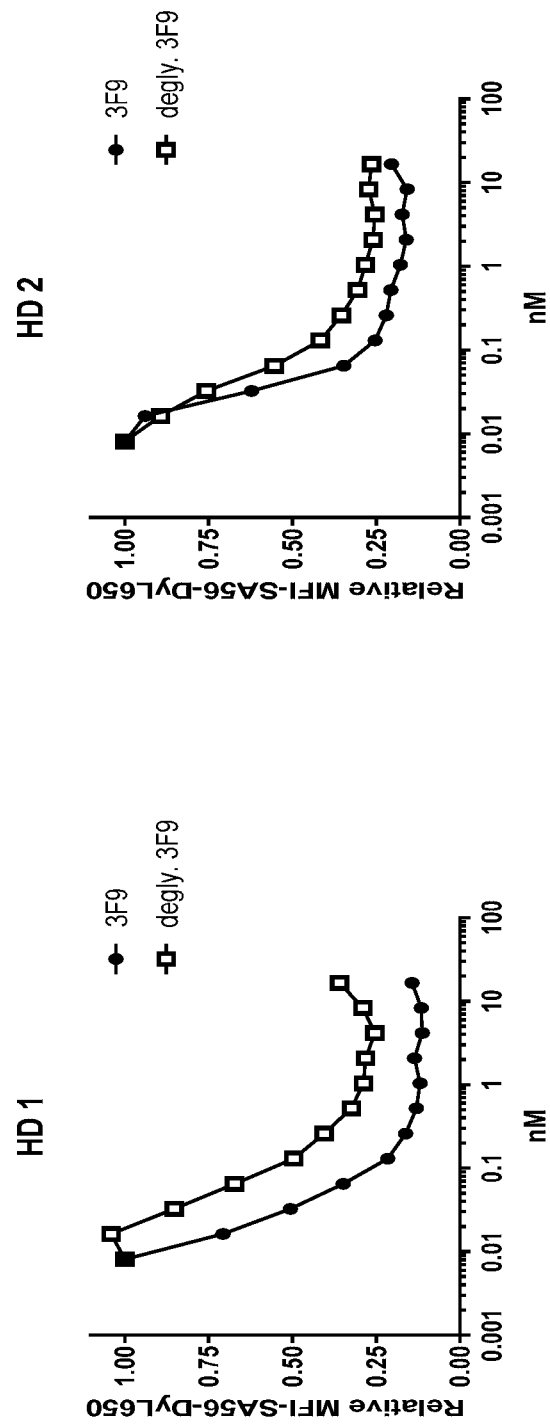
FIG. 16 provides data illustrating that both glycoforms of 3F9 significantly downregulated surface expression of SIRPA relative to isotype control-treated macrophages, but that the deglycosylated form exhibited partially reduced activity compared to the glycosylated form.
Figure 17B:
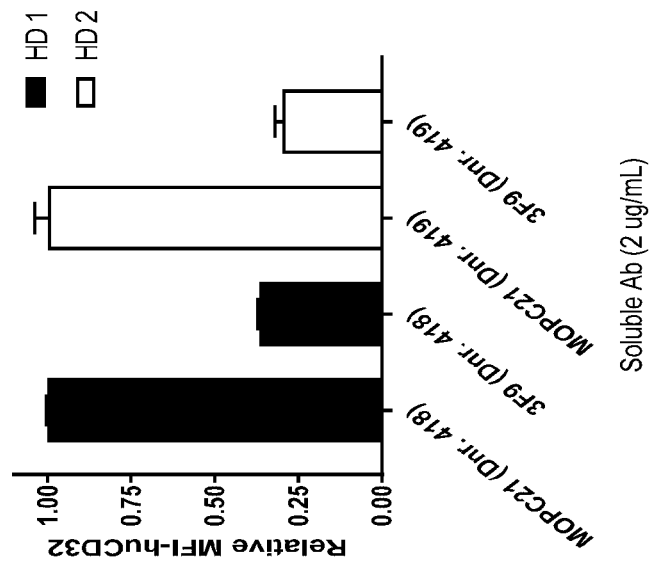
FIGS. 17A and 17B provide data illustrating surface expression levels of FcγRIIIA (panel 18A, CD16) and FcγRIIA/B (panel 18B, CD32A/B) on macrophages treated with control or 3F9 antibody. The antibody used to detect FcγRII for this analysis does not distinguish the activating receptor (FcγRIIA) from the inhibitory receptor (FcγRIIB).
Figure 17A:
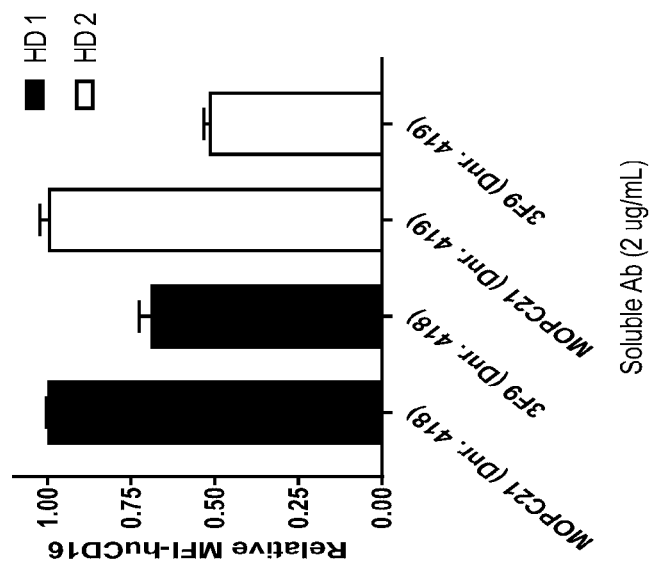
Figure 18:
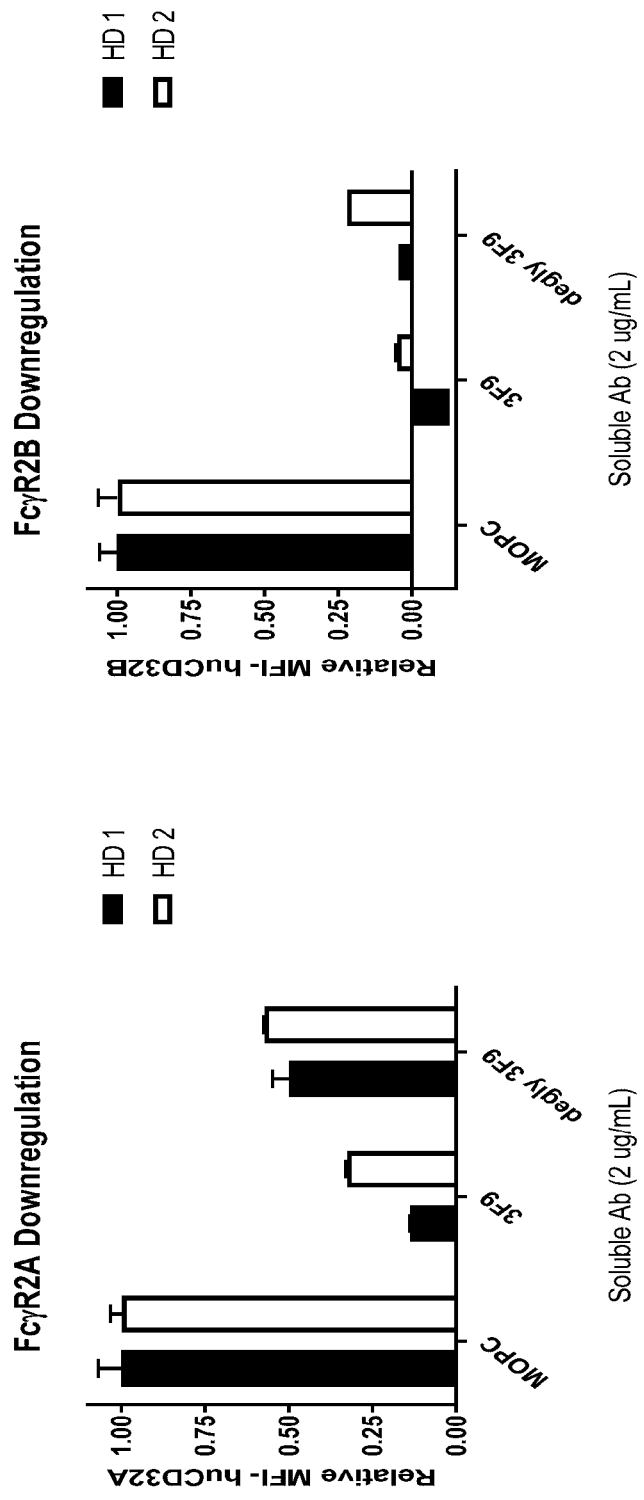
FIG. 18 provides data illustrating cell surface levels of FcγRIIA (left panel) and FcγRIIB (right panel) using receptor-specific antibodies on macrophages treated with glycosylated and deglycosylated forms of 3F9.

To account for various factors other than treatment modality that influence tumor growth in this model system, a multiple linear regression analysis with R's lm( ) function was utilized to correct tumor volumes for differences in 1) huCD34+ stem cell donor, 2) tumor volume at Day −1, 3) animal body weight before randomization, and 4) engraftment rate of huCD45+ cells before randomization. FIG. 13A plots the mean tumor volumes per group for each time point. Both 3F9 and Keytruda treatment groups significantly reduce tumor volume in early and late time points compared to the isotype control group, though the effects are mostly observed between Days 22 and 28. Graphing the tumor volume measurements by huCD34+ stem cell donor, as shown in FIG. 13B, reveals that mice engrafted with human immune cells from donors 5031 and 5048 significantly inhibited tumor growth when treated with either 3F9 or Keytruda compared to isotype control. In contrast, mice engrafted with human immune cells from donor 129 did not record any significant reduction in tumor volume in either treatment group compared to isotype control group. Note, however, that mean tumor volume in the control group from donor 129 recipients was lower than the control group from donors 5031 and 5048. Such donor-to-donor variability in tumor growth underscores the necessity for appropriate controls to adequately interpret results in this platform.

The data presented above establishes that the SIRPA antibody, 3F9, engages the receptor in vivo and induces SIRPA downregulation in specific cell populations. Analysis of both circulating and tumor infiltrating immune cells reveals that 3F9 treatment decreased CD14+ myeloid cells in peripheral blood with a concomitant increase of CD14+ cells in tumors. Unlike Keytruda, which decreased CD4+ and CD8+ T cells in blood and tumors, 3F9 did not significantly impact T cell numbers suggesting that it primarily acts on the myeloid compartment. Importantly, receptor downregulation and changes in myeloid cell populations with 3F9 correlated with significant inhibition of tumor growth comparable to Keytruda therapy. Taken together, these studies support the pre-clinical efficacy of anti-SIRPA antibodies as a therapeutic for treating human cancer.

Example 12: In Silico Antibody Humanization of 3F9 and 9C2

Antibody humanization is used to transform antibodies generated in a different species to best resemble a human antibody through sequence and structural relationships in order to prevent immunogenicity in human administration. Antibodies from different species share characteristic sequence and structural features that allow the grafting of the specificity-determining regions (SDRs) of the non-human antibody onto a human antibody framework. This results in retention of the specificity of the non-human antibody. The humanization process involves identification of the non-human antibody sequence and features, including the framework regions and SDRs. The following criteria are used to humanize an antibody: 1) percent similarity in framework regions between non-human and known human antibodies, 2) length similarity in SDRs between non-human and known human antibodies, 3) genes used to generate the framework regions of the human antibody, and 4) previous use of human antibody frameworks in humanizations and as therapeutics. Similarity in framework regions and SDR lengths are important because differences can generate structural differences in the antibody that can alter the specificity of the antibody. Specific genes used to generate the framework of human antibodies are known to be beneficial or detrimental to the stability or specificity of the antibody and are selectively used or avoided, accordingly. Lastly, previously successful humanization frameworks, including those used in human therapeutics, which are well tolerated with good half-lives, are likely candidates for future successful humanizations.

As shown in FIG. 14A-D, humanized light and heavy chain variable region sequences were identified for SIRPA antibodies, 3F9 and 9C2. The first humanized sequence for 3F9 heavy chain variable domain (hSB-3F9-H1; FIG. 14A) is a "CDR-swap" with no changes to human framework. The subsequent humanized heavy chain sequence (hSB-3F9-H2) alters framework residues (changes shown in bold compared to sequence above it). In FIG. 14B, hSB-3F9-L1 is a "CDR-swap" of the light chain variable domain with no changes to human framework. Subsequent humanized light chain sequences alter framework residues (changes shown in bold compared to sequence above it; gray boxed residues are from a previous version). Light chain CDRs from 3F9 also contain potential deamidation sites (marked with #), which may be substituted with Q, S, A, or D. Additionally, the variable domain for 3F9 contains a potential free Cys at position 96, which may potentially lead to problems during manufacture. This site may be substituted with an A, S, or L residue as long as antigen binding is not altered. In FIG. 14C, hSB-9C2-H1 is a "CDR-swap" of the heavy chain variable domain with no changes to human framework. Subsequent humanized heavy chain sequences alter framework residues (changes shown in bold compared to sequence above it; gray boxed residues are from a previous version). Heavy chain CDRs from 9C2 also contain potential deamidation sites (marked with #), which may be substituted with Q, S, or A. 9C2 also contains an Asp-Gly (DG) sequence in CDR-H3 (marked with @), which may be susceptible to isoaspartate formation. This site may be substituted with an A, S, or E residue as long as antigen binding is not altered. In FIG. 14D, hSB-9C2-L1 is a "CDR-swap" of the light chain variable domain with no changes to human framework. Subsequent humanized light chain sequences alter framework residues (changes shown in bold compared to sequence above it; gray boxed residues are from a previous version). Light chain CDRs from 9C2 contain potential deamidation sites (marked with #), which may be substituted with Q, S, D, or A. 9C2 also contains a Trp residue in CDR-L3 (marked with ^), which may be susceptible to oxidation. This site may be substituted with an H, Y, or F residue as long as antigen binding is not altered.

Example 13: Epitope Mapping of Anti-SIRPA Antibody Binding Sites

Epitope mapping of anti-SIRPA antibodies is performed using an alanine-scanning library created by shotgun mutagenesis of the human SIRPA cDNA sequence. A SIRPA expression construct encoding a C-terminal V5 epitope tag is subjected to high-throughput alanine scanning mutagenesis (outlined in Davidson and Doranz, 2014 Immunology 143, 13-20) to generate a comprehensive mutation library. Each of the residues representing the SIRPA extracellular domain (amino acids 31-374) is mutated, most to alanine, while alanine codons were mutated to serine.

The SIRPA mutant library clones, arrayed in a 384-well microplate, are transfected individually into HEK-293T cells and allowed to express for 22 hours. Antibodies are digested to generate Fabs, after which cells are incubated with Fabs diluted in 10% normal goat serum (NGS) (Sigma-Aldrich, St. Louis, Mo.). Prior to library screening, primary Fab concentrations are determined using an independent immunofluorescence titration curve against cells expressing wild type SIRPA to ensure that signals are within the linear range of detection. Fabs are detected using 7.5 µg/ml AlexaFluor488-conjugated secondary antibody (Jackson ImmunoResearch Laboratories, Westgrove, Pa.) in 10% NGS. Cells are washed twice with PBS and resuspended in Cellstripper (Cellgro, Manassas, Va.) with 0.1% BSA (Sigma-Aldrich, St. Louis, Mo.). In some cases, higher stringency conditions are used, including increased pH, increased temperature, and increased dissociation time. Mean cellular fluorescence is detected using the Intellicyt high throughput flow cytometer (HTFC, Intellicyt, Albuquerque, N. Mex.). Fab reactivities against each mutant clone are calculated relative to wild-type SIRPA protein reactivity by subtracting the signal from mock-transfected controls, and normalizing to the signal from wild-type SIRPA transfected controls.

Mutated residues within library clones are identified as "critical" to the Fab binding epitope if they do not support reactivity of the test Fab but do support reactivity of commercially available reference antibody, MAB4546 (R&D Systems), or additional anti-SIRPA Fabs. This counter-screen strategy facilitates the exclusion of SIRPA mutants that are locally misfolded or that have an expression defect.

Example 14: FcγRIIB Downregulation by Anti-SIRPA Antibodies

In addition to the target antigen of interest, cells of the myeloid lineage also express multiple Fc receptors capable of binding to the Fc domain of therapeutic antibodies. The Fcγ receptors (FcγR) constitute the best characterized and most potent receptor class to mediate Fc-dependent effector functions. FcγRs include both ITAM-associated activating receptors (FcγRI, FcγRIIA, and FcγRIIIA) and an ITIM-bearing inhibitory receptor (FcγRIIB), and co-expression of activating/inhibitory receptors on the same cell establishes a threshold for cellular activation. In general, ligation of activating FcγRs by immune complexes initiates several signaling cascades that lead to cellular activation and subsequent induction of effector functions. These activities vary between myeloid cell types, but may include antibody-dependent cellular cytotoxicity, antibody-dependent cellular phagocytosis, and upregulation of several pro-inflammatory cytokines and chemokines, etc. In contrast, ligation of the inhibitory receptor, FcγRIIB, by immune complexes counteracts the immunostimulatory signals of activating FcγRs supporting the maintenance of tissue homeostasis. For example, several studies establish that genetic knockout of FcγRIIB results in enhanced pro-inflammatory macrophage activity in murine models of immune complex-mediated inflammation. Since FcγRIIB is the only FcγR with inhibitory activity, it plays a central role in regulating FcγR-mediated inflammation by myeloid cells. In the context of the tumor microenvironment, FcγRIIB expression levels may determine the polarization state of tumor-associated macrophages and the regulation of macrophage effector function in vivo.

To assess whether FcγRs participate in the in vitro activity of anti-SIRPA antibodies, antibody 3F9, was treated with EndoS (New England Biolabs) to remove the Fc-linked glycan. The enzymatic reaction completely cleaved the carbohydrate structure as shown by the LCA blot in FIG. 15A, which detects the mannose residues on the Fc glycan. Importantly, the deglycosylation reaction did not impact antigen recognition as both 3F9 and deglycosylated 3F9 bound SIRPA comparably in cell-based binding assays (FIG. 15B). Subsequently, the ability of deglycosylated 3F9 to reduce cell surface expression of SIRPA on primary human macrophages (huMacs) was compared to glycosylated 3F9. Briefly, human monocytes were isolated from peripheral blood of two healthy donors (HD 1 and HD 2) and differentiated into macrophages in vitro. Following differentiation, $10^5$ huMacs were harvested and seeded onto 96-well tissue culture plates with increasing concentrations of anti-SIRPA antibodies. Cells were analyzed by flow cytometry for SIRPA surface expression following overnight incubation. Receptor expression was detected using a DyLight650-conjugated anti-human SIRPA antibody belonging to a separate epitope bin than 9C2 and 3F9.

As shown in FIG. 16, both glycoforms of 3F9 significantly downregulated surface expression of SIRPA relative to isotype control-treated macrophages. However, in both donors, the deglycosylated 3F9 variant exhibited partially reduced activity compared to the glycosylated antibody. For example, 3F9 downregulated SIRPA expression by as much as 90% and 85% in HD 1 and HD 2, respectively; whereas deglycosylated 3F9 only achieved 70% and 75% receptor downregulation in the same donor macrophages, respectively. This finding suggests that anti-SIRPA antibodies such as 3F9 need FcγR engagement for maximal activity.

To determine which FcγR contributes to the in vitro activity of 3F9, monocyte-derived macrophages obtained from two healthy donors were treated overnight with either isotype control antibody or anti-SIRPA antibody, 3F9, and assessed for surface expression levels of FcγRIIIA (CD16) and FcγRIIA/B (CD32A/B). As shown in FIG. 17A, 3F9 treatment moderately reduced surface expression of FcγRIIIA relative to isotype control-treated macrophages. In contrast, substantial downregulation of FcγRIIA/B was evident on 3F9-treated macrophages relative to isotype control-treated cells (FIG. 17B).

Since the detection antibody used to measure surface levels of FcγRII (clone FUN-2; Biolegend) does not distinguish the activating receptor (FcγRIIA) from the inhibitory receptor (FcγRIIB), this assay was repeated with receptor-specific antibodies. As previously described, monocyte-derived macrophages obtained from two healthy donors were treated overnight with either isotype control antibody or the indicated glycoform of 3F9. FIG. 18 shows that 3F9 significantly downregulated FcγRIIA in macrophages by ~70-85% relative to isotype control-treated cells. This effect was dependent on the Fc domain since deglycosylation of the antibody abrogated receptor downregulation. However, when assessing surface expression of FcγRIIB, 3F9 treatment reduced expression of the inhibitory receptor to near undetectable levels relative to isotype control-treated macrophages (FIG. 18). Even the deglycosylated form of 3F9 exhibited robust downregulation of FcγRIIB suggesting that the murine IgG1 isoform of 3F9 may preferentially associate with human FcγRIIB. Not to be bound by theory, by targeting two ITIM-bearing receptors for downregulation (SIRPA and FcγRIIB), 3F9 may polarize macrophages towards an activated phenotype. In the context of tumor biology, reprogramming tumor-associated macrophages in the tumor microenvironment from a pro-tumor phenotype towards an anti-tumor phenotype with an anti-SIRPA antibody thus represents a promising mode of cancer immunotherapy.

All patents, patent applications, accession numbers, and other published reference materials cited in this specification are hereby incorporated herein by reference in their entirety for their disclosures of the subject matter in whose connection they are cited herein.

What is claimed is:

1. An isolated anti-signal regulatory protein a (SIRPA) antibody, wherein the anti-SIRPA antibody comprises a heavy chain variable region (VH) that comprises a complementarity determining region 1 (CDR1) comprising the amino acid sequence of SEQ ID NO:9, a CDR2 comprising the amino acid sequence of SEQ ID NO:10, and a CDR3 comprising the amino acid sequence of SEQ ID NO:11; and a light chain variable region (VL) that comprises a CDR1 comprising the amino acid sequence of SEQ ID NO:6, a CDR2 comprising the amino acid sequence of SEQ ID NO:7, and a CDR3 comprising the amino acid sequence of SEQ ID NO:8.

2. The anti-SIRPA antibody of claim 1, wherein the antibody does not substantially block binding of CD47 to SIRPA expressed on cells, wherein binding of the antibody to SIRPA decreases the level of SIRPA expressed on the cell surface, and/or wherein the antibody binds to the D2 domain of SIRPA, or the D3 domain of SIRPA.

3. The anti-SIRPA antibody of claim 1, wherein the antibody competes with an antibody comprising a VH sequence comprising the amino acid sequence of SEQ ID NO:2 and a VL sequence comprising the amino acid sequence of SEQ ID NO:3.

4. The anti-SIRPA antibody of claim 1, wherein the VH comprises an amino acid sequence having at least 90%, at least 91%, at least 92%, at least 93%, at least 94%, at least 95%, at least 96%, at least 97%, at least 98%, or at least 99% sequence identity to the amino acid sequence of hSB-3F9-H1 or hSB-3F9-H2.

5. The anti-SIRPA antibody of claim 1, wherein the VL comprises an amino acid sequence having at least 90%, at least 91%, at least 92%, at least 93%, at least 94%, at least 95%, at least 96%, at least 97%, at least 98%, or at least 99% sequence identity to the amino acid sequence of hSB-3F9-L1, hSB-3F9-L2, or hsB-3F9-L3.

6. The isolated anti-SIRPA antibody of claim 1, comprising a VH region comprising the amino acid sequence of SEQ ID NO:2 and a VL region comprising the amino acid sequence of SEQ ID NO:3.

7. The anti-SIRPA antibody of claim 1, wherein the antibody is a monoclonal antibody.

8. The anti-SIRPA antibody of claim 1, wherein the antibody is a humanized antibody.

9. The anti-SIRPA antibody of claim 1, wherein the antibody is an Fab, Fab', Fab'-SH, F(ab')2, Fv or scFv fragment.

10. The anti-SIRPA antibody of claim 1, wherein the anti-SIRPA antibody has an IgG1, IgG2, IgG3, or IgG4 isotype.

11. The anti-SIRPA antibody of claim 10, wherein:
(a) the anti-SIRPA antibody has a human IgG1 isotype and comprises one or more amino acid substitutions in the Fc region at a residue position selected from the group consisting of: N297A, D265A, D270A, L234A, L235A, G237A, P238D, L328E, E233D, G237D, H268D, P271G, A330R, C226S, C229S, E233P, L234V, L234F, L235E, P331S, S267E, L328F, A330L, M252Y, S254T, T256E, N297Q, P238S, P238A, A327Q, A327G, P329A, K322A, T394D, and any combination thereof, wherein the numbering of the residues is according to EU numbering, or comprises an amino acid deletion in the Fc region at a position corresponding to glycine 236;
(b) the anti-SIRPA antibody has an IgG1 isotype and comprises an IgG2 isotype heavy chain constant domain 1(CH1) and hinge region, optionally wherein the IgG2 isotype CH1 and hinge region comprises the amino acid sequence of ASTKGPSVFP LAPCSRSTSE STAALGCLVK DYFPEPVTVS WNSGALT-SGVHTFPAVLQSS GLYSLSSVVT VPSSNFGTQT YTCNVDHKPS NTKVDKTVERKCCVECPPCP (SEQ ID NO:34), and optionally wherein the antibody Fc region comprises a S267E amino acid substitution, a L328F amino acid substitution, or both, and/or a N297A or N297Q amino acid substitution, wherein the numbering of the residues is according to EU numbering;
(c) the anti-SIRPA antibody has an IgG2 isotype and comprises one or more amino acid substitutions in the Fc region at a residue position selected from the group consisting of: P238S, V234A, G237A, H268A, H268Q, V309L, A330S, P331S, C214S, C232S, C233S, S267E, L328F, M252Y, S254T, T256E, H268E, N297A, N297Q, A330L, and any combination thereof, wherein the numbering of the residues is according to EU numbering;
(d) the anti-SIRPA antibody has a human IgG4 isotype and comprises one or more amino acid substitutions in the Fc region at a residue position selected from the group consisting of: L235A, G237A, S228P, L236E, S267E, E318A, L328F, M252Y, S254T, T256E, E233P, F234V, L234A/F234A, S228P, S241P, L248E, T394D, N297A, N297Q, L235E, and any combination thereof, wherein the numbering of the residues is according to EU numbering; or
(e) the anti-SIRPA antibody has a hybrid IgG2/4 isotype, and optionally wherein the antibody comprises an amino acid sequence comprising amino acids 118 to 260 of human IgG2 and amino acids 261 to 447 of human IgG4, wherein the numbering of the residues is according to EU numbering.

12. The anti-SIRPA antibody of claim 1, wherein the anti-SIRPA antibody is conjugated to a detectable marker, a toxin, or a therapeutic agent.

13. The anti-SIRPA antibody of claim 12, wherein the anti-SIRPA antibody is conjugated to a toxin selected from the group consisting of ricin, ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin.

14. A pharmaceutical composition comprising an anti-SIRPA antibody of claim 1 and a physiologically acceptable carrier.

15. The anti-SIRPA antibody of claim 1, wherein the VH comprises the amino acid sequence of hSB-3F9-H1 or hSB-3F9-H2.

16. The anti-SIRPA antibody of claim 1, wherein the VL comprises the amino acid sequence of hSB-3F9-L1, hSB-3F9-L2, or hsB-3F9-L3.

17. The anti-SIRPA antibody of claim 1, wherein the VH comprises the amino acid sequence of hSB-3F9-H1 or hSB-3F9-H2 and wherein the VL comprises the amino acid sequence of hSB-3F9-L1, hSB-3F9-L2, or hsB-3F9-L3.

18. The anti-SIRPA antibody of claim 1, wherein the VH comprises the amino acid sequence of SEQ ID NO: 2.

19. The anti-SIRPA antibody of claim 1, wherein the VL comprises the amino acid sequence of SEQ ID NO: 3.

20. The anti-SIRPA antibody of claim 10, wherein the anti-SIRPA antibody has a human IgG1 isotype and wherein the Fc region comprises substitution P331S; or substitutions L234A, L235A, and P331S; or substitutions S267E and L328F.

* * * * *

SEQUENCE LISTING

<160> NUMBER OF SEQ ID NOS: 74

<210> SEQ ID NO 1
<211> LENGTH: 504
<212> TYPE: PRT
<213> ORGANISM: Homo sapiens

<400> SEQUENCE: 1

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365
```

```
Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500
```

<210> SEQ ID NO 2
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Asp Tyr Gly Gly Ser Tyr Thr Tyr Tyr Pro Asp Ser
    50                  55                  60

Val Lys Gly Arg Phe Thr Ile Ser Arg Asp Asn Ala Lys Tyr Thr Leu
65                  70                  75                  80

Tyr Leu Gln Met Ser Ser Leu Arg Ser Glu Asp Thr Ala Leu Tyr Tyr
                85                  90                  95

Cys Ala Arg Pro Pro Tyr Asp Asp Tyr Tyr Gly Gly Phe Ala Tyr Trp
            100                 105                 110

Gly Gln Gly Thr Leu Val Thr Val Ser Ala
        115                 120
```

<210> SEQ ID NO 3
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
```

```
                    20                  25                  30

Gly Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Asn Arg
                85                  90                  95

Glu Leu Pro Cys Thr Phe Gly Gly Gly Thr Lys Leu Glu Ile Lys
            100                 105                 110

<210> SEQ ID NO 4
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Phe Gln Leu Gln Gln Ser Gly Ala Glu Leu Val Lys Pro Gly Ala
1               5                   10                  15

Ser Val Lys Ile Ser Cys Lys Ala Ser Gly Tyr Ser Leu Thr Gly Tyr
                20                  25                  30

Asn Met Asn Trp Val Lys Gln Ser Arg Gly Lys Ser Leu Glu Trp Ile
            35                  40                  45

Gly Asn Ile Asn Pro His Tyr Gly Ser Ser Thr Tyr Asn Gln Asn Phe
        50                  55                  60

Lys Asp Lys Ala Thr Leu Thr Val Asp Lys Ser Ser Ala Ala Ala Tyr
65                  70                  75                  80

Met Gln Phe Asn Ser Leu Thr Ser Glu Asp Ser Ala Val Tyr Tyr Cys
                85                  90                  95

Ala Arg Glu Gly Tyr Asp Gly Val Phe Asp Tyr Trp Gly Gln Gly Thr
            100                 105                 110

Thr Leu Thr Val Ser Ser
        115

<210> SEQ ID NO 5
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
            35                  40                  45

Val Thr Ser Asn Leu Ala Ser Gly Val Pro Thr Arg Phe Ser Gly Ser
        50                  55                  60

Gly Ser Gly Thr Ser Tyr Ser Leu Thr Ile Ser Arg Val Glu Ala Glu
65                  70                  75                  80
```

Asp Ala Ala Thr Tyr Tyr Cys Gln Gln Trp Ser Ser Asn Pro Arg Thr
            85                  90                  95

Phe Gly Gly Gly Thr Lys Leu Glu Ile Lys
            100                 105

<210> SEQ ID NO 6
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Arg Ala Ser Lys Ser Val Ser Ser Ser Gly Tyr Ser Tyr Met His
1               5                   10                  15

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Leu Ala Ser Asn Leu Glu Ser
1               5

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln His Asn Arg Glu Leu Pro Cys Thr
1               5

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Phe Thr Phe Ser Ser Tyr Ala Met Ser
1               5                   10

<210> SEQ ID NO 10
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Thr Ile Ser Asp Tyr Gly Gly Ser Tyr Thr Tyr
1               5                   10

<210> SEQ ID NO 11
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Pro Pro Tyr Asp Asp Tyr Tyr Gly Gly Phe Ala Tyr
1               5                   10

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Arg Ala Ser Ser Ser Val Ser Tyr Met His
1               5                   10

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Val Thr Ser Asn Leu Ala Ser
1               5

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gln Gln Trp Ser Ser Asn Pro Arg Thr
1               5

<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Tyr Ser Leu Thr Gly Tyr Asn Met Asn
1               5                   10

-continued

```
<210> SEQ ID NO 16
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Asn Ile Asn Pro His Tyr Gly Ser Ser Thr
1               5                   10

<210> SEQ ID NO 17
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Glu Gly Tyr Asp Gly Val Phe Asp Tyr
1               5

<210> SEQ ID NO 18
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Glu Val Lys Leu Val Glu Ser Gly Gly Gly Leu Val Lys Pro Gly Gly
1               5                   10                  15

Ser Leu Lys Leu Ser Cys Ala Ala Ser
            20                  25

<210> SEQ ID NO 19
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Trp Val Arg Gln Thr Pro Glu Lys Arg Leu Glu Trp Val Ala
1               5                   10

<210> SEQ ID NO 20
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Tyr Pro Asp Ser Val Lys Gly Arg Phe Thr Ile Ser Arg Asp Asn Ala
1               5                   10                  15

Lys Tyr Thr Leu Tyr Leu Gln Met Ser Ser Leu Arg Ser Glu Asp Thr
            20                  25                  30
```

Ala Leu Tyr Tyr Cys Ala Arg
      35

<210> SEQ ID NO 21
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Trp Gly Gln Gly Thr Leu Val Thr Val Ser Ala
1               5                   10

<210> SEQ ID NO 22
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 23
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Trp Tyr Gln Gln Lys Pro Gly Gln Pro Pro Lys Leu Leu Ile Tyr
1               5                   10                  15

<210> SEQ ID NO 24
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30

<210> SEQ ID NO 25
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Phe Gly Gly Gly Thr Lys Leu Glu Ile Lys
1               5                   10

<210> SEQ ID NO 26
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Glu Phe Gln Leu Gln Gln Ser Gly Ala Glu Leu Val Lys Pro Gly Ala
1               5                   10                  15

Ser Val Lys Ile Ser Cys Lys Ala Ser
            20                  25

<210> SEQ ID NO 27
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Trp Val Lys Gln Ser Arg Gly Lys Ser Leu Glu Trp Ile Gly
1               5                   10

<210> SEQ ID NO 28
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Tyr Asn Gln Asn Phe Lys Asp Lys Ala Thr Leu Thr Val Asp Lys Ser
1               5                   10                  15

Ser Ser Ala Ala Tyr Met Gln Phe Asn Ser Leu Thr Ser Glu Asp Ser
            20                  25                  30

Ala Val Tyr Tyr Cys Ala Arg
        35

<210> SEQ ID NO 29
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Trp Gly Gln Gly Thr Thr Leu Thr Val Ser Ser
1               5                   10

<210> SEQ ID NO 30
<211> LENGTH: 23
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gln Ile Val Leu Ser Gln Ser Pro Ala Ile Leu Ser Ala Ser Pro Gly
1               5                   10                  15

Glu Lys Val Thr Met Thr Cys
            20

<210> SEQ ID NO 31
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Trp Tyr Gln Gln Lys Pro Gly Ser Ser Pro Lys Pro Trp Ile Tyr
1               5                   10                  15

<210> SEQ ID NO 32
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gly Val Pro Thr Arg Phe Ser Gly Ser Gly Ser Gly Thr Ser Tyr Ser
1               5                   10                  15

Leu Thr Ile Ser Arg Val Glu Ala Glu Asp Ala Ala Thr Tyr Tyr Cys
            20                  25                  30

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Phe Gly Gly Gly Thr Lys Leu Glu Ile Lys
1               5                   10

<210> SEQ ID NO 34
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro
            100                 105                 110

<210> SEQ ID NO 35
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Ser Gly Tyr Gly Lys Tyr Asp Phe Asp Tyr Trp Gly Gln Gly
            100                 105                 110

Thr Thr Leu Thr Val Ser Ser
        115

<210> SEQ ID NO 36
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80
```

Pro Val Glu Glu Glu Asp Thr Ala Thr Tyr Tyr Cys Gln His Asn Trp
            85                  90                  95

Glu Ile Pro Trp Thr Phe Gly Gly Gly Thr Lys Leu Glu Ile Lys
            100                 105                 110

<210> SEQ ID NO 37
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gln Ile Gln Leu Val Gln Ser Gly Pro Glu Leu Lys Lys Pro Gly Glu
1               5                   10                  15

Thr Val Lys Ile Ser Cys Lys Ala Ser Asp Tyr Thr Phe Thr Asp Tyr
                20                  25                  30

Ser Met His Trp Val Lys Gln Ala Pro Gly Lys Asp Leu Lys Trp Met
            35                  40                  45

Gly Trp Ile Asn Thr Glu Thr Gly Glu Pro Thr Tyr Ala Asp Asp Phe
        50                  55                  60

Lys Gly Arg Phe Ala Phe Ser Leu Glu Ala Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg His Gly Tyr Pro His Tyr Tyr Phe Asp Tyr Trp Gly Gln Gly
            100                 105                 110

Thr Thr Leu Thr Val Ser Ser
        115

<210> SEQ ID NO 38
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Pro Thr Ala
                20                  25                  30

Val Ala Trp Tyr Gln Gln Lys Pro Gly Gln Ser Pro Lys Ala Leu Ile
            35                  40                  45

Tyr Leu Ala Ser Asn Arg His Thr Gly Val Pro Asp Arg Phe Thr Gly
        50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Leu Gln His Trp Asn Tyr Pro Arg
                85                  90                  95

Thr Phe Gly Gly Gly Thr Lys Leu Glu Ile Lys
            100                 105

<210> SEQ ID NO 39
<211> LENGTH: 121
<212> TYPE: PRT

<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 39

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Ser Phe Ser Ser Tyr
            20                  25                  30

Ala Met Ser Trp Val Arg Gln Thr Pro Ala Lys Arg Leu Glu Trp Val
        35                  40                  45

Ala Thr Ile Ser Gly Ser Gly Gly Tyr Thr Tyr Tyr Pro Asp Ser Met
    50                  55                  60

Lys Gly Arg Phe Thr Ile Ser Arg Asp Asn Ala Lys Asp Ile Leu Tyr
65                  70                  75                  80

Leu Gln Met Ser Ser Leu Arg Ser Glu Asp Thr Ala Met Tyr Tyr Cys
                85                  90                  95

Ala Arg Asp Pro Arg Tyr Thr Thr Leu Tyr Ala Met Asp Tyr Trp Gly
            100                 105                 110

Gln Gly Thr Ser Val Thr Val Ser Ser
            115                 120

<210> SEQ ID NO 40
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 40

Asn Ile Met Met Thr Gln Ser Pro Ser Phe Leu Ala Val Ser Ala Gly
1               5                   10                  15

Glu Lys Val Thr Met Ser Cys Lys Ser Ser Gln Ser Ile Phe Ser Gly
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

His Leu Ser Ser Cys Thr Phe Gly Gly Gly Thr Lys Leu Glu Ile Lys
            100                 105                 110

<210> SEQ ID NO 41
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 41

Asp Val Gln Leu Gln Glu Ser Gly Pro Gly Leu Val Lys Pro Ser Gln
1               5                   10                  15

```
Ser Leu Ser Leu Thr Cys Thr Val Thr Gly Phe Ser Ile Ser Arg Gly
            20                  25                  30

Tyr Asp Trp His Trp Ile Arg His Phe Pro Gly Asn Ile Leu Glu Trp
            35                  40                  45

Met Gly Tyr Ile Thr Tyr Ser Gly Ile Ser Asn Tyr Asn Pro Ser Leu
 50                      55                  60

Lys Ser Arg Ile Ser Ile Thr His Asp Thr Ser Lys Asn His Phe Phe
 65                  70                  75                  80

Leu Arg Leu Asn Ser Val Thr Ala Glu Asp Thr Ala Thr Tyr Tyr Cys
                    85                  90                  95

Ala Arg Gly Gly Gly Ala Trp Phe Thr Tyr Trp Gly Gln Gly Thr Leu
                100                 105                 110

Val Thr Val Ser Ala
            115

<210> SEQ ID NO 42
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Ser
                20                  25                  30

Leu His Trp Tyr His Gln Lys Ser His Glu Ser Pro Arg Leu Leu Ile
            35                  40                  45

Lys Tyr Ala Ser Gln Ser Ile Ser Gly Ile Pro Ser Arg Phe Ser Ala
 50                  55                      60

Gly Gly Ser Gly Ser Asp Phe Thr Leu Thr Ile Asn Ser Val Glu Pro
 65                  70                  75                  80

Glu Asp Val Gly Val Tyr Tyr Cys Gln Asn Gly His Ser Leu Pro Trp
                85                  90                  95

Thr Phe Gly Gly Gly Thr Lys Leu Glu Ile Lys
            100                 105

<210> SEQ ID NO 43
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Glu Val Lys Leu Glu Glu Ser Gly Gly Gly Leu Val Lys Pro Gly Gly
 1               5                  10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Gly Lys Thr Thr Asn Tyr Ala Thr Tyr Tyr Ala Glu
 50                  55                  60
```

```
Ser Val Lys Gly Arg Phe Thr Ile Ser Arg Asp Asp Ser Lys Ser Ser
 65                  70                  75                  80

Val Tyr Leu Gln Met Asn Ser Phe Ser Thr Glu Asp Thr Gly Ile Tyr
                 85                  90                  95

Tyr Cys Thr Arg Arg Asn Trp Gly Phe Ala Tyr Trp Gly Gln Gly Thr
            100                 105                 110

Leu Val Thr Val Ser Ala
            115

<210> SEQ ID NO 44
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Ile Leu Leu Thr Gln Ser Pro Ala Ile Leu Ser Val Ser Pro Gly
 1               5                  10                  15

Glu Arg Val Ser Phe Ser Cys Arg Ala Ser Gln Thr Ile Gly Thr Ser
                 20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Thr Asn Ser Trp Pro Leu
                 85                  90                  95

Thr Phe Gly Ala Gly Thr Lys Leu Glu Leu Lys
            100                 105

<210> SEQ ID NO 45
<211> LENGTH: 503
<212> TYPE: PRT
<213> ORGANISM: Homo sapiens

<400> SEQUENCE: 45

Met Glu Pro Ala Gly Pro Ala Pro Gly Arg Leu Gly Pro Leu Leu Cys
 1               5                  10                  15

Leu Leu Leu Ala Ala Ser Cys Ala Trp Ser Gly Val Ala Gly Glu Glu
                 20                  25                  30

Glu Leu Gln Val Ile Gln Pro Asp Lys Ser Val Ser Val Ala Ala Gly
            35                  40                  45

Glu Ser Ala Ile Leu His Cys Thr Val Thr Ser Leu Ile Pro Val Gly
 50                  55                  60

Pro Ile Gln Trp Phe Arg Gly Ala Gly Pro Ala Arg Glu Leu Ile Tyr
 65                  70                  75                  80

Asn Gln Lys Glu Gly His Phe Pro Arg Val Thr Thr Val Ser Glu Ser
                 85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
            115                 120                 125

Pro Asp Thr Glu Phe Lys Ser Gly Ala Gly Thr Glu Leu Ser Val Arg
            130                 135                 140
```

Ala Lys Pro Ser Ala Pro Val Val Ser Gly Pro Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
                260                 265                 270

Gln Val Arg Lys Phe Tyr Pro Gln Arg Leu Gln Leu Thr Trp Leu Glu
            275                 280                 285

Asn Gly Asn Val Ser Arg Thr Glu Thr Ala Ser Thr Val Thr Glu Asn
        290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
                340                 345                 350

Lys Glu Gln Gly Ser Asn Thr Ala Ala Glu Asn Thr Gly Ser Asn Glu
            355                 360                 365

Arg Asn Ile Tyr Ile Val Val Gly Val Val Cys Thr Leu Leu Val Ala
        370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
                405                 410                 415

Arg Glu Ile Thr Gln Asp Thr Asn Asp Ile Thr Tyr Ala Asp Leu Asn
            420                 425                 430

Leu Pro Lys Gly Lys Lys Pro Ala Pro Gln Ala Ala Glu Pro Asn Asn
        435                 440                 445

His Thr Glu Tyr Ala Ser Ile Gln Thr Ser Pro Gln Pro Ala Ser Glu
    450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
            500

<210> SEQ ID NO 46
<211> LENGTH: 398
<212> TYPE: PRT
<213> ORGANISM: Homo sapiens

<400> SEQUENCE: 46

Met Pro Val Pro Ala Ser Trp Pro His Leu Pro Ser Pro Phe Leu Leu

```
            1               5                   10                  15
          Met Thr Leu Leu Leu Gly Arg Leu Thr Gly Val Ala Gly Glu Asp Glu
                          20                  25                  30
          Leu Gln Val Ile Gln Pro Glu Lys Ser Val Ser Val Ala Ala Gly Glu
                          35                  40                  45
          Ser Ala Thr Leu Arg Cys Ala Met Thr Ser Leu Ile Pro Val Gly Pro
                          50                  55                  60
          Ile Met Trp Phe Arg Gly Ala Gly Ala Gly Arg Glu Leu Ile Tyr Asn
          65                      70                  75                  80
          Gln Lys Glu Gly His Phe Pro Arg Val Thr Thr Val Ser Glu Leu Thr
                              85                  90                  95
          Lys Arg Asn Asn Leu Asp Phe Ser Ile Ser Ile Ser Asn Ile Thr Pro
                          100                 105                 110
          Ala Asp Ala Gly Thr Tyr Tyr Cys Val Lys Phe Arg Lys Gly Ser Pro
                          115                 120                 125
          Asp Asp Val Glu Phe Lys Ser Gly Ala Gly Thr Glu Leu Ser Val Arg
                          130                 135                 140
          Ala Lys Pro Ser Ala Pro Val Val Ser Gly Pro Ala Val Arg Ala Thr
          145                     150                 155                 160
          Pro Glu His Thr Val Ser Phe Thr Cys Glu Ser His Gly Phe Ser Pro
                              165                 170                 175
          Arg Asp Ile Thr Leu Lys Trp Phe Lys Asn Gly Asn Glu Leu Ser Asp
                          180                 185                 190
          Phe Gln Thr Asn Val Asp Pro Ala Gly Asp Ser Val Ser Tyr Ser Ile
                          195                 200                 205
          His Ser Thr Ala Arg Val Val Leu Thr Arg Gly Asp Val His Ser Gln
                          210                 215                 220
          Val Ile Cys Glu Ile Ala His Ile Thr Leu Gln Gly Asp Pro Leu Arg
          225                     230                 235                 240
          Gly Thr Ala Asn Leu Ser Glu Ala Ile Arg Val Pro Pro Thr Leu Glu
                              245                 250                 255
          Val Thr Gln Gln Pro Met Arg Ala Glu Asn Gln Ala Asn Val Thr Cys
                          260                 265                 270
          Gln Val Ser Asn Phe Tyr Pro Arg Gly Leu Gln Leu Thr Trp Leu Glu
                          275                 280                 285
          Asn Gly Asn Val Ser Arg Thr Glu Thr Ala Ser Thr Leu Ile Glu Asn
                          290                 295                 300
          Lys Asp Gly Thr Tyr Asn Trp Met Ser Trp Leu Leu Val Asn Thr Cys
          305                     310                 315                 320
          Ala His Arg Asp Asp Val Val Leu Thr Cys Gln Val Glu His Asp Gly
                              325                 330                 335
          Gln Gln Ala Val Ser Lys Ser Tyr Ala Leu Glu Ile Ser Ala His Gln
                          340                 345                 350
          Lys Glu His Gly Ser Asp Ile Thr His Glu Ala Ala Leu Ala Pro Thr
                          355                 360                 365
          Ala Pro Leu Leu Val Ala Leu Leu Gly Pro Lys Leu Leu Leu Val
                          370                 375                 380
          Val Gly Val Ser Ala Ile Tyr Ile Cys Trp Lys Gln Lys Ala
          385                     390                 395

<210> SEQ ID NO 47
<211> LENGTH: 509
<212> TYPE: PRT
<213> ORGANISM: Mus musculus
```

<400> SEQUENCE: 47

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
                20                  25                  30

Glu Leu Lys Val Thr Gln Pro Glu Lys Ser Val Ser Val Ala Ala Gly
            35                  40                  45

Asp Ser Thr Val Leu Asn Cys Thr Leu Thr Ser Leu Leu Pro Val Gly
        50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Thr Glu Val Tyr
        130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
        370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
```

```
                    405                 410                 415
Lys Asn Ala Arg Glu Ile Thr Gln Ile Gln Asp Thr Asn Asp Ile Asn
                420                 425                 430

Asp Ile Thr Tyr Ala Asp Leu Asn Leu Pro Lys Glu Lys Lys Pro Ala
            435                 440                 445

Pro Arg Ala Pro Glu Pro Asn Asn His Thr Glu Tyr Ala Ser Ile Glu
450                 455                 460

Thr Gly Lys Val Pro Arg Pro Glu Asp Thr Leu Thr Tyr Ala Asp Leu
465                 470                 475                 480

Asp Met Val His Leu Ser Arg Ala Gln Pro Ala Pro Lys Pro Glu Pro
                485                 490                 495

Ser Phe Ser Glu Tyr Ala Ser Val Gln Val Gln Arg Lys
            500                 505

<210> SEQ ID NO 48
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 49
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Tyr Phe Asp Tyr Trp Gly Gln Gly Thr Leu Val Thr Val Ser Ser
1               5                   10                  15

<210> SEQ ID NO 50
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50
```

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Asp Tyr Gly Gly Ser Tyr Thr Tyr Tyr Pro Asp Ser
    50                  55                  60

Val Lys Gly Arg Phe Thr Ile Ser Arg Asp Asn Ala Lys Tyr Thr Leu
65                  70                  75                  80

Tyr Leu Gln Met Ser Ser Leu Arg Ser Glu Asp Thr Ala Leu Tyr Tyr
                85                  90                  95

Cys Ala Arg Pro Pro Tyr Asp Asp Tyr Tyr Gly Gly Phe Ala Tyr Trp
            100                 105                 110

Gly Gln Gly Thr Leu Val Thr Val Ser Ala
            115                 120

<210> SEQ ID NO 51
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 52
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Asp Tyr Gly Gly Ser Tyr Thr Tyr Tyr Ala Asp Ser
    50                  55                  60

```
Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Lys Pro Pro Tyr Asp Asp Tyr Tyr Gly Gly Phe Ala Tyr Trp
            100                 105                 110

Gly Gln Gly Thr Leu Val Thr Val Ser Ser
        115                 120
```

<210> SEQ ID NO 53
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ala Thr Ile Ser Asp Tyr Gly Ser Tyr Thr Tyr Tyr Ala Asp Ser
         50                  55                  60

Val Lys Gly Arg Phe Thr Ile Ser Glu Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Pro Pro Tyr Asp Asp Tyr Tyr Gly Gly Phe Ala Tyr Trp
            100                 105                 110

Gly Gln Gly Thr Leu Val Thr Val Ser Ser
        115                 120
```

<210> SEQ ID NO 54
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95
```

<210> SEQ ID NO 55
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 55

Tyr Thr Phe Gly Gln Gly Thr Lys Leu Glu Ile Lys
1               5                   10

<210> SEQ ID NO 56
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Asn Arg
                85                  90                  95

Glu Leu Pro Cys Thr Phe Gly Gly Gly Thr Lys Leu Glu Ile Lys
            100                 105                 110

<210> SEQ ID NO 57
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

-continued

<210> SEQ ID NO 58
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 58

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Ser Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Asn Arg
                85                  90                  95

Glu Leu Pro Cys Thr Phe Gly Gln Gly Thr Lys Leu Glu Ile Lys
            100                 105                 110
```

<210> SEQ ID NO 59
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 59

```
Glu Ile Val Leu Thr Gln Ser Pro Ala Thr Leu Ser Leu Ser Pro Gly
1               5                   10                  15

Glu Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Val Tyr Tyr Cys Gln His Asn Arg
                85                  90                  95

Glu Leu Pro Cys Thr Phe Gly Gln Gly Thr Lys Leu Glu Ile Lys
            100                 105                 110
```

<210> SEQ ID NO 60
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

```
Glu Ile Val Leu Thr Gln Ser Pro Ala Thr Leu Ser Leu Ser Pro Gly
1               5                   10                  15
```

Glu Arg Ala Thr Ile Ser Cys Arg Ala Ser Lys Ser Val Ser Ser Ser
                20                  25                  30

Gly Tyr Gly Tyr Met His Trp Tyr Gln Gln Lys Pro Gly Gln Ala Pro
            35                  40                  45

Arg Leu Leu Ile Tyr Leu Ala Ser Asn Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Val Tyr Tyr Cys Gln His Asn Arg
                85                  90                  95

Glu Leu Pro Ser Thr Phe Gly Gln Gly Thr Lys Leu Glu Ile Lys
            100                 105                 110

<210> SEQ ID NO 61
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
50                  55                  60

Gln Gly Arg Val Thr Asn Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 62
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Glu Phe Gln Leu Gln Gln Ser Gly Ala Glu Leu Val Lys Pro Gly Ala
1               5                   10                  15

Ser Val Lys Ile Ser Cys Lys Ala Ser Gly Tyr Ser Leu Thr Gly Tyr
                20                  25                  30

Asn Met Asn Trp Val Lys Gln Ser Arg Gly Lys Ser Leu Glu Trp Ile
            35                  40                  45

Gly Asn Ile Asn Pro His Tyr Gly Ser Ser Thr Tyr Asn Gln Asn Phe
50                  55                  60

Lys Asp Lys Ala Thr Leu Thr Val Asp Lys Ser Ser Ser Ala Ala Tyr
65                  70                  75                  80

Met Gln Phe Asn Ser Leu Thr Ser Glu Asp Ser Ala Val Tyr Tyr Cys

-continued

```
                85                  90                  95

Ala Arg Glu Gly Tyr Asp Gly Val Phe Asp Tyr Trp Gly Gln Gly Thr
            100                 105                 110

Thr Leu Thr Val Ser Ser
        115

<210> SEQ ID NO 63
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 64
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Gly Tyr
            20                  25                  30

Asn Met Asn Trp Val Arg Gln Ala Pro Gly Gln Gly Leu Glu Trp Met
        35                  40                  45

Gly Asn Ile Asn Pro His Tyr Gly Ser Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Asp Gly Val Phe Asp Tyr Trp Gly Gln Gly Thr
            100                 105                 110

Leu Val Thr Val Ser Ser
        115

<210> SEQ ID NO 65
<211> LENGTH: 118
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Gly Tyr
            20                  25                  30

Asn Met Asn Trp Val Arg Gln Ala Pro Gly Gln Gly Leu Glu Trp Ile
        35                  40                  45

Gly Asn Ile Asn Pro His Tyr Gly Ser Ser Tyr Ala Gln Lys Phe
    50                  55                  60

Gln Gly Arg Val Thr Met Thr Val Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Asp Gly Val Phe Asp Tyr Trp Gly Gln Gly Thr
            100                 105                 110

Leu Val Thr Val Ser Ser
        115

```
<210> SEQ ID NO 66
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66
```

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Leu Thr Gly Tyr
            20                  25                  30

Asn Met Asn Trp Val Arg Gln Ala Pro Gly Gln Gly Leu Glu Trp Ile
        35                  40                  45

Gly Asn Ile Asn Pro His Tyr Gly Ser Ser Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Phe Ser Ser Leu Arg Ser Glu Asp Thr Ala Val Tyr Tyr Cys
                85                  90                  95

Ala Arg Glu Gly Tyr Asp Gly Val Phe Asp Tyr Trp Gly Gln Gly Thr
            100                 105                 110

Leu Val Thr Val Ser Ser
        115

```
<210> SEQ ID NO 67
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 67

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Leu Thr Gly Tyr
            20                  25                  30

Asn Met Asn Trp Val Arg Gln Ala Pro Gly Gln Gly Leu Glu Trp Ile
        35                  40                  45

Gly Asn Ile Asn Pro His Tyr Gly Ser Ser Thr Tyr Ala Gln Lys Phe
    50                  55                  60

Gln Gly Arg Ala Thr Leu Thr Val Asp Lys Ser Thr Ser Thr Ala Tyr
65                  70                  75                  80

Met Glu Phe Ser Ser Leu Thr Ser Glu Asp Thr Ala Val Tyr Tyr Cys
                85                  90                  95

Ala Arg Glu Gly Tyr Asp Gly Val Phe Asp Tyr Trp Gly Gln Gly Thr
            100                 105                 110

Leu Val Thr Val Ser Ser
            115

<210> SEQ ID NO 68
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

<210> SEQ ID NO 69
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Val Thr Ser Asn Leu Ala Ser Gly Val Pro Thr Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Arg Thr
                85                  90                  95

Phe Gly Gly Gly Thr Lys Leu Glu Ile Lys
            100                 105

<210> SEQ ID NO 70
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

<210> SEQ ID NO 71
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
                20                  25                  30

His Trp Tyr Gln Gln Lys Pro Gly Gln Ala Pro Arg Leu Leu Ile Tyr
            35                  40                  45

Val Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Arg Thr
                85                  90                  95

Phe Gly Gln Gly Thr Lys Leu Glu Ile Lys
            100                 105

<210> SEQ ID NO 72
<211> LENGTH: 106
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Leu Ile Tyr
        35                  40                  45

Val Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Arg Thr
                85                  90                  95

Phe Gly Gln Gly Thr Lys Leu Glu Ile Lys
            100                 105

<210> SEQ ID NO 73
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Trp Ile Tyr
        35                  40                  45

Val Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Arg Thr
                85                  90                  95

Phe Gly Gln Gly Thr Lys Leu Glu Ile Lys
            100                 105

<210> SEQ ID NO 74
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Glu Ile Val Leu Thr Gln Ser Pro Ala Thr Leu Ser Leu Ser Pro Gly
1               5                   10                  15

Glu Arg Val Thr Met Ser Cys Arg Ala Ser Ser Val Ser Tyr Met
            20                  25                  30

His Trp Tyr Gln Gln Lys Pro Gly Gln Ala Pro Arg Pro Trp Ile Tyr

```
             35                  40                  45
Val Thr Ser Asn Leu Ala Ser Gly Val Pro Ala Arg Phe Ser Gly Ser
         50                  55                  60

Gly Ser Gly Thr Asp Tyr Thr Leu Thr Ile Ser Ser Val Ser Pro Glu
65                   70                  75                  80

Asp Phe Ala Val Tyr Tyr Cys Gln Gln Trp Ser Ser Asn Pro Arg Thr
                 85                  90                  95

Phe Gly Gln Gly Thr Lys Leu Glu Ile Lys
             100                 105
```

UNITED STATES PATENT AND TRADEMARK OFFICE
CERTIFICATE OF CORRECTION

PATENT NO. : 11,779,642 B2  
APPLICATION NO. : 16/463062  
DATED : October 10, 2023  
INVENTOR(S) : Pincetic et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 733 days.

Signed and Sealed this  
Nineteenth Day of August, 2025

Coke Morgan Stewart  
*Acting Director of the United States Patent and Trademark Office*